(12) United States Patent
Hewitt et al.

(10) Patent No.: US 12,226,102 B2
(45) Date of Patent: Feb. 18, 2025

(54) DEVICES FOR THERAPEUTIC VASCULAR PROCEDURES

(71) Applicant: MICROVENTION, INC., Aliso Viejo, CA (US)

(72) Inventors: Todd Hewitt, Laguna Niguel, CA (US); Brian E. Merritt, San Clemente, CA (US); William R. Patterson, Huntington Beach, CA (US); James M. Thompson, Lake Forest, CA (US); Claudio Plaza, Rancho Santa Margarita, CA (US); Hung P. Tran, Midway City, CA (US)

(73) Assignee: MICROVENTION, INC., Aliso Viejo, CA (US)

( * ) Notice: Subject to any disclaimer, the term of this patent is extended or adjusted under 35 U.S.C. 154(b) by 0 days.

(21) Appl. No.: 18/144,435

(22) Filed: May 8, 2023

(65) Prior Publication Data
US 2023/0270441 A1 Aug. 31, 2023

Related U.S. Application Data

(63) Continuation of application No. 16/373,476, filed on Apr. 2, 2019, now Pat. No. 11,678,886, which is a
(Continued)

(51) Int. Cl.
*A61B 17/12* (2006.01)
*A61B 17/00* (2006.01)
(Continued)

(52) U.S. Cl.
CPC .. *A61B 17/12113* (2013.01); *A61B 17/12031* (2013.01); *A61B 17/1214* (2013.01);
(Continued)

(58) Field of Classification Search
CPC ........ A61B 17/12113; A61B 17/12172; A61B 2017/1205
See application file for complete search history.

(56) References Cited

U.S. PATENT DOCUMENTS

| 3,874,388 A | 4/1975 | King et al. |
| 4,282,875 A | 8/1981 | Serbinenko |
(Continued)

FOREIGN PATENT DOCUMENTS

| AU | 2009242528 | 3/2016 |
| CA | 2722037 | 10/2009 |
(Continued)

OTHER PUBLICATIONS

A Complete Microcatheter Portfolio; A Broad Selection of Microcatheters. Boston Scientific Brochure 2007.
(Continued)

*Primary Examiner* — Julian W Woo
(74) *Attorney, Agent, or Firm* — ONE LLP

(57) ABSTRACT

Devices for treating a cerebral aneurysm may include proximal and distal self-expanding resilient permeable shells each including a plurality of elongate resilient filaments having a braided structure. The distal permeable shell may include a first plurality of filaments gathered at least at the proximal end thereof. The proximal permeable shell may include a second plurality of filaments are gathered at least at the proximal end thereof. The expanded state of the distal permeable shell may have a convex shape at the distal end of the distal permeable shell and the expanded state of the proximal permeable shell may have a generally convex shape at the proximal end of the proximal permeable shell. The expanded states of the distal and proximal permeable shells may also define a toroidal cavity through which an elongate support member extends.

20 Claims, 47 Drawing Sheets

Related U.S. Application Data continuation of application No. 15/404,492, filed on Jan. 12, 2017, now abandoned, which is a continuation of application No. 14/684,212, filed on Apr. 10, 2015, now Pat. No. 9,629,635.

(60) Provisional application No. 62/093,313, filed on Dec. 17, 2014, provisional application No. 61/979,416, filed on Apr. 14, 2014.

(51) Int. Cl.
    *A61B 90/00*     (2016.01)
    *A61M 25/00*     (2006.01)

(52) U.S. Cl.
    CPC .... *A61B 17/12145* (2013.01); *A61B 17/1215* (2013.01); *A61B 17/12172* (2013.01); *A61B 17/12177* (2013.01); *A61B 2017/00526* (2013.01); *A61B 2017/00867* (2013.01); *A61B 2017/00893* (2013.01); *A61B 2017/00898* (2013.01); *A61B 2017/1205* (2013.01); *A61B 2017/12068* (2013.01); *A61B 2090/3966* (2016.02); *A61F 2310/00149* (2013.01); *A61M 2025/0042* (2013.01)

(56) References Cited

U.S. PATENT DOCUMENTS

| | | |
|---|---|---|
| 4,346,712 A | 8/1982 | Handa et al. |
| 4,402,319 A | 9/1983 | Handa et al. |
| 4,425,908 A | 1/1984 | Simon |
| 4,619,246 A | 10/1986 | Molgaard-Nielsen et al. |
| 4,675,361 A | 6/1987 | Ward |
| 4,729,278 A | 3/1988 | Graeff |
| 4,998,539 A | 3/1991 | Delsanti |
| 5,061,275 A | 10/1991 | Wallsten et al. |
| 5,071,407 A | 12/1991 | Termin et al. |
| 5,108,407 A | 4/1992 | Geremia et al. |
| 5,122,136 A | 6/1992 | Glugielmi et al. |
| 5,154,705 A | 10/1992 | Fleischhacker et al. |
| 5,158,545 A | 10/1992 | Trudell et al. |
| 5,165,421 A | 11/1992 | Fleischhacker et al. |
| 5,263,963 A | 11/1993 | Garrison |
| 5,334,210 A | 8/1994 | Gianturco |
| 5,378,239 A | 1/1995 | Termin |
| 5,536,247 A | 7/1996 | Thornton |
| 5,562,725 A | 10/1996 | Schmitt et al. |
| 5,569,245 A | 10/1996 | Glugielmi et al. |
| 5,578,074 A | 11/1996 | Mirigian |
| 5,591,222 A | 1/1997 | Susawa et al. |
| 5,601,595 A | 2/1997 | Smith |
| 5,630,840 A | 5/1997 | Mayer |
| D380,266 S | 6/1997 | Boatman et al. |
| 5,645,559 A | 7/1997 | Hachtman et al. |
| 5,725,552 A | 3/1998 | Kotula |
| 5,725,570 A | 3/1998 | Heath |
| 5,733,294 A | 3/1998 | Forber |
| 5,749,883 A | 5/1998 | Halpern |
| 5,759,161 A | 6/1998 | Ogawa |
| 5,766,219 A | 6/1998 | Horton |
| 5,846,261 A | 12/1998 | Kotula et al. |
| 5,873,907 A | 2/1999 | Frantzen |
| 5,907,893 A | 6/1999 | Zadno-Azizi |
| 5,916,235 A | 6/1999 | Guglielmi |
| 5,925,060 A | 7/1999 | Forber |
| 5,927,345 A | 7/1999 | Samson |
| 5,928,260 A | 7/1999 | Chin et al. |
| 5,935,148 A | 8/1999 | Villar et al. |
| 5,944,733 A | 8/1999 | Engelson |
| 5,944,738 A | 8/1999 | Amplatz |
| 5,951,599 A | 9/1999 | McCrory |
| 5,964,797 A | 10/1999 | Ho |
| 5,980,554 A | 11/1999 | Lenker et al. |
| 5,984,929 A | 11/1999 | Bashiri et al. |
| 5,989,242 A | 11/1999 | Saadat et al. |
| 6,033,423 A | 3/2000 | Ken et al. |
| 6,063,070 A | 5/2000 | Eder |
| 6,063,104 A | 5/2000 | Villar et al. |
| 6,086,577 A | 7/2000 | Ken et al. |
| 6,093,199 A | 7/2000 | Brown et al. |
| 6,123,715 A | 9/2000 | Amplatz |
| 6,139,564 A | 10/2000 | Teoh et al. |
| 6,142,975 A | 11/2000 | Jalisi et al. |
| 6,152,144 A | 11/2000 | Lesh et al. |
| 6,156,061 A | 12/2000 | Wallace et al. |
| 6,159,206 A | 12/2000 | Ogawa |
| 6,168,615 B1 | 1/2001 | Ken et al. |
| 6,168,618 B1 | 1/2001 | Frantzen |
| 6,168,622 B1 | 1/2001 | Mazzocchi |
| 6,190,402 B1 | 2/2001 | Horton et al. |
| 6,193,708 B1 | 2/2001 | Ken et al. |
| 6,203,779 B1 | 3/2001 | Ricci et al. |
| 6,221,086 B1 | 4/2001 | Forber |
| 6,238,403 B1 | 5/2001 | Greene, Jr. et al. |
| 6,277,126 B1 | 8/2001 | Barry et al. |
| 6,290,721 B1 | 9/2001 | Heath |
| 6,315,709 B1 | 11/2001 | Garibaldi et al. |
| 6,325,815 B1 | 12/2001 | Kusleika |
| 6,342,068 B1 | 1/2002 | Thompson |
| 6,344,048 B1 | 2/2002 | Chin et al. |
| 6,346,117 B1 | 2/2002 | Greenhalgh |
| 6,350,270 B1 | 2/2002 | Roue |
| 6,368,338 B1 | 4/2002 | Konya |
| 6,368,339 B1 | 4/2002 | Amplatz |
| 6,375,668 B1 | 4/2002 | Gifford |
| 6,375,670 B1 | 4/2002 | Greenhalgh |
| 6,383,174 B1 | 5/2002 | Eder |
| 6,391,037 B1 | 5/2002 | Greenhalgh |
| 6,425,914 B1 | 7/2002 | Wallace et al. |
| 6,428,558 B1 | 8/2002 | Jones et al. |
| 6,447,531 B1 | 9/2002 | Amplatz |
| 6,454,780 B1 | 9/2002 | Wallace |
| 6,461,370 B1 | 10/2002 | Gray et al. |
| 6,463,317 B1 | 10/2002 | Kucharczyk |
| 6,468,266 B1 | 10/2002 | Bashiri et al. |
| 6,478,773 B1 | 11/2002 | Gandhi et al. |
| 6,500,149 B2 | 12/2002 | Gandhi et al. |
| 6,506,204 B2 | 1/2003 | Mazzocchi |
| 6,511,468 B1 | 1/2003 | Cragg et al. |
| 6,551,303 B1 | 4/2003 | Van Tassel et al. |
| 6,579,303 B2 | 6/2003 | Amplatz |
| 6,585,748 B1 | 7/2003 | Jeffree |
| 6,589,256 B2 | 7/2003 | Forber |
| 6,589,265 B1 | 7/2003 | Palmer et al. |
| 6,599,308 B2 | 7/2003 | Amplatz |
| 6,605,102 B1 | 8/2003 | Mazzocchi et al. |
| 6,605,111 B2 | 8/2003 | Bose et al. |
| 6,607,539 B1 | 8/2003 | Hayashi et al. |
| 6,613,074 B1 | 9/2003 | Mitelberg |
| 6,626,939 B1 | 9/2003 | Burnside et al. |
| 6,632,241 B1 | 10/2003 | Hancock |
| 6,635,068 B1 | 10/2003 | Dubrul et al. |
| 6,638,257 B2 | 10/2003 | Amplatz |
| 6,652,556 B1 | 11/2003 | Van Tassel et al. |
| 6,666,882 B1 | 12/2003 | Bose et al. |
| 6,669,721 B1 | 12/2003 | Bose et al. |
| 6,682,546 B2 | 1/2004 | Amplatz |
| 6,689,150 B1 | 2/2004 | Van Tassel |
| 6,689,486 B2 | 2/2004 | Ho et al. |
| 6,719,778 B1 | 4/2004 | Van Tassel et al. |
| 6,730,119 B1 | 5/2004 | Smalling |
| 6,743,236 B2 | 6/2004 | Barry et al. |
| 6,743,251 B1 | 6/2004 | Eder |
| 6,746,468 B1 | 6/2004 | Sepetka et al. |
| 6,746,890 B2 | 6/2004 | Gupta et al. |
| 6,752,826 B2 | 6/2004 | Holloway et al. |
| 6,780,196 B2 | 8/2004 | Chin et al. |
| 6,811,560 B2 | 11/2004 | Jones et al. |
| 6,818,006 B2 | 11/2004 | Douk et al. |
| 6,855,153 B2 | 2/2005 | Saadat |
| 6,855,154 B2 | 2/2005 | Abdel-Gawwad |
| 6,878,384 B2 | 4/2005 | Cruise et al. |
| 6,936,055 B1 | 8/2005 | Ken et al. |

(56) References Cited

U.S. PATENT DOCUMENTS

| | | |
|---|---|---|
| 6,940,209 B2 | 9/2005 | Henderson |
| 6,953,472 B2 | 10/2005 | Palmer et al. |
| 6,953,473 B2 | 10/2005 | Porter |
| 6,966,892 B2 | 11/2005 | Gandhi et al. |
| 6,994,092 B2 | 2/2006 | van der Burg et al. |
| 7,001,409 B2 | 2/2006 | Amplatz |
| 7,004,962 B2 | 2/2006 | Stinson |
| 7,011,671 B2 | 3/2006 | Welch |
| 7,044,958 B2 | 5/2006 | Douk et al. |
| 7,052,513 B2 | 5/2006 | Thompson |
| 7,083,632 B2 | 8/2006 | Avellanet et al. |
| 7,101,390 B2 | 9/2006 | Nelson |
| 7,122,043 B2 | 10/2006 | Greenhalgh et al. |
| 7,128,736 B1 | 10/2006 | Abrams et al. |
| 7,179,276 B2 | 2/2007 | Barry et al. |
| 7,182,774 B2 | 2/2007 | Barry et al. |
| 7,195,636 B2 | 3/2007 | Avellanet et al. |
| 7,198,613 B2 | 4/2007 | Gandhi et al. |
| 7,201,918 B2 | 4/2007 | Cruise |
| 7,229,454 B2 | 6/2007 | Tran |
| 7,229,461 B2 | 7/2007 | Chin et al. |
| 7,275,471 B2 | 10/2007 | Nishri et al. |
| 7,326,225 B2 | 2/2008 | Ferrera et al. |
| 7,329,279 B2 | 2/2008 | Haug et al. |
| 7,331,980 B2 | 2/2008 | Dubrul |
| 7,410,482 B2 | 8/2008 | Murphy |
| 7,419,503 B2 | 9/2008 | Pulnev et al. |
| 7,490,396 B2 | 2/2009 | Bradley |
| 7,524,319 B2 | 4/2009 | Dubrul |
| 7,569,066 B2 | 8/2009 | Gerberding |
| 7,573,382 B2 | 8/2009 | Choubey et al. |
| 7,575,582 B2 | 8/2009 | Gandhi et al. |
| 7,578,826 B2 | 8/2009 | Gandhi et al. |
| 7,597,704 B2 | 10/2009 | Frazier et al. |
| 7,648,532 B2 | 1/2010 | Greenhalgh et al. |
| 7,695,488 B2 | 4/2010 | Berenstein |
| 7,722,637 B2 | 5/2010 | Barry et al. |
| 7,745,732 B2 | 6/2010 | Michael et al. |
| 7,806,919 B2 | 10/2010 | Bloom et al. |
| 7,862,577 B2 | 1/2011 | Gray et al. |
| 7,942,925 B2 | 5/2011 | Yodaf |
| 7,967,747 B2 | 6/2011 | Eidenschink |
| 7,989,703 B2 | 8/2011 | Schaffer |
| RE42,758 E | 9/2011 | Ken et al. |
| 8,043,326 B2 | 10/2011 | Hancock |
| 8,043,329 B2 | 10/2011 | Khairkhahan |
| 8,066,757 B2 | 11/2011 | Ferrera et al. |
| 8,142,456 B2 | 3/2012 | Rosqueta et al. |
| 8,182,506 B2 | 5/2012 | Fitz et al. |
| 8,192,480 B2 | 6/2012 | Tieu et al. |
| 8,313,505 B2 | 11/2012 | Amplatz et al. |
| 8,323,309 B2 | 12/2012 | Khairkhahan et al. |
| 8,398,670 B2 | 3/2013 | Amplatz |
| 8,430,012 B1 | 4/2013 | Marchand |
| 8,506,619 B2 | 8/2013 | Ortiz et al. |
| 8,551,132 B2 | 10/2013 | Eskridge et al. |
| 8,597,320 B2 | 12/2013 | Sepetka |
| 8,597,323 B1 | 12/2013 | Plaza et al. |
| 8,690,907 B1 | 4/2014 | Janardhan et al. |
| 8,715,338 B2 | 5/2014 | Frid |
| 8,728,117 B1 | 5/2014 | Janardhan et al. |
| 8,758,395 B2 | 6/2014 | Kleshinski et al. |
| 8,795,330 B1 | 8/2014 | Janardhan et al. |
| 8,840,735 B2 | 9/2014 | Schaffer |
| 8,845,679 B1 | 9/2014 | Janardhan et al. |
| 8,926,681 B2 | 1/2015 | Levy et al. |
| 9,039,726 B2 | 5/2015 | Becking |
| 9,078,658 B2 | 7/2015 | Hewitt et al. |
| 9,161,758 B2 | 10/2015 | Figulla et al. |
| 9,198,668 B2 | 12/2015 | Theobald et al. |
| 9,198,670 B2 | 12/2015 | Hewitt et al. |
| 9,259,337 B2 | 2/2016 | Cox et al. |
| 9,272,323 B2 | 3/2016 | Schaffer |
| 9,295,473 B2 | 3/2016 | Hewitt et al. |
| 9,351,715 B2 * | 5/2016 | Mach ............... A61B 17/12109 |
| 9,492,174 B2 | 11/2016 | Hewitt et al. |
| 9,504,588 B2 | 11/2016 | Sadisivan et al. |
| 9,585,669 B2 * | 3/2017 | Becking ............... A61M 29/02 |
| 9,597,087 B2 | 3/2017 | Marchand et al. |
| 9,629,635 B2 | 4/2017 | Hewitt et al. |
| 9,687,245 B2 | 6/2017 | Molaei et al. |
| 9,855,047 B2 | 1/2018 | Berez et al. |
| 9,855,051 B2 | 1/2018 | Aboytes et al. |
| 9,955,976 B2 | 5/2018 | Hewitt et al. |
| 10,004,511 B2 | 6/2018 | Molaei et al. |
| 10,123,803 B2 | 11/2018 | Ferrera et al. |
| 10,136,896 B2 | 11/2018 | Hewitt et al. |
| 10,238,393 B2 | 3/2019 | Marchand et al. |
| 10,260,182 B2 | 4/2019 | Thompson et al. |
| 10,260,183 B2 | 4/2019 | Marchand et al. |
| 10,398,441 B2 | 9/2019 | Warner et al. |
| 10,470,773 B2 | 11/2019 | Maguire et al. |
| 10,617,426 B2 | 4/2020 | Aboytes et al. |
| 10,716,573 B2 | 7/2020 | Connor |
| 10,736,758 B2 | 8/2020 | Ruvalcaba et al. |
| 10,856,880 B1 | 12/2020 | Badruddin et al. |
| 10,939,914 B2 | 3/2021 | Hewitt et al. |
| 10,952,739 B2 | 3/2021 | Plaza et al. |
| 11,559,309 B2 | 1/2023 | Rangwala et al. |
| 2001/0031981 A1 | 10/2001 | Evans et al. |
| 2002/0065552 A1 | 5/2002 | Jayaraman et al. |
| 2002/0103542 A1 | 8/2002 | Bilbo |
| 2002/0111647 A1 | 8/2002 | Khairkhahan et al. |
| 2002/0143349 A1 | 10/2002 | Gifford et al. |
| 2002/0143361 A1 | 10/2002 | Douk et al. |
| 2002/0156499 A1 | 10/2002 | Konya et al. |
| 2002/0169473 A1 | 11/2002 | Sepetka et al. |
| 2002/0183787 A1 | 12/2002 | Wahr et al. |
| 2002/0187288 A1 | 12/2002 | Lim et al. |
| 2003/0012816 A1 | 1/2003 | West et al. |
| 2003/0028209 A1 | 2/2003 | Teoh et al. |
| 2003/0040771 A1 | 2/2003 | Hyodoh et al. |
| 2003/0167068 A1 | 9/2003 | Amplatz |
| 2003/0171739 A1 | 9/2003 | Murphy et al. |
| 2003/0171774 A1 | 9/2003 | Freudenthal et al. |
| 2003/0181942 A1 | 9/2003 | Sutton et al. |
| 2003/0187473 A1 | 10/2003 | Berenstein et al. |
| 2003/0199913 A1 | 10/2003 | Dubrul et al. |
| 2004/0059370 A1 | 3/2004 | Green, Jr. et al. |
| 2004/0098027 A1 | 5/2004 | Tech et al. |
| 2004/0111147 A1 | 6/2004 | Rabkin et al. |
| 2004/0122367 A1 | 6/2004 | Sculati et al. |
| 2004/0143239 A1 | 7/2004 | Zhou et al. |
| 2004/0158311 A1 | 8/2004 | Berhow |
| 2004/0172053 A1 | 9/2004 | Barry et al. |
| 2004/0186562 A1 | 9/2004 | Cox |
| 2004/0193206 A1 | 9/2004 | Gerberding et al. |
| 2004/0193208 A1 | 9/2004 | Talpade et al. |
| 2004/0220563 A1 | 11/2004 | Eder |
| 2004/0260333 A1 | 12/2004 | Dubrul et al. |
| 2005/0021075 A1 | 1/2005 | Bonnette et al. |
| 2005/0033408 A1 | 2/2005 | Jones et al. |
| 2005/0053782 A1 | 3/2005 | Sen et al. |
| 2005/0096728 A1 | 5/2005 | Ramer |
| 2005/0112349 A1 | 5/2005 | Laurencin et al. |
| 2005/0113861 A1 | 5/2005 | Corcoran et al. |
| 2005/0113868 A1 | 5/2005 | Devellian et al. |
| 2005/0119684 A1 | 6/2005 | Gutterman et al. |
| 2005/0133046 A1 | 6/2005 | Becker et al. |
| 2005/0137623 A1 | 6/2005 | Jones et al. |
| 2005/0149173 A1 | 7/2005 | Hunter et al. |
| 2005/0216052 A1 | 9/2005 | Mazzocchi et al. |
| 2005/0222489 A1 | 10/2005 | Rahdert et al. |
| 2005/0228422 A1 | 10/2005 | Machold et al. |
| 2005/0228434 A1 | 10/2005 | Amplatz et al. |
| 2005/0267516 A1 | 12/2005 | Soleimani et al. |
| 2005/0277978 A1 | 12/2005 | Greenhalgh |
| 2006/0009798 A1 | 1/2006 | Callister et al. |
| 2006/0009799 A1 | 1/2006 | Kleshinski et al. |
| 2006/0009800 A1 | 1/2006 | Christianson et al. |
| 2006/0052815 A1 | 3/2006 | Fitz et al. |
| 2006/0052816 A1 | 3/2006 | Bates et al. |
| 2006/0064151 A1 | 3/2006 | Guterman et al. |
| 2006/0083721 A1 | 4/2006 | Cohen et al. |

(56) References Cited

U.S. PATENT DOCUMENTS

| | | |
|---|---|---|
| 2006/0106421 A1 | 5/2006 | Teoh |
| 2006/0116708 A1 | 6/2006 | Ogawa et al. |
| 2006/0135947 A1 | 6/2006 | Soltesz et al. |
| 2006/0155323 A1 | 7/2006 | Porter et al. |
| 2006/0178694 A1 | 8/2006 | Greenhalgh et al. |
| 2006/0200192 A1 | 9/2006 | Fitz et al. |
| 2006/0200234 A1 | 9/2006 | Hines |
| 2006/0212055 A1 | 9/2006 | Karabey et al. |
| 2006/0217799 A1 | 9/2006 | Mailander et al. |
| 2006/0235464 A1 | 10/2006 | Avellanet et al. |
| 2006/0247680 A1 | 11/2006 | Amplatz et al. |
| 2006/0252984 A1 | 11/2006 | Rahdert et al. |
| 2006/0253149 A1 | 11/2006 | Gandhi et al. |
| 2006/0271086 A1 | 11/2006 | Ramzipoor et al. |
| 2007/0021816 A1 | 1/2007 | Rudin |
| 2007/0031584 A1 | 2/2007 | Roth |
| 2007/0061006 A1 | 3/2007 | Desatnik et al. |
| 2007/0088387 A1 | 4/2007 | Eskridge et al. |
| 2007/0100419 A1 | 5/2007 | Licata et al. |
| 2007/0106311 A1* | 5/2007 | Wallace .......... A61F 2/06 606/151 |
| 2007/0106323 A1 | 5/2007 | Barry et al. |
| 2007/0112380 A1 | 5/2007 | Figulla et al. |
| 2007/0142906 A1 | 6/2007 | Figulla et al. |
| 2007/0144124 A1 | 6/2007 | Schewe et al. |
| 2007/0167911 A1 | 7/2007 | Gandhi et al. |
| 2007/0167980 A1 | 7/2007 | Figulla et al. |
| 2007/0173928 A1 | 7/2007 | Morsi |
| 2007/0203062 A1 | 8/2007 | Ellis-Behnke et al. |
| 2007/0208373 A1 | 9/2007 | Zaver et al. |
| 2007/0208376 A1 | 9/2007 | Meng |
| 2007/0225760 A1 | 9/2007 | Moszner et al. |
| 2007/0233186 A1 | 10/2007 | Meng |
| 2007/0255388 A1 | 11/2007 | Rudakov et al. |
| 2007/0265656 A1 | 11/2007 | Amplatz et al. |
| 2007/0288083 A1 | 12/2007 | Hines |
| 2007/0299464 A1 | 12/2007 | Cruise et al. |
| 2008/0033341 A1 | 2/2008 | Grad |
| 2008/0033366 A1 | 2/2008 | Matson |
| 2008/0033475 A1 | 2/2008 | Meng |
| 2008/0033478 A1 | 2/2008 | Meng |
| 2008/0097495 A1 | 4/2008 | Feller, III et al. |
| 2008/0119886 A1 | 5/2008 | Greenhalgh et al. |
| 2008/0161936 A1 | 7/2008 | Feller et al. |
| 2008/0195139 A1 | 8/2008 | Donald et al. |
| 2008/0200945 A1 | 8/2008 | Amplatz et al. |
| 2008/0221600 A1 | 9/2008 | Dieck et al. |
| 2008/0228215 A1 | 9/2008 | Strauss et al. |
| 2009/0025820 A1 | 1/2009 | Adams |
| 2009/0062812 A1 | 3/2009 | Fitz et al. |
| 2009/0062834 A1 | 3/2009 | Moftakhar |
| 2009/0062841 A1 | 3/2009 | Amplatz et al. |
| 2009/0082803 A1 | 3/2009 | Adams et al. |
| 2009/0099647 A1 | 4/2009 | Glimsdale et al. |
| 2009/0112305 A1 | 4/2009 | Goldmann et al. |
| 2009/0132024 A1 | 5/2009 | Berkhoff |
| 2009/0163780 A1 | 6/2009 | Tieu |
| 2009/0227976 A1 | 9/2009 | Calabria |
| 2009/0275974 A1 | 11/2009 | Marchand |
| 2009/0287291 A1 | 11/2009 | Becking et al. |
| 2009/0287294 A1 | 11/2009 | Rosqueta et al. |
| 2009/0318948 A1 | 12/2009 | Linder et al. |
| 2010/0004679 A1 | 1/2010 | Osypka |
| 2010/0023048 A1 | 1/2010 | Mach |
| 2010/0023105 A1 | 1/2010 | Levy et al. |
| 2010/0069948 A1 | 3/2010 | Veznedaroglu et al. |
| 2010/0094409 A1 | 4/2010 | Barker et al. |
| 2010/0106235 A1 | 4/2010 | Kariniemi et al. |
| 2011/0022149 A1 | 1/2011 | Cox |
| 2011/0029008 A1 | 2/2011 | Gesswein |
| 2011/0046658 A1 | 2/2011 | Connor et al. |
| 2011/0046719 A1 | 2/2011 | Frid |
| 2011/0054515 A1 | 3/2011 | Bridgeman |
| 2011/0082493 A1 | 4/2011 | Samson et al. |
| 2011/0152823 A1 | 6/2011 | Mohiuddin et al. |
| 2011/0152993 A1 | 6/2011 | Marchand et al. |
| 2011/0202085 A1 | 8/2011 | Loganathan et al. |
| 2011/0208227 A1 | 8/2011 | Becking |
| 2011/0208233 A1 | 8/2011 | McGuckin |
| 2011/0224776 A1 | 9/2011 | Sepekta et al. |
| 2011/0295298 A1 | 12/2011 | Moszner |
| 2011/0319926 A1 | 12/2011 | Becking |
| 2012/0065667 A1 | 3/2012 | Javois et al. |
| 2012/0143237 A1 | 6/2012 | Cam |
| 2012/0165919 A1 | 6/2012 | Cox et al. |
| 2012/0197283 A1 | 8/2012 | Marchand et al. |
| 2012/0271337 A1 | 10/2012 | Figulla et al. |
| 2012/0283768 A1 | 11/2012 | Cox et al. |
| 2012/0330341 A1 | 12/2012 | Becking et al. |
| 2013/0066357 A1 | 3/2013 | Aboytes et al. |
| 2013/0092012 A1 | 4/2013 | Marchand et al. |
| 2013/0116722 A1 | 5/2013 | Aboytes et al. |
| 2013/0123830 A1 | 5/2013 | Becking et al. |
| 2013/0211495 A1 | 8/2013 | Halden et al. |
| 2013/0233160 A1 | 9/2013 | Marchand et al. |
| 2013/0239790 A1 | 9/2013 | Thompson et al. |
| 2013/0245667 A1 | 9/2013 | Marchand et al. |
| 2013/0268053 A1 | 10/2013 | Molaei et al. |
| 2013/0274862 A1 | 10/2013 | Cox et al. |
| 2013/0274863 A1 | 10/2013 | Cox et al. |
| 2013/0274866 A1 | 10/2013 | Cox et al. |
| 2013/0274868 A1 | 10/2013 | Cox et al. |
| 2013/0296912 A1 | 11/2013 | Ottma |
| 2013/0325051 A1 | 12/2013 | Martin et al. |
| 2014/0005713 A1 | 1/2014 | Bowman et al. |
| 2014/0005714 A1 | 1/2014 | Quick et al. |
| 2014/0018841 A1 | 1/2014 | Peiffer et al. |
| 2014/0052233 A1 | 2/2014 | Cox et al. |
| 2014/0058436 A1 | 2/2014 | Rosenbluth et al. |
| 2014/0074151 A1 | 3/2014 | Tischler et al. |
| 2014/0135734 A1 | 5/2014 | Dakin et al. |
| 2014/0135817 A1 | 5/2014 | Tischler et al. |
| 2014/0135827 A1 | 5/2014 | Amplatz et al. |
| 2014/0142611 A1 | 5/2014 | Plaza et al. |
| 2014/0172001 A1 | 6/2014 | Becking et al. |
| 2014/0200607 A1 | 7/2014 | Sepetka et al. |
| 2014/0257361 A1 | 9/2014 | Prom |
| 2014/0318354 A1 | 10/2014 | Thompson et al. |
| 2014/0318355 A1 | 10/2014 | Marchand et al. |
| 2014/0330299 A1 | 11/2014 | Rosenbluth et al. |
| 2014/0358178 A1 | 12/2014 | Hewitt et al. |
| 2015/0012033 A1 | 1/2015 | Plaza et al. |
| 2015/0133989 A1 | 5/2015 | Lubock et al. |
| 2015/0182674 A1 | 7/2015 | Schaffer |
| 2015/0272589 A1 | 10/2015 | Lorenzo |
| 2015/0283363 A1 | 10/2015 | Hewitt et al. |
| 2015/0374483 A1 | 12/2015 | Janardhan et al. |
| 2016/0015396 A1 | 1/2016 | Cox et al. |
| 2016/0015398 A1 | 1/2016 | Hewitt et al. |
| 2016/0030052 A1 | 2/2016 | Cragg et al. |
| 2016/0045201 A1 | 2/2016 | Rosenbluth et al. |
| 2016/0100842 A1 | 4/2016 | Plaza et al. |
| 2016/0192941 A1 | 7/2016 | Hewitt et al. |
| 2016/0249934 A1 | 9/2016 | Hewitt et al. |
| 2016/0249935 A1 | 9/2016 | Hewitt et al. |
| 2016/0249937 A1 | 9/2016 | Marchand et al. |
| 2016/0262769 A1 | 9/2016 | Cragg et al. |
| 2016/0324528 A1 | 11/2016 | Hebert et al. |
| 2016/0324668 A1 | 11/2016 | Wallace et al. |
| 2016/0335757 A1 | 11/2016 | Florent et al. |
| 2016/0367260 A9 | 12/2016 | Hewitt et al. |
| 2017/0035437 A1 | 2/2017 | Sarge et al. |
| 2017/0079662 A1 | 3/2017 | Rhee et al. |
| 2017/0095254 A1 | 4/2017 | Hewitt et al. |
| 2017/0128077 A1 | 5/2017 | Hewitt et al. |
| 2017/0224350 A1 | 8/2017 | Shimizu et al. |
| 2017/0245862 A1 | 8/2017 | Cox et al. |
| 2017/0258473 A1 | 9/2017 | Plaza et al. |
| 2018/0000489 A1 | 1/2018 | Marchand et al. |
| 2018/0070955 A1 | 3/2018 | Greene, Jr. et al. |
| 2018/0140305 A1 | 5/2018 | Connor |
| 2018/0153554 A1 | 6/2018 | Walzman |
| 2018/0185130 A1 | 7/2018 | Janardhan et al. |
| 2018/0206849 A1 | 7/2018 | Hewitt et al. |

(56) References Cited

U.S. PATENT DOCUMENTS

| | | |
|---|---|---|
| 2018/0206851 A1 | 7/2018 | Walzman |
| 2018/0271540 A1 | 9/2018 | Merritt et al. |
| 2018/0303486 A1 | 10/2018 | Rosenbluth et al. |
| 2018/0338767 A1 | 11/2018 | Dasnurkar et al. |
| 2019/0046209 A1 | 2/2019 | Plaza et al. |
| 2019/0192166 A1 | 6/2019 | Hewitt et al. |
| 2019/0192167 A1 | 6/2019 | Lorenzo |
| 2019/0209180 A1 | 7/2019 | Kealey et al. |
| 2019/0218696 A1 | 7/2019 | Thompson et al. |
| 2019/0223881 A1 | 7/2019 | Hewitt et al. |
| 2019/0269414 A1 | 9/2019 | Griffin |
| 2019/0298364 A1 | 10/2019 | Walsh et al. |
| 2019/0343533 A1 | 11/2019 | Costalat |
| 2019/0365385 A1 | 12/2019 | Gorochow et al. |
| 2020/0113576 A1 | 4/2020 | Gorochow et al. |
| 2020/0289124 A1 | 9/2020 | Rangwala et al. |
| 2020/0289125 A1 | 9/2020 | Dholakia et al. |
| 2020/0289126 A1 | 9/2020 | Hewitt et al. |
| 2021/0007754 A1 | 1/2021 | Milhous et al. |
| 2021/0153871 A1 | 5/2021 | Griffin |
| 2022/0257260 A1 | 8/2022 | Hewitt et al. |

FOREIGN PATENT DOCUMENTS

| | | |
|---|---|---|
| CN | 106974691 | 7/2017 |
| EP | 0706876 | 7/2000 |
| EP | 0808138 | 5/2005 |
| EP | 1576929 | 9/2005 |
| EP | 1844717 | 10/2007 |
| EP | 1923019 | 5/2008 |
| EP | 2055263 | 6/2009 |
| EP | 2258275 | 12/2011 |
| EP | 2596754 A1 | 5/2013 |
| EP | 2157937 | 3/2017 |
| FR | 2333169 | 6/1997 |
| JP | 52141092 | 11/1977 |
| JP | H4-47415 | 4/1992 |
| WO | WO 95/30384 | 11/1995 |
| WO | WO 96/01591 | 1/1996 |
| WO | WO 97/26939 | 7/1997 |
| WO | WO 99/03404 | 1/1999 |
| WO | WO 99/05977 | 2/1999 |
| WO | WO 99/62432 | 12/1999 |
| WO | WO 01/45571 | 6/2001 |
| WO | WO 01/93782 | 12/2001 |
| WO | WO 02/00139 | 1/2002 |
| WO | WO 03/011151 | 2/2003 |
| WO | WO 03/032818 | 4/2003 |
| WO | WO 03/063732 | 8/2003 |
| WO | WO 2004/047649 | 6/2004 |
| WO | WO 2004/093742 | 11/2004 |
| WO | WO 2005/117718 | 12/2005 |
| WO | WO 2006/026744 | 3/2006 |
| WO | WO 2006/055683 | 5/2006 |
| WO | WO 2007/006139 | 1/2007 |
| WO | WO 2007/096183 | 8/2007 |
| WO | WO 2008/151204 | 12/2008 |
| WO | WO 2009/036219 | 3/2009 |
| WO | WO 2009/048700 A1 | 4/2009 |
| WO | WO 2009/121006 | 10/2009 |
| WO | WO 2009/126747 | 10/2009 |
| WO | WO 2009/132045 | 10/2009 |
| WO | WO 2009/134337 | 11/2009 |
| WO | WO 2009/135166 | 11/2009 |
| WO | WO 2010/134914 | 11/2010 |
| WO | WO 2011/057002 | 5/2011 |
| WO | WO 2013/102848 | 7/2013 |
| WO | WO 2013/119332 A2 | 8/2013 |
| WO | WO 2014/087245 | 6/2014 |
| WO | WO 2014/169261 | 10/2014 |
| WO | WO 2015/160721 | 10/2015 |
| WO | WO 2015/171268 | 11/2015 |
| WO | WO 2015/192019 | 12/2015 |
| WO | WO 2017/153603 | 9/2017 |
| WO | WO 2018/051187 | 3/2018 |
| WO | WO 2018/058033 A1 | 3/2018 |
| WO | WO 2019/040494 | 2/2019 |

OTHER PUBLICATIONS

Allen et al., "Micromachine Wedge Stepping Motor," pp. 1-6, Nov. 12-20, 1998 ASME International Mechanical Engineering Congress, Anaheim, CA.

Altes et al., "Creation of Saccular Aneurysms in the Rabbit: A model Suitable for Testing Endovascular Devices," American Roentgen Ray Society, Feb. 2000.

Ansari et al., "Thrombosis of a Fusiform Intracranial Aneurysm Induced by Overlapping Neuroform Stents: Case Report," *Neurosurgery*, E950-E951 vol. 60, No. 5, May 2007.

Atritech Press Release, Minneapolis, Jun. 18, 2007 "Atritech Announces Intellectual Property Acquisition, Transaction Establishes Company as leader in Left Atrial Appendage Market."

Caroff, J. et al., "Woven Endobridge (WEB) Device for endovascular treatment of ruptured intracranial wide-neck aneurysms: a single-center experience," *Neuroradiology*, 56(9):755-761 (Sep. 2014).

Caroff, J. et al., "Role of C—Arm VasoCT in the Use of Endovascular WEB Flow Disruption in Intracranial Aneurysm Treatment," *AJNR Am. J. Neuroradiol.* 35(7):1353-1357 (Jul. 2014).

Colla, R. et al., "Treatment of Wide-Neck Basilar Tip Aneurysms Using the Web II Device," *The Neuroradiology Journal* 26(6):669-677 (Dec. 2013).

De Backer, O. et al., "Percutaneous left atrial appendage occlusion for stroke prevention in atrial fibrillation: an update," *Open Heart*, 4:1-14 (2013).

Ding, Y.H. et al., "The Woven EndoBridge: A New Aneurysm Occlusion Device," *AJNR Am. J. Neruradiol.* 32:607-611 (Mar. 2011).

Duerig, T.W., "The Use of Superelasticity in Modern Medicine," MRS Bulletin, pp. 101-104 (Feb. 2002).

Fiorella, D. et al., "Interobserver variability in the assessment of aneurysm occlusion with the WEB aneurysm embolization system," *J. NeuroIntervent. Surg.* Jul. 1, 2014, pii: neurintsurg-2014-011251. doi: 10.1136/neurintsurg-2014-011251 [Epub ahead of print].

Fort Wayne Metals HHS Tube brochure, p. 28-29 (2009), Fort Wayne, Indiana, www.oldsite.fwmetals.com.

Grabenwoger et al., "Endothelialization of Biosynthetic vascular Prosthesis After Laser Perforation," *Ann Thorac Surg*, 66:S110-S114 (1998).

Guider Softip XF Guide Catheters Brochure, Boston Scientific Corporation 2004.

Gupta et al., "Nitinol Thin Film Three Dimensional Devices-Fabrication and Applications," From: SMST-2003: Proceedings of the International Conference on Shape Memory and Superelastic Technologies Published: 2004.

Hill et al., "Initial Results of the AMPLATZER® Vascular Plug in the treatment of Congenital Heart Disease," Technology and Services, *Business Briefing: US Cardiology*, pp. 1-3 (2004).

Jeffree et al., "The Porus, Guidewire-Directed, Detachable Aneurysm Liner: A New Concept in the Endovascular Treatment of Intracranial Aneurysms," *AJNR Am J Neuradiol* 20:774-779 (May 1999).

Kallmes et al., "A New Endoluminal, Flow-Disrupting Device for Treatment of Saccular Eneurysms," *Stroke*, Journal of the American Heart Association 38:1-7 (2007).

Klisch, J. et al., "The Woven EndoBridge Cerebral Aneurysm Embolization Device (Web II): initial clinical experience," *Neuroradiology* 53:599-607 (2011).

Kónya, A. et al., "Preliminary Results with a New Vascular Basket Occluder in Swine," *JVIR*, 10(8):1043-1049 (1999).

Kwon et al., "Preliminary Results of the Luna Aneurysm Embolization System in a Rabbit Model: A New Intrasaccular Aneurysm Occlusion Device," *AJNR Am J Neuroradiol*, 32:602-606 (Mar. 2011).

Lendlein, A. et al., "Shape-Memory Polymers," *Angew. Chem. Int. Ed.*, 41:2034-2057 (2002).

(56) References Cited

OTHER PUBLICATIONS

Lendlein, A. et al., "Biodegradable, Elastic Shape-Memory Polymers for Potential Biomedical Applications," *Science* 296:1673-1676 (May 31, 2002).
Lieber, B.B. et al., "The Role of Blood Impulse in Cerebral Aneurysm Coil Compaction: Effect of Aneurysm Neck Size," IMECE2003-43099, Proceedings of IMECE '03, 2003 ASME International Mechanical Engineering Congress, Washington, D.C. (Nov. 15-21, 2003).
Liu, C. et al., "Review of progress in shape-memory polymers," *J. Mater. Chem.* 17:1543-1558 (2007).
Lubicz, B. et al., "WEB Device for Endovascular Treatment of Wide-Neck Bifurcation Aneurysms," *AJNR Am. J. Neuroradiol.* 34(6):1209-1214 (Jun-Jul. 2013).
Lubicz, B. et al., "WEB-DL Endovascular Treatment of Wide-Neck Bifurcation Aneurysms: Short- and Midterm Results in a European Study," *AJNR Am. J. Neuroradiol.* 35(3):432-438 (Mar. 2014). doi: 10.3174/ajnr.A3869. Epub Jan. 23, 2014.
Major, S. et al., "Life of Nitinol Drawn Filed Wires with Ag or Au Core for Medical Application," *International Journal of Mechanics* 2(7):73-80 (2013).
Matinlinna et al., "An Introduction to Silanes and Their Clinical Applications in Dentistry," *The International Journal of Prosthodontics*, 17(2):155-164 (2004).
Mine et al., "Intrasaccular flow-diversion for treatment of intracranial aneurysms: the Woven EndoBridge," *Expert Rev. Med. Devices* 11(3):315-325 (May 2014). doi: 10.1586/17434440.2014.907741. Epub Apr. 2, 2014.
Nakayama et al., "Development of Microporous Covered Stents: Geometrical Design of the Luminal Surface," *The International Journal of Artificial Organs*, 28(6):600-608 (2005).
Nemat-Nasser, S. et al., "Superelastic and cyclic response of NiTi SMA at various strain rates and temperatures," *Mechanics of Materials* 38:463-474 (2006).
Nishi et al., "Embolization of experimental aneurysms using a heparin-loaded stent graft with micropores," *Cardiovascular Radiation Medicine* 4:29-33 (2003).
Nishi et al., "Occlusion of Experimental Aneurysms with Heparin-Loaded, Microporous Stent Grafts," *Neurosurgery* 53(6):1397-1405 (Dec. 2003).
Papagiannaki, C. et al., "WEB Intrasaccular Flow Disruptor—Prospective, Multicenter Experience in 83 Patients with 85 Aneurysms," *AJNR Am. J. Neuroradiol.* 35(11):2106-2111 (Nov.-Dec. 2014). 35(11):2106-11. doi: 10.3174/ajnr.A4028. Epub Jul. 3, 2014.
Park, J. et al., "Percutaneous Left Atrial Appendage Transcatheter Occlusion (PLAATO) for Stroke Prevention in Atrial Fibrillation: 2-Year Outcome," *J Invasive. Cardiol.*, 21(9):446-450 (2009).
Pelton, A.R. et al., "Optimisation of processing and properties of medical grade Nitinol wire," *Min. Invas. Ther. & Allied Technol.* 9(1):107-118 (2000).
Pham, Q. et al., "Electrospinning of Polymeric Nanofibers for Tissue Engineering Applications: A Review," *Tissue Engr* 12(5):1197-1211 (1996).
Pierot, L. et al., "Intrasaccular Flow-Disruption Treatment of Intracranial Aneurysms: Preliminary Results of a Multicenter Clinical Study," *AJNR Am J Neuroradiol.* 33(7):1232-1238 (Aug. 2012). doi: 10.3174/ajnr.A3191. Epub Jun. 7, 2012.
Pierot, L. et al., "Endovascular WEB Flow Disruption in Middle Cerebral Artery Aneurysms: Preliminary Feasibility, Clinical, and Anatomical Results in a Multicenter Study," *Neurosurgery* 73(1):27-35 (Jul. 2013).
Pierot, L. et al., "Role, safety, and efficacy of WEB flow disruption: a review," *EJMINT Invited Review*, 2014: 1419000139 (May 8, 2014).
Peirot, L. et al., "WEB Treatment of Intracranial Aneurysms: Feasiblity, Complications, and 1-Month Safety Results with the WEB DL and WEB SL/SLS in the French Observatory," *AJNR Am J Neuroradiol.* Feb. 5, 2015 [Epub ehead ofprint].
Romero, J. et al., "Left Atrial Appendage Closure Devices," *Clinical Medicine Insights: Cardiology*, 8:45-52 (2014).
Rottiers, W. et al., "Shape Memory Materials and their applications," in Korolev's readings: conference proceedings, pp. 250-250 (2011).
Salamat et al., "Experimental Evaluation of a New Transcatheter Vascular Embolization Device in the Swine Model," *J Vasc Interv Radiol*, 12:301-311 (2002).
Schaffer, J.E. et al., "Engineering Characteristics of Drawn Filled Nitinol Tube," SMST-2003: Proceedings of the International Conference on Shape Memory and Superelastic Technologies (ASM International), pp. 109-118 (2004).
Schmitz-Rode, T. et al., "Self-expandable spindle for transcatheter vascular occlusion: in vivo experiments. Work in progress." *Radiology* 188:95-100 (Jul. 1993).
Simgen, A. et al., "Evaluation of a newly designed flow diverter for the treatment of intracranial aneurysms in an elastase-induced aneurysm model, in New Zealand white rabbits," *Neuroradiology* 56:129-137 (2014).
Spelle, L. et al., "Letter to the Editor," *Neuroradiol J.* Jun. 2014; 27(3):369. doi: 10.15274/NRJ-2014-10048. Epub Jun. 17, 2014.
Spelle, L. et al., "CLinical Assessment of WEB device in Ruptured aneurYSms (CLARYS): 12-month angiographic results of a multicenter study", *J NeuroIntervent Surg*, 2022, 0:1-6.
Stoeckel, D. et al., "Self-expanding nitinol stents: material and design considerations," *Eur. Radiol.* 14:292-301 (2004).
Turk, A. et al., "Evaluation of the TriSpan Neck Bridge Device for the Treatment of Wide-Necked Aneurysms: An Experimental Study in Canines, Editorial Comment: An Experimental Study in Canines," *Stroke* 32:492-497 (Feb. 2001).
Wallner, A.K. et al., "Coiling after Treatment with the Woven EndoBridge Cerebral Aneurysm Embolization Device," *Interventional Neuroradiology* 18:208-212 (2012).
Yeow, W.L. et al., Device- and LAA-Specific Characteristics for Successful LAA Closures: Tips and Tricks, *Intervent. Cardiol. Clin.*, 3:239-254 (2014).
Zimmermann et al., "Patent Foramen Oval Closure With the SeptRx Device, Initial Experience with the First "In-Tunnel" Device," *JACC Cardiovascular Interventions* vol. 3, No. 9., 2010.
International Search Report and Written Opinion mailed Oct. 31, 2008 for International Application No. PCT/US2008/065694.
International Search Report and Written Opinion mailed Nov. 26, 2009 for International Application No. PCT/US2009/042592.
International Search Report and Written Opinion mailed Jul. 28, 2011 for International Application No. PCT/US2010/055494.
International Search Report and Written Opinion mailed Jul. 21, 2015 for International Application No. PCT/US2015/025609.
International Search Report and Written Opinion mailed Jan. 11, 2016 for International Application No. PCT/US2015/025613.
International Search Report and Written Opinion mailed Jun. 10, 2020 for International Application No. PCT/US2020/022275.
International Search Report and Written Opinion mailed Jun. 11, 2020 for International Application No. PCT/US2020/022364.
International Search Report and Written Opinion mailed Jun. 15, 2020 for International Application No. PCT/US2020/022319.
International Search Report and Written Opinion mailed Jul. 24, 2020 for International Application No. PCT/US2020/022096.
Extended European Search Report dated Apr. 25, 2014, in EP Appl No. EP 08770070.4 filed Jun. 3, 2008.
Extended European Search Report dated Jul. 30, 2014, in EP Appl No. EP 10829110 filed Nov. 4, 2010.
Extended European Search Report dated Dec. 13, 2017, in EP Appl No. EP 15789225.8 filed Jun. 5, 2015.
Official Action dated Mar. 8, 2019, in JP Appl. No. 2016-562549 filed Jun. 5, 2015.
JP, 2022-141336 Office Action, Feb. 20, 2024.

\* cited by examiner

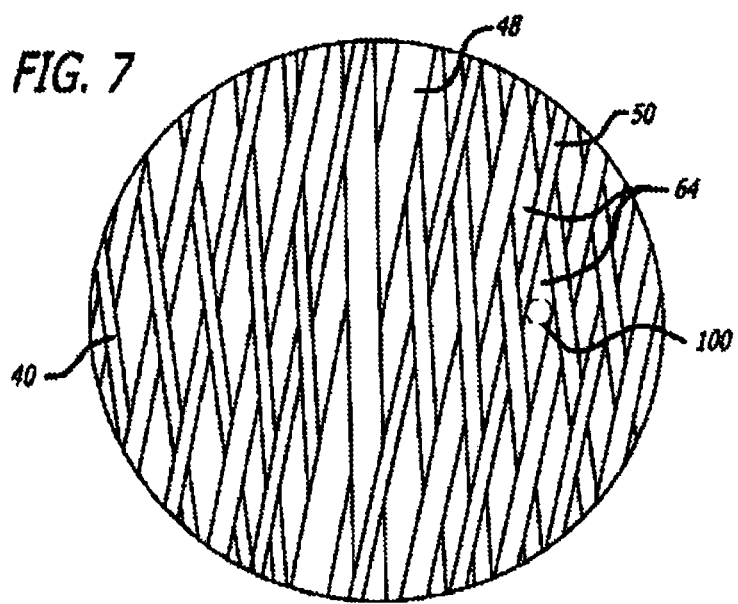
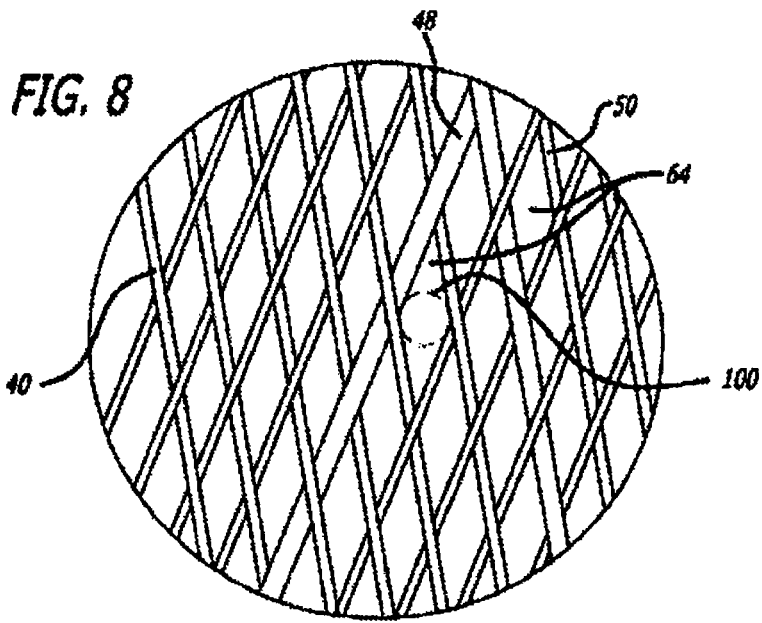

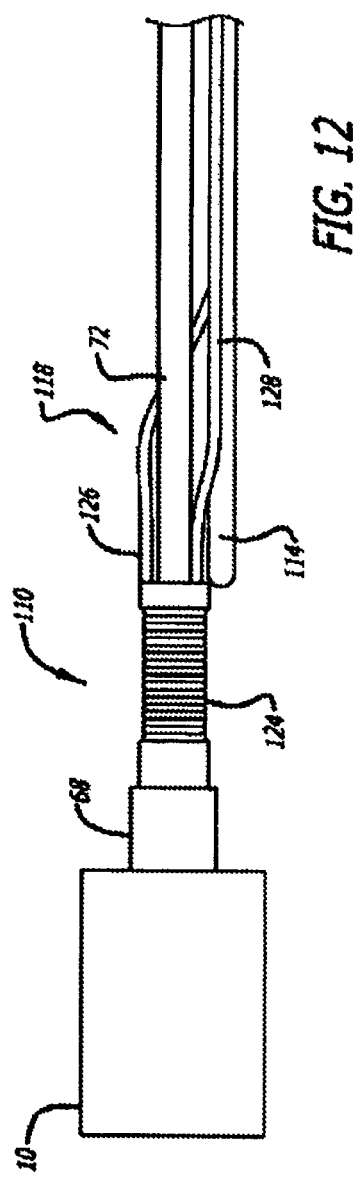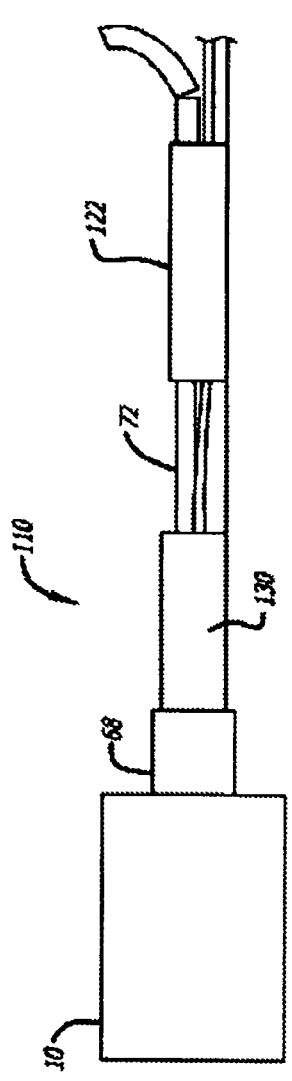

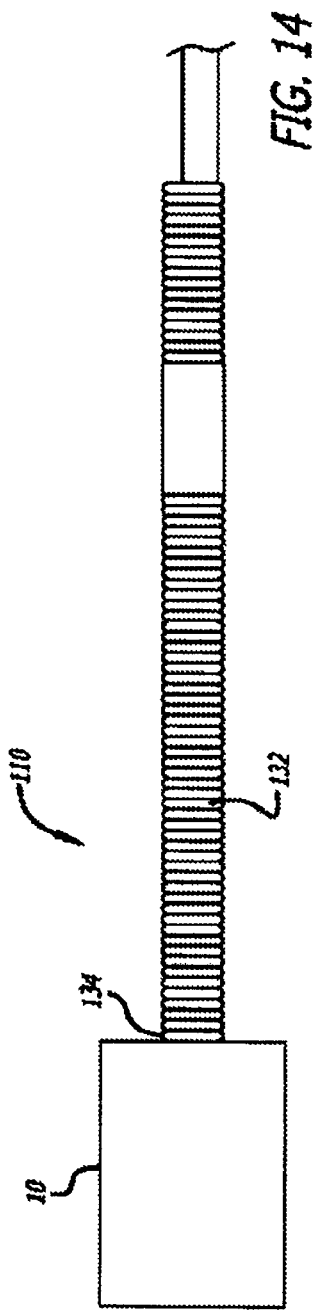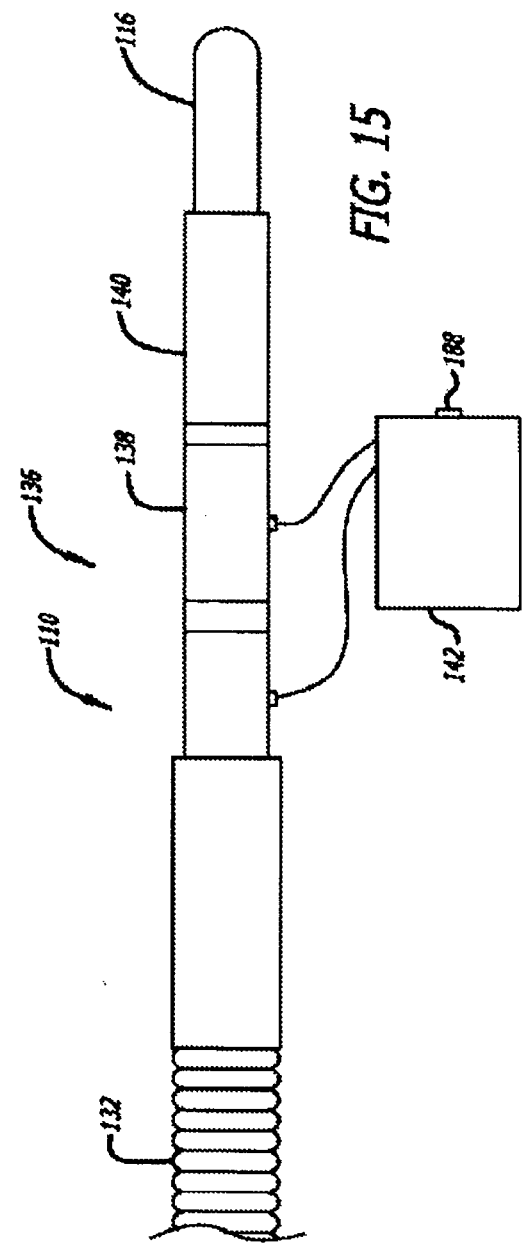

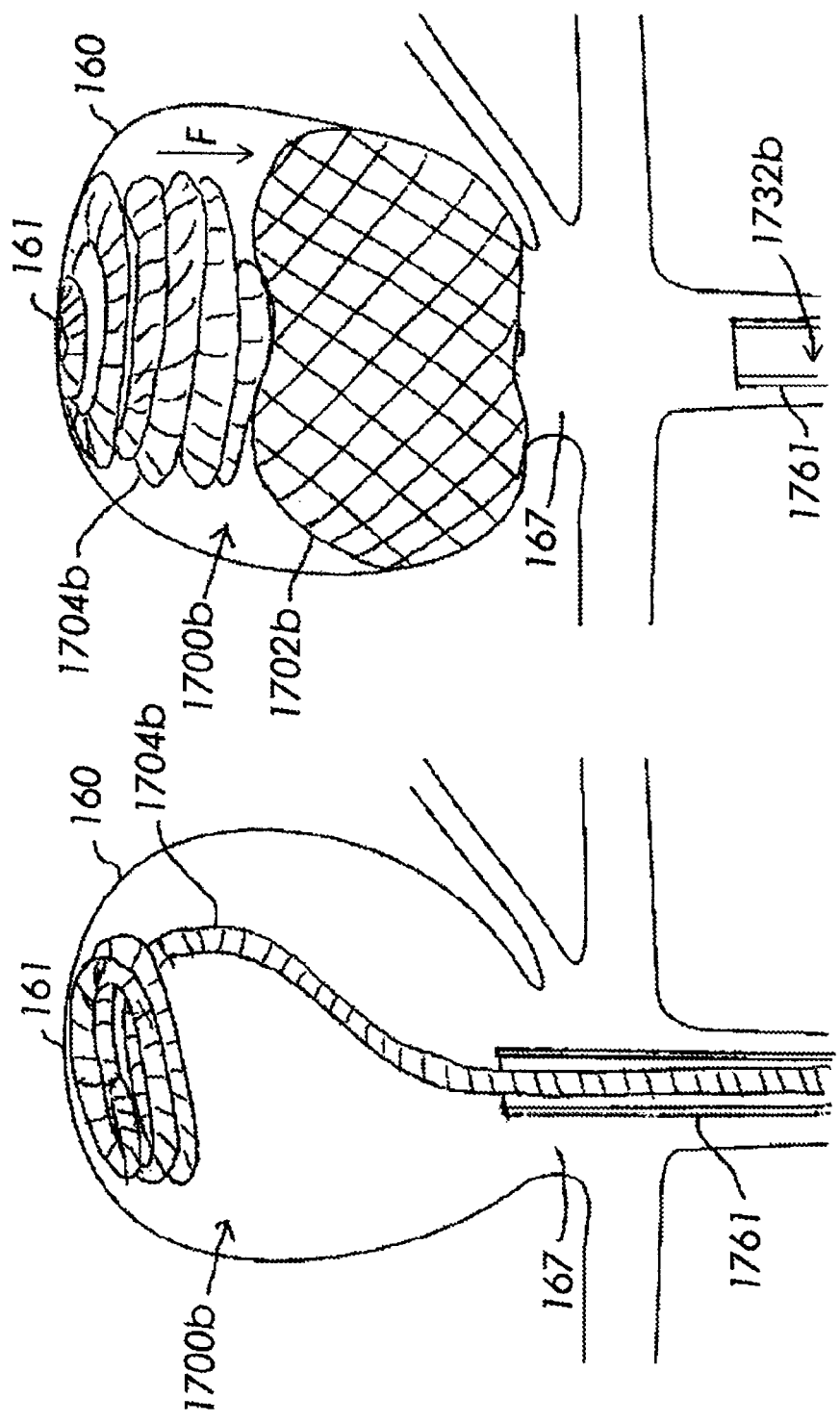

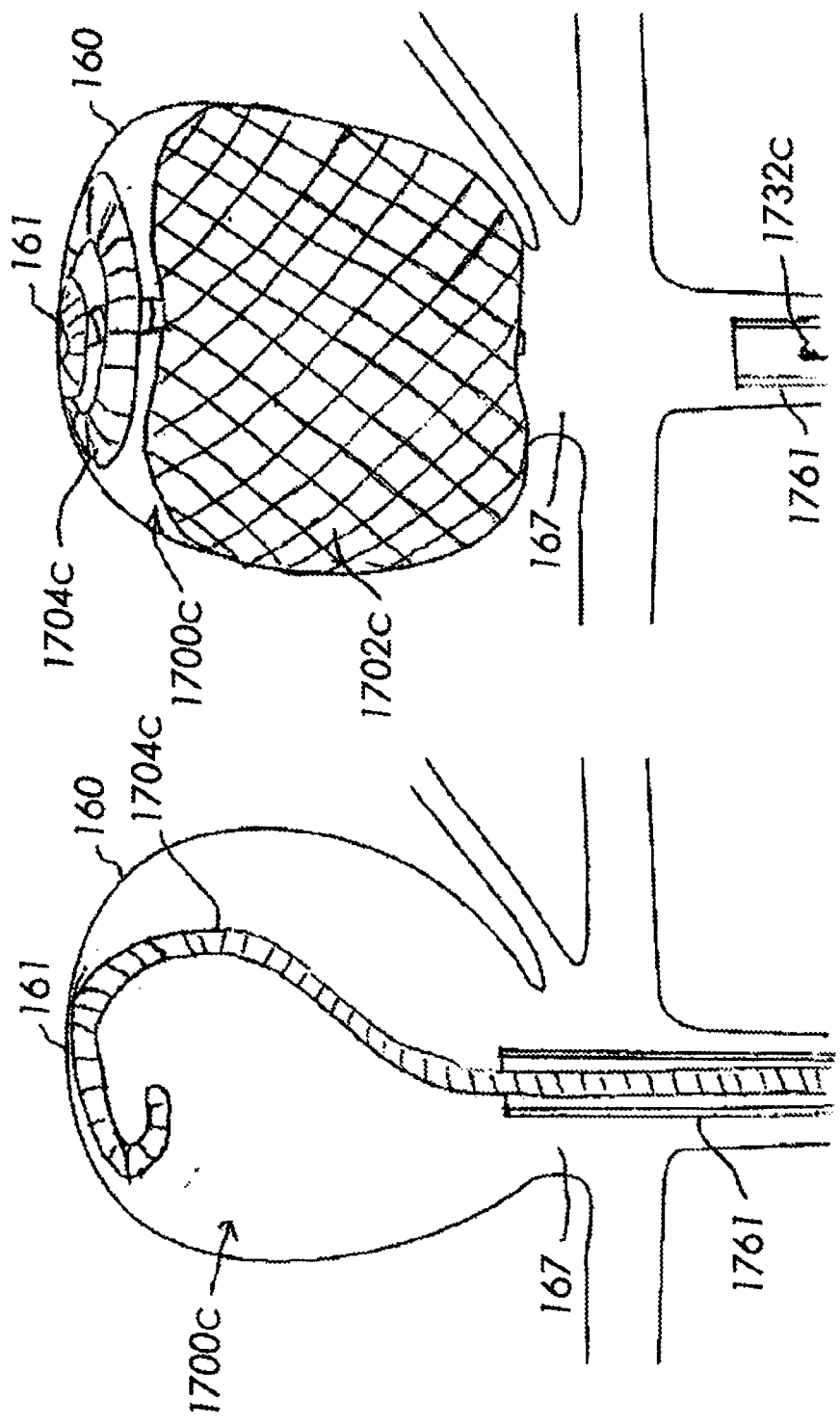

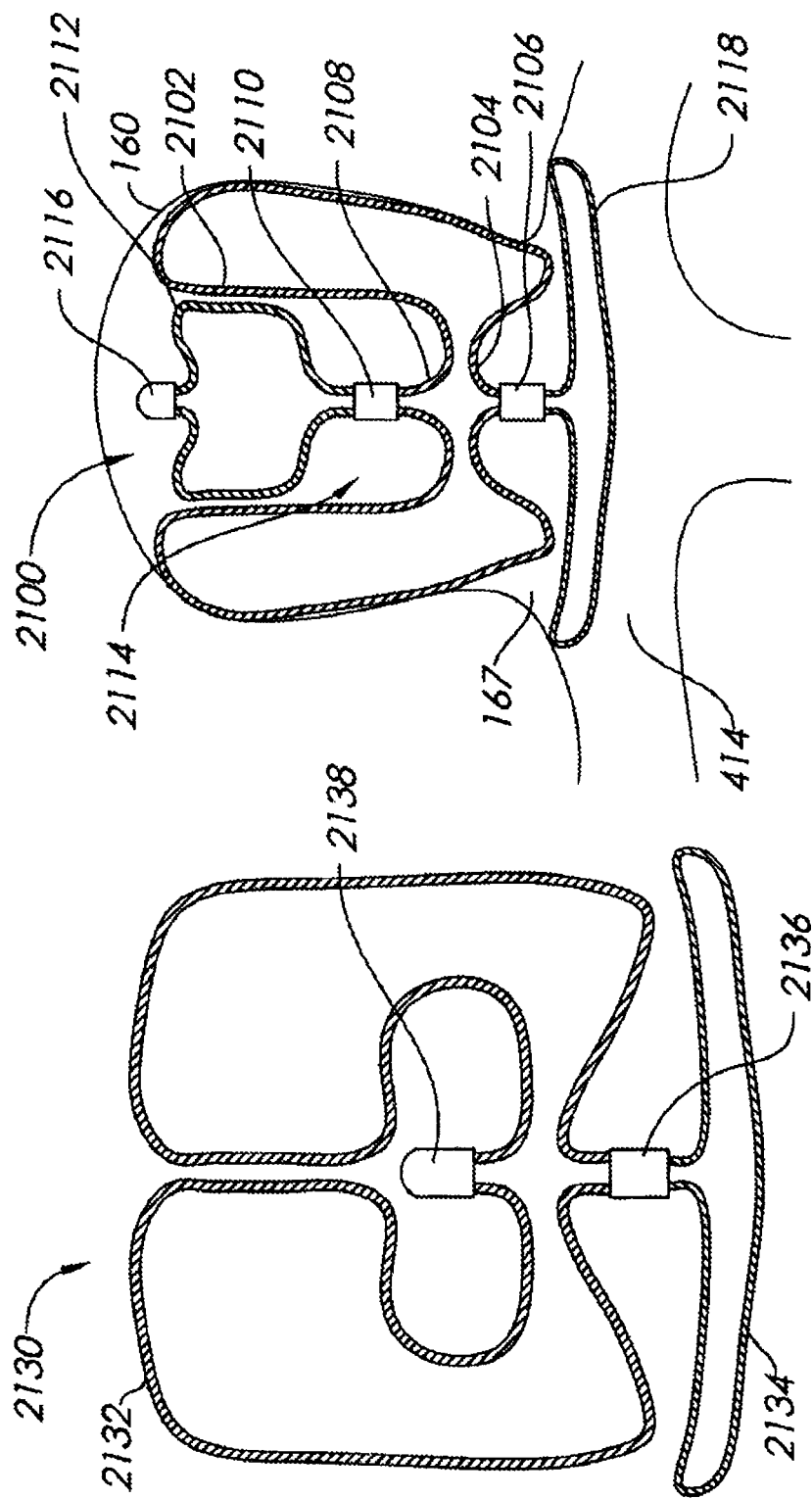

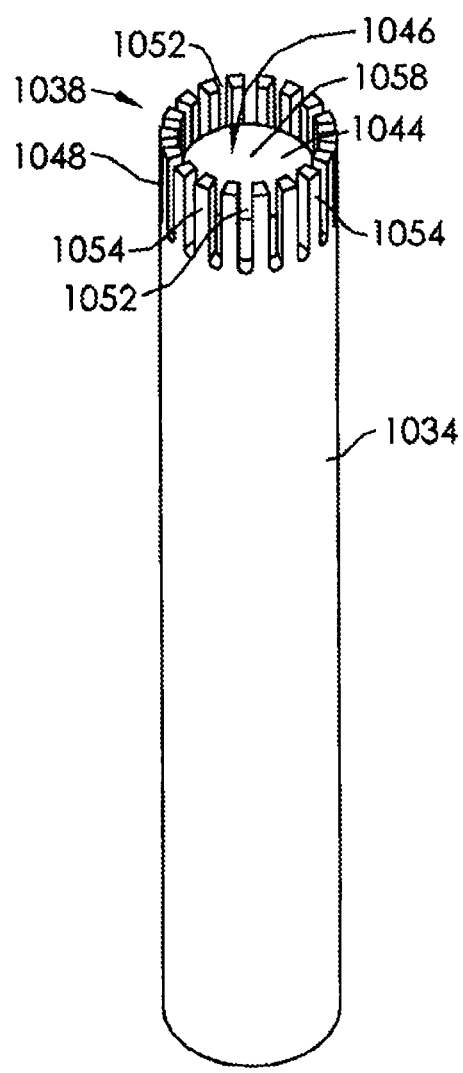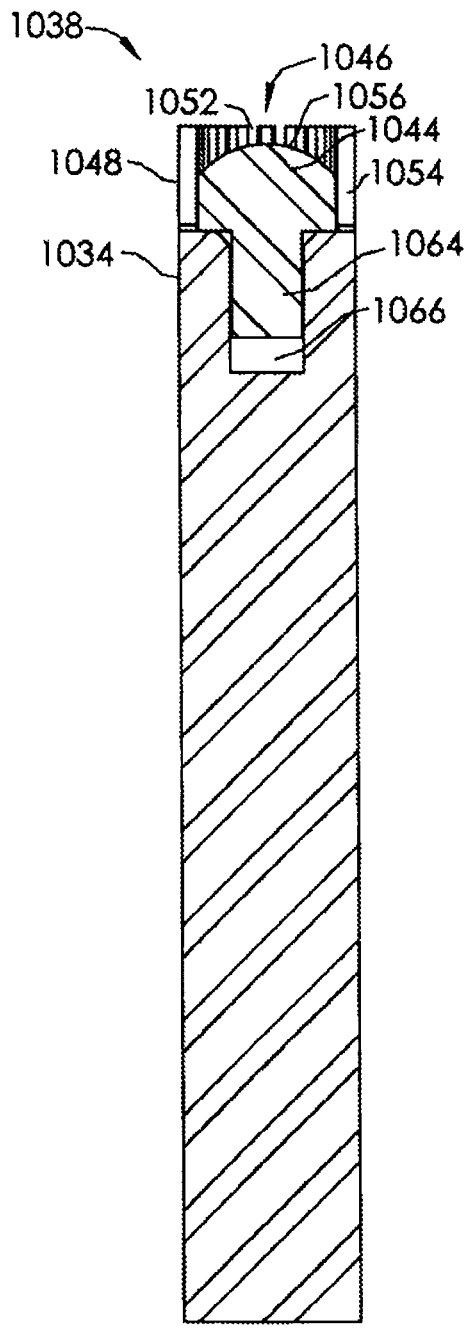
*FIG. 41*  *FIG. 42*

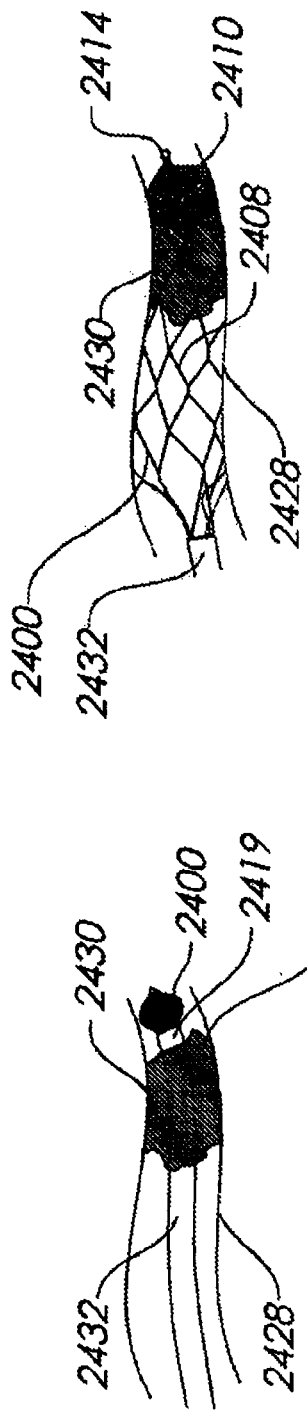
FIG. 64
FIG. 65
FIG. 66
FIG. 67

DEVICES FOR THERAPEUTIC VASCULAR PROCEDURES

RELATED APPLICATIONS

This application is a continuation of U.S. application Ser. No. 16/373,476, filed Apr. 2, 2019, which is a continuation of U.S. application Ser. No. 15/404,492, filed Jan. 12, 2017, now abandoned, which is a continuation of U.S. application Ser. No. 14/684,212, filed Apr. 10, 2015, now issued as U.S. Pat. No. 9,629,635, which claims priority to U.S. Provisional Application Ser. No. 62/093,313, filed Dec. 17, 2014, and U.S. Provisional Application Ser. No. 61/979,416, filed Apr. 14, 2014, all of which are herein incorporated by reference in their entireties for all purposes.

FIELD OF THE INVENTION

Embodiments of devices and methods herein are directed to blocking a flow of fluid through a tubular vessel or into a small interior chamber of a saccular cavity or vascular defect within a mammalian body. More specifically, embodiments herein are directed to devices and methods for treatment of a vascular defect of a patient including some embodiments directed specifically to the treatment of cerebral aneurysms of patients.

BACKGROUND

The mammalian circulatory system is comprised of a heart, which acts as a pump, and a system of blood vessels that transport the blood to various points in the body. Due to the force exerted by the flowing blood on the blood vessel the blood vessels may develop a variety of vascular defects. One common vascular defect known as an aneurysm results from the abnormal widening of the blood vessel. Typically, vascular aneurysms are formed as a result of the weakening of the wall of a blood vessel and subsequent ballooning and expansion of the vessel wall. If, for example, an aneurysm is present within an artery of the brain, and the aneurysm should burst with resulting cranial hemorrhaging, death could occur.

Surgical techniques for the treatment of cerebral aneurysms typically involve a craniotomy requiring creation of an opening in the skull of the patient through which the surgeon can insert instruments to operate directly on the patient's brain. For some surgical approaches, the brain must be retracted to expose the parent blood vessel from which the aneurysm arises. Once access to the aneurysm is gained, the surgeon places a clip across the neck of the aneurysm thereby preventing arterial blood from entering the aneurysm. Upon correct placement of the clip the aneurysm will be obliterated in a matter of minutes. Surgical techniques may be effective treatment for many aneurysms. Unfortunately, surgical techniques for treating these types of conditions include major invasive surgical procedures that often require extended periods of time under anesthesia involving high risk to the patient. Such procedures thus require that the patient be in generally good physical condition in order to be a candidate for such procedures.

Various alternative and less invasive procedures have been used to treat cerebral aneurysms without resorting to major surgery. Some such procedures involve the delivery of embolic or filling materials into an aneurysm. The delivery of such vaso-occlusion devices or materials may be used to promote hemostasis or fill an aneurysm cavity entirely. Vaso-occlusion devices may be placed within the vasculature of the human body, typically via a catheter, either to block the flow of blood through a vessel with an aneurysm through the formation of an embolus or to form such an embolus within an aneurysm stemming from the vessel. A variety of implantable, coil-type vaso-occlusion devices are known. The coils of such devices may themselves be formed into a secondary coil shape, or any of a variety of more complex secondary shapes. Vaso-occlusive coils are commonly used to treat cerebral aneurysms but suffer from several limitations including poor packing density, compaction due to hydrodynamic pressure from blood flow, poor stability in wide-necked aneurysms and complexity and difficulty in the deployment thereof as most aneurysm treatments with this approach require the deployment of multiple coils.

Another approach to treating aneurysms without the need for invasive surgery involves the placement of sleeves or stents into the vessel and across the region where the aneurysm occurs. Such devices maintain blood flow through the vessel while reducing blood pressure applied to the interior of the aneurysm. Certain types of stents are expanded to the proper size by inflating a balloon catheter, referred to as balloon expandable stents, while other stents are designed to elastically expand in a self-expanding manner. Some stents are covered typically with a sleeve of polymeric material called a graft to form a stent-graft. Stents and stent-grafts are generally delivered to a preselected position adjacent a vascular defect through a delivery catheter. In the treatment of cerebral aneurysms, covered stents or stent-grafts have seen very limited use due to the likelihood of inadvertent occlusion of small perforator vessels that may be near the vascular defect being treated.

In addition, current uncovered stents are generally not sufficient as a stand-alone treatment. In order for stents to fit through the microcatheters used in small cerebral blood vessels, their density is usually reduced such that when expanded there is only a small amount of stent structure bridging the aneurysm neck. Thus, they do not block enough flow to cause clotting of the blood in the aneurysm and are thus generally used in combination with vaso-occlusive devices, such as the coils discussed above, to achieve aneurysm occlusion.

A number of aneurysm neck bridging devices with defect spanning portions or regions have been attempted; however, none of these devices has had a significant measure of clinical success or usage. A major limitation in their adoption and clinical usefulness is the inability to position the defect spanning portion to assure coverage of the neck. Existing stent delivery systems that are neurovascular compatible (i.e., deliverable through a microcatheter and highly flexible) do not have the necessary rotational positioning capability. Another limitation of many aneurysm bridging devices described in the prior art is the poor flexibility. Cerebral blood vessels are tortuous and a high degree of flexibility is required for effective delivery to most aneurysm locations in the brain.

What has been needed are devices and methods for delivery and use in small and tortuous blood vessels that can substantially block the flow of blood into an aneurysm, such as a cerebral aneurysm. In addition, what has been needed are methods and devices suitable for blocking blood flow in cerebral aneurysms over an extended period of time without a significant risk of deformation, compaction or dislocation.

SUMMARY

In one embodiment of the invention, a device for removal of thrombus from a blood vessel is described. The device includes an expandable cylindrical structure having a proximal end and a distal end, and being formed from a plurality of wires, wherein adjacent wires are engaged to each other by a plurality of twists. The plurality of wires is secured together at the distal end and the proximal end of the cylindrical structure. The cylindrical structure has a radially constrained state and an expanded relaxed state. The device also includes a self-expanding resilient permeable shell having a proximal end, a distal end, and a longitudinal axis. The self-expanding resilient permeable shell includes a plurality of elongate resilient filaments having a braided structure with a plurality of openings, wherein the plurality of filaments is secured at proximal and distal ends. The self-expanding permeable shell has a radially constrained elongated state and an expanded relaxed state with a globular, axially shortened configuration relative to the radially constrained state. The self-expanding permeable shell is enclosed within the expandable cylindrical structure and positioned at the distal end of the expandable cylindrical structure.

In another embodiment of the invention, a method for removing a thrombus having a proximal and distal end from a blood vessel is described. A thrombus removal device is obtained. The thrombus removal device includes an expandable cylindrical structure having a proximal end, a middle portion, and a distal end. The expandable cylindrical structure is formed from a plurality of wires, wherein adjacent wires are engaged to each other by a plurality of twists, the plurality of wires secured together at distal ends and secured together at proximal ends. The cylindrical structure has a radially constrained state and an expanded relaxed state. The thrombus removal device also includes a self-expanding resilient permeable shell having a proximal end, a distal end, and a longitudinal axis. The self-expanding resilient permeable shell includes a plurality of elongate resilient filaments having a braided structure with a plurality of openings, wherein the plurality of filaments is secured at proximal and distal ends. The self-expanding permeable shell has a radially constrained elongated state and an expanded relaxed state with a globular, axially shortened configuration relative to the radially constrained state. The self-expanding permeable shell is enclosed within the expandable cylindrical structure and positioned at the distal end of the expandable cylindrical structure. The thrombus removal device is slideably positioned within a microcatheter and the microcatheter is inserted into the patient, the expandable cylindrical structure and self-expanding resilient permeable shell both being in the radially constrained state within the microcatheter. The distal end of the microcatheter is positioned adjacent a distal end of the thrombus. The thrombus removal device is deployed from the microcatheter by relative displacement of the thrombus removal device and the microcatheter. Upon deployment, the proximal end of the self-expanding resilient permeable shell located within the expandable cylindrical structure is located distal of the thrombus and the middle portion of the expandable cylindrical structure overlaps the proximal and distal ends of the thrombus, wherein the self-expanding resilient permeable shell and the expandable cylindrical structure moves toward their expanded states once the thrombus removal device is advanced out of the microcatheter. The expandable expanded cylindrical structure with the self-expanding resilient permeable shell at the distal end of the cylindrical structure is then moved in a proximal direction, thereby detaching the thrombus or thrombi from the endoluminal surface of the vessel and capturing the thrombus in the expandable cylindrical structure. The thrombus removal device and the captured thrombus or thrombi are then removed from the blood vessel.

The thrombus removal device and the microcatheter may be removed together from the blood vessel. Alternatively, the thrombus removal device may be removed from the microcatheter and the microcatheter may be left in place in the blood vessel. The thrombus removal device and the microcatheter may be removed together from the patient. Alternatively, the thrombus removal device may be removed from the microcatheter and the microcatheter may be left in place in the patient. The self-expanding permeable shell may have a braid density sufficiently high to maintain the thrombus within the cylindrical structure and also allow blood to flow through the self-expanding permeable shell.

In another embodiment of the invention, a device for treatment of an aneurysm is described. The device includes a distal self-expanding resilient permeable shell having a proximal end, a distal end, and a longitudinal axis. The distal permeable shell includes a plurality of elongate resilient filaments having a braided structure with a plurality of openings formed between the braided filaments. The plurality of filaments is gathered at least at the proximal end thereof. The distal permeable shell has a radially constrained elongated state configured for delivery within a microcatheter and an expanded state with an axially shortened configuration relative to the radially constrained state, wherein the expanded state of the distal permeable shell has a convex shape at the distal end of the distal permeable shell. The device also includes a proximal self-expanding resilient permeable shell having a proximal end, a distal end, and a longitudinal axis. The proximal permeable shell includes a plurality of elongate resilient filaments having a braided structure with a plurality of openings formed between the braided filaments. The plurality of filaments is gathered at least at the proximal end thereof. The proximal permeable shell has a radially constrained elongated state configured for delivery within a microcatheter and an expanded state with an axially shortened configuration relative to the radially constrained state, wherein the expanded state of the proximal permeable shell has a generally convex shape at the proximal end of the proximal permeable shell. The device also includes an elongate support member having a proximal end and a distal end. The elongate support member is positioned between the distal and proximal permeable shells. The expanded states of the distal and proximal permeable shells define a toroidal cavity through which the elongate support member extends.

The average size of the plurality of openings in the distal permeable shell may be larger than an average size of the plurality of openings in the proximal permeable shell. The average size of the plurality of openings in the distal permeable shell may be about 300 µm to about 900 µm, alternatively about 300 µm to about 700 µm, alternatively 300 µm to about 500 µm. The average size of the plurality of openings in the proximal permeable shell may be about 50 µm to about 200 µm, alternatively about 100 µm to about 200 µm, or alternatively about 50 µm to about 150 µm. The braided structure of the distal permeable shell may have a first braid density and the braided structure of the proximal permeable shell may have a second braid density. The first braid density may be greater than the second braid density. The first braid density may be between about 0.10 and 0.20, or alternatively between about 0.10 and 0.15. The second braid density may be between about 0.15 and 0.40, alternatively between about 0.17 and 0.30.

The elongate support member may be rigid or it may be a coil. If the elongate support member is rigid, it may be formed from a hypo tube. If the elongate support member is a coil, it may be an extension spring. At rest, the extension spring is not compressible to a smaller length. The elongate support member may have a length between about 2 mm and about 10 mm, alternatively between about 3 mm and about 8 mm, or alternatively between about 3.5 mm and about 5.5 mm. The extension spring may have a length between about 2 mm and about 10 mm, alternatively between about 3 mm and about 8 mm, and alternatively between about 3.5 mm and about 5.5 mm. The rigid support member may have a length between about 2 mm and about 10 mm, alternatively between about 3 mm and about 8 mm, or alternatively between about 3.5 mm and about 5.5 mm.

The plurality of filaments that make up the distal and proximal permeable shells may include nitinol wires, drawn filled tubes, and mixtures thereof. The plurality of filaments of the distal permeable shell may be gathered at the distal end of the distal permeable shell. Moreover, each of the plurality of filaments of the distal permeable shell has a first end and a second end. The first and second ends of the plurality of filaments of the distal permeable shell may be gathered at the proximal end of the distal permeable shell.

The expanded shape of the distal permeable shell may contact the expanded shape of the proximal permeable shell. The expanded shape of the distal permeable shell and the expanded shape of the proximal permeable shell may also form a substantially globular shape.

In another embodiment of the invention, a method for treating a cerebral aneurysm is described. The method includes the step of providing an implant having a distal self-expanding resilient permeable shell, a proximal self-expanding resilient permeable shell, and an elongate support member positioned between the distal and proximal permeable shells. The distal self-expanding resilient permeable shell has a proximal end, a distal end, and a longitudinal axis, and includes a plurality of elongate resilient filaments having a braided structure with a plurality of openings formed between the braided filaments. The plurality of filaments are gathered at least at the proximal end thereof, wherein the distal permeable shell has a radially constrained elongated state configured for delivery within a microcatheter and an expanded state with an axially shortened configuration relative to the radially constrained state, wherein the expanded state of the distal permeable shell has a convex shape at the distal end of the distal permeable shell.

In one embodiment of the invention, a device for treatment of an aneurysm within a patient's vasculature is described. The device includes a self-expanding resilient permeable shell having a proximal end, a distal end, and a longitudinal axis. The shell is made of a plurality of elongate resilient filaments having a braided structure, wherein the plurality of filaments are secured at least at one of the proximal end or the distal end thereof. The permeable shell has a plurality of openings formed between the braided filaments. The device also includes a metallic coil formed from a wire having a first diameter. The metallic coil is secured at the distal end of the self-expanding resilient permeable shell. The permeable shell has a radially constrained elongated state configured for delivery within a microcatheter and has an expanded state with a globular, axially shortened configuration relative to the radially constrained state. The metallic coil has a linear, straightened shape configured for delivery within a microcatheter and an expanded state having at least one loop having a secondary diameter.

The metallic coil may be configured to place a bias on the permeable shell when the permeable shell is in the expanded state within an aneurysm. When at least partially compressed in an axial direction, the metallic coil can apply an axial bias of at least 0.27 grams, alternatively at least 2.67 grams, alternatively at least 16.6 grams, alternatively between about 0.27 grams and about 40 grams, alternatively between about 2.67 grams and about 30 grams, alternatively between about 16.6 grams and about 20 grams.

In another embodiment of the invention, methods for treating a cerebral aneurysm are described. An implant structure is provided. The implant structure includes a self-expanding resilient permeable shell having a proximal end, a distal end, and a longitudinal axis. The shell includes a plurality of elongate resilient filaments having a braided structure, wherein the plurality of filaments are secured at least at one of the proximal end or the distal end thereof. The implant structure also includes a metallic coil formed from a wire having a first diameter, wherein the metallic coil is secured at the distal end of the self-expanding resilient permeable shell. The permeable shell has a plurality of openings formed between the braided filaments. The device also includes a metallic coil formed from a wire having a first diameter. The metallic coil is secured at the distal end of the self-expanding resilient permeable shell. The permeable shell has a radially constrained elongated state configured for delivery within a microcatheter and has an expanded state with a globular, axially shortened configuration relative to the radially constrained state. The metallic coil has a linear, straightened shape configured for delivery within a microcatheter and an expanded state having at least one loop having a secondary diameter. The implant is advanced within a microcatheter to a region near the cerebral aneurysm. The implant is deployed within the cerebral aneurysm such that the metallic coil is positioned near a dome of the cerebral aneurysm and assumes the expanded state, and the permeable shell assumes the expanded deployed state within the cerebral aneurysm. The microcatheter is then withdrawn from the region near the cerebral aneurysm after the implant is deployed.

Once deployed in the cerebral aneurysm, the metallic coil may push the permeable shell against an opening of the cerebral aneurysm. The metallic coil may track around the diameter of the cerebral aneurysm. The secondary diameter of the metallic coil may approximately equal a diameter of the permeable shell. When at least partially compressed, the metallic coil can apply an axial bias of at least 0.27 grams, alternatively at least 2.67 grams, alternatively at least 16.6 grams, alternatively between about 0.27 grams and about 40 grams, alternatively between about 2.67 grams and about 30 grams, alternatively between about 16.6 grams and about 20 grams.

In another embodiment of the invention, a device for treatment of an aneurysm within a patient's vasculature is described. The device includes a self-expanding resilient permeable shell having a proximal end, a distal end, and a longitudinal axis. The shell is made of a plurality of elongate resilient filaments having a braided structure, wherein the plurality of filaments are secured at least at one of the proximal end or the distal end thereof. The permeable shell has a plurality of openings formed between the braided filaments. The device also includes a force biasing member secured at the distal end of the self-expanding resilient permeable shell. The permeable shell has a radially constrained elongated state configured for delivery within a microcatheter and has an expanded state with a globular, axially shortened configuration relative to the radially constrained state. The force biasing member has a linear, straightened shape configured for delivery within a microcatheter and an expanded state after delivery from the microcatheter.

The force biasing member may be configured to place a bias on the permeable shell when the permeable shell is in the expanded state within an aneurysm. When at least partially compressed in an axial direction, the metallic coil can apply an axial bias of at least 0.27 grams, alternatively at least 2.67 grams, alternatively at least 16.6 grams, alternatively between about 0.27 grams and about 40 grams, alternatively between about 2.67 grams and about 30 grams, alternatively between about 16.6 grams and about 20 grams. The force biasing member may be configured to conform to a three-dimensional framing shape. The force biasing member may be made from wire comprising platinum.

The force biasing member may also have a generally circular shape. The plurality of filaments forming the permeable shell may be secured at the distal end. A distal region of at least some of the plurality of filaments extend beyond the distal end of the permeable shell and form an extension having a generally circular shape, which may be the force biasing member. The plurality of filaments may be secured by a cylindrical hub having a proximal and distal end, and the extension may extend from the distal end of the cylindrical hub. The distal regions of filaments forming the extension may be straight or braided or partially braided, or the braid may be partially undone or unraveled.

In another embodiment of the invention, methods for treating a cerebral aneurysm are described. An implant structure is provided. The implant structure includes a self-expanding resilient permeable shell having a proximal end, a distal end, and a longitudinal axis. The shell includes a plurality of elongate resilient filaments having a braided structure, wherein the plurality of filaments are secured at least at one of the proximal end or the distal end thereof. The device also includes a force biasing member secured at the distal end of the self-expanding resilient permeable shell. The permeable shell has a plurality of openings formed between the braided filaments. The permeable shell has a radially constrained elongated state configured for delivery within a microcatheter and has an expanded state with a globular, axially shortened configuration relative to the radially constrained state. The force biasing member has a linear, straightened shape configured for delivery within a microcatheter and an expanded state after delivery from the microcatheter. The implant is advanced within a microcatheter to a region near the cerebral aneurysm. The implant is deployed within the cerebral aneurysm such that the force biasing member is positioned near a dome of the cerebral aneurysm and assumes the expanded state, and the permeable shell assumes the expanded deployed state within the cerebral aneurysm. The microcatheter is then withdrawn from the region near the cerebral aneurysm after the implant is deployed.

Once deployed in the cerebral aneurysm, the force biasing member may push the permeable shell against an opening of the cerebral aneurysm. When at least partially compressed in an axial direction, the metallic coil can apply an axial bias of at least 0.27 grams, alternatively at least 2.67 grams, alternatively at least 16.6 grams, alternatively between about 0.27 grams and about 40 grams, alternatively between about 2.67 grams and about 30 grams, alternatively between about 16.6 grams and about 20 grams. The force biasing member may be configured to conform to a three-dimensional framing shape. The force biasing member may be made from wire comprising platinum.

In another embodiment, a device for treatment of an aneurysm within a patient's vasculature is described. The device includes a self-expanding resilient permeable shell having a proximal end, a distal end, and a longitudinal axis. The shell includes a plurality of elongate resilient filaments having a braided structure. The plurality of filaments are secured at the distal end of the permeable shell. Distal regions of at least some of the plurality of filaments extend beyond the distal end of the permeability shell and form an extension having a generally circular shape when expanded. The plurality of filaments may be secured by a cylindrical hub having a proximal and distal end, and the extension may extend from the distal end of the cylindrical hub. The distal regions of filaments forming the extension may be straight or braided or partially braided, or the braid may be partially undone or unraveled.

In another embodiment of the invention, methods for treating a cerebral aneurysm are described. An implant structure is provided. The implant structure includes a self-expanding resilient permeable shell having a proximal end, a distal end, and a longitudinal axis. The shell includes a plurality of elongate resilient filaments having a braided structure. The plurality of filaments are secured at the distal end of the permeable shell. Distal regions of at least some of the plurality of filaments extend beyond the distal end of the permeability shell and form an extension having a generally circular shape when expanded. The implant is advanced within a microcatheter to a region near the cerebral aneurysm. The implant is deployed within the cerebral aneurysm such that the extension is positioned near a dome of the cerebral aneurysm and assumes the generally circular expanded state, and the permeable shell assumes the expanded deployed state within the cerebral aneurysm. The microcatheter is then withdrawn from the region near the cerebral aneurysm after the implant is deployed. The plurality of filaments may be secured by a cylindrical hub having a proximal and distal end, and the extension may extend from the distal end of the cylindrical hub. The distal regions of filaments forming the extension may be straight or braided or partially braided, or the braid may be partially undone or unraveled.

BRIEF DESCRIPTION OF THE DRAWINGS

FIG. 7 is an enlarged view of the woven filament structure taken from the encircled portion 7 shown in FIG. 5.

FIG. 8 is an enlarged view of the woven filament structure taken from the encircled portion 8 shown in FIG. 6.

FIG. 12 is an elevation view of a distal portion of a delivery device or actuator showing some internal structure of the device.

FIG. 13 is an elevation view of the delivery device of FIG. 12 with the addition of some tubular elements over the internal structures.

FIG. 14 is an elevation view of the distal portion of the delivery device of FIG. 13 with an outer coil and marker in place.

FIG. 15 is an elevation view of a proximal portion of the delivery device.

FIGS. 34A-34B illustrate a method of implanting a second configuration of the embodiment of FIG. 33 within a vascular defect.

FIGS. 35A-35B illustrate a method of implanting a third configuration of the embodiment of FIG. 33 within a vascular defect.

FIG. 39 is a partial cross-sectional view of an embodiment of a multi-lobe mesh device.

FIG. 40 is a partial cross-section of the multi-lobe mesh device of FIG. 37 in place in relation to a vascular defect.

FIG. 41 is a castellated mandrel assembly used in the braiding process of the embodiments of devices for treatment of a patient's vasculature.

FIG. 42 is a section view of the castellated mandrel assembly of FIG. 41.

FIGS. 64-67 illustrate the thrombus removal device in use to remove a thrombus from a blood vessel.

DETAILED DESCRIPTION

Figure 1:
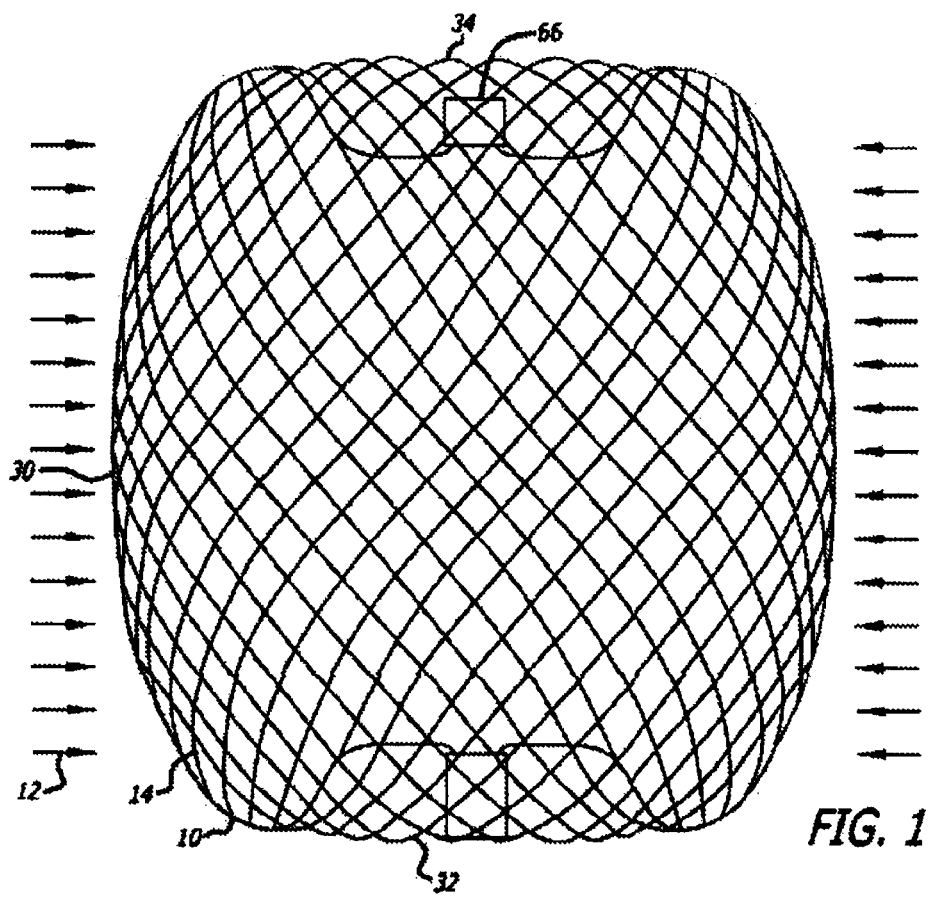
FIG. 1 is an elevation view of an embodiment of a device for treatment of a patient's vasculature and a plurality of arrows indicating inward radial force.

Discussed herein are devices and methods for the treatment of vascular defects that are suitable for minimally invasive deployment within a patient's vasculature, and particularly, within the cerebral vasculature of a patient. For such embodiments to be safely and effectively delivered to a desired treatment site and effectively deployed, some device embodiments may be configured for collapse to a low profile constrained state with a transverse dimension suitable for delivery through an inner lumen of a microcatheter and deployment from a distal end thereof. Embodiments of these devices may also maintain a clinically effective configuration with sufficient mechanical integrity once deployed so as to withstand dynamic forces within a patient's vasculature over time that may otherwise result in compaction of a deployed device. It may also be desirable for some device embodiments to acutely occlude a vascular defect of a patient during the course of a procedure in order to provide more immediate feedback regarding success of the treatment to a treating physician. Unless otherwise stated, one or more of the features, dimensions, or materials of the various embodiments may be used in other similar embodiments discussed herein.

Some embodiments are particularly useful for the treatment of cerebral aneurysms by reconstructing a vascular wall so as to wholly or partially isolate a vascular defect from a patient's blood flow. Some embodiments may be configured to be deployed within a vascular defect to facilitate reconstruction, bridging of a vessel wall or both in order to treat the vascular defect. For some of these embodiments, a permeable shell of the device may be configured to anchor or fix the permeable shell in a clinically beneficial position. For some embodiments, the device may be disposed in whole or in part within the vascular defect in order to anchor or fix the device with respect to the vascular structure or defect. The permeable shell may be configured to span an opening, neck or other portion of a vascular defect in order to isolate the vascular defect, or a portion thereof, from the patient's nominal vascular system in order allow the defect to heal or to otherwise minimize the risk of the defect to the patient's health.

For some or all of the embodiments of devices for treatment of a patient's vasculature discussed herein, the permeable shell or layer, or permeable shells or layers, of the device or devices may be configured to allow some initial perfusion of blood through the permeable shell or layer. The porosity of the permeable shell may be configured to sufficiently isolate the vascular defect so as to promote healing and isolation of the defect, but allow sufficient initial flow through the permeable shell so as to reduce or otherwise minimize the mechanical force exerted on the membrane the dynamic flow of blood or other fluids within the vasculature against the device. For some embodiments of devices for treatment of a patient's vasculature, only a portion of the permeable shell that spans the opening or neck of the vascular defect, sometimes referred to as a defect spanning portion, need be permeable and/or conducive to thrombus formation in a patient's bloodstream. For such embodiments, that portion of the device that does not span an opening or neck of the vascular defect may be substantially non-permeable or completely permeable with a pore or opening configuration that is too large to effectively promote thrombus formation. In addition, a portion of the permeable shell that is initially permeable or semi-permeable to blood flow may become substantially non-permeable or completely non-permeable due to thrombus formation on the filaments of the device. In some cases, thrombus formation on filaments of the permeable shell or any other portion of the device may serve to decrease the pore size between the filaments or close off the pores of the permeable shell completely.

In general, it may be desirable in some cases to use a hollow, thin walled device with a permeable shell of resilient material that may be constrained to a low profile for delivery within a patient. Such a device may also be configured to expand radially outward upon removal of the constraint such that the shell of the device assumes a larger volume and fills or otherwise occludes a vascular defect within which it is deployed. The outward radial expansion of the shell may serve to engage some or all of an inner surface of the vascular defect whereby mechanical friction between an outer surface of the permeable shell of the device and the inside surface of the vascular defect effectively anchors the device within the vascular defect. Some embodiments of such a device may also be partially or wholly mechanically captured within a cavity of a vascular defect, particularly where the defect has a narrow neck portion with a larger interior volume. In order to achieve a low profile and volume for delivery and be capable of a high ratio of expansion by volume, some device embodiments include a matrix of woven or braided filaments that are coupled together by the interwoven structure so as to form a self-expanding permeable shell having a pore or opening pattern between couplings or intersections of the filaments that is substantially regularly spaced and stable, while still allowing for conformity and volumetric constraint.

As used herein, the terms woven and braided are used interchangeably to mean any form of interlacing of filaments to form a mesh structure. In the textile and other industries, these terms may have different or more specific meanings depending on the product or application such as whether an article is made in a sheet or cylindrical form. For purposes of the present disclosure, these terms are used interchangeably.

For some embodiments, three factors may be critical for a woven or braided wire occlusion device for treatment of a patient's vasculature that can achieve a desired clinical outcome in the endovascular treatment of cerebral aneurysms. We have found that for effective use in some applications, it may be desirable for the implant device to have sufficient radial stiffness for stability, limited pore size for near-complete acute (intra-procedural) occlusion, and a collapsed profile that is small enough to allow insertion through an inner lumen of a microcatheter. A device with a radial stiffness below a certain threshold may be unstable and may be at higher risk of undesired movement and embolization of the wrong region of the vasculature in some cases. Larger pores between filament intersections in a braided or woven structure may not generate thrombus and occlude a vascular defect in an acute setting and thus may not give a treating physician or health professional such clinical feedback that the flow disruption will lead to a complete and lasting occlusion of the vascular defect being treated. Delivery of a device for treatment of a patient's vasculature through a standard microcatheter may be highly desirable to allow access through the tortuous cerebral vasculature in the manner that a treating physician is accustomed.

For some embodiments, it may be desirable to use filaments having two or more different diameters or transverse dimensions to form a permeable shell in order to produce a desired configuration as discussed in more detail below. The radial stiffness of a two-filament (two different diameters) woven device may be expressed as a function of the number of filaments and their diameters, as follows:

$$S_{radial} = (1.2 \times 10^6 \text{ lbf}/D^4)(N_l d_l^4 + N_s d_s^4)$$

where $S_{radial}$ is the radial stiffness in pounds force (lbf),
D is the Device diameter (transverse dimension),
$N_l$ is the number of large filaments,
$N_s$ is the number of small filaments,
$d_l$ is the diameter of the large filaments in inches, and
$d_s$ is the diameter of the small filaments in inches.

Using this expression, the radial stiffness $S_{radial}$ may be between about 0.014 and about 0.284 lbf force for some embodiments of particular clinical value. In some embodiments, the radial stiffness $S_{radial}$ may be between about 0.015 and about 0.065 lbf. In some embodiments, the radial stiffness $S_{radial}$ may be measured at a deformation of about 50%.

The maximum pore size in a portion of a device that spans a neck or opening of a vascular defect desirable for some useful embodiments of a woven wire device for treatment of a patient's vasculature may be expressed as a function of the total number of all filaments, filament diameter and the device diameter. The difference between filament sizes where two or more filament diameters or transverse dimensions are used may be ignored in some cases for devices where the filament size(s) are very small compared to the device dimensions. For a two-filament device, i.e., a device made from filaments of two different sizes, the smallest filament diameter may be used for the calculation. Thus, the maximum pore size for such embodiments may be expressed as follows:

$$P_{max}(1.7/N_T)(\pi D - (N_T d_{w/2}))$$

where $P_{max}$ is the average pore size,
D is the Device diameter (transverse dimension),
$N_T$ is the total number of all filaments, and
$d_w$ is the diameter of the filaments (smallest) in inches.

Using this expression, the maximum pore size, $P_{max}$, of a portion of a device that spans an opening of a vascular defect or neck, or any other suitable portion of a device, may be less than about 0.016 inches or about 400 microns for some embodiments. In some embodiments the maximum pore size for a defect spanning portion or any other suitable portion of a device may be less than about 0.012 inches or about 300 microns. In some embodiments, the maximum pore size for a defect spanning portion or any other suitable portion of a device may be less than about 0.008 inches or about 200 microns.

The collapsed profile of a two-filament (profile having two different filament diameters) woven filament device may be expressed as the function:

$$P_c = 1.48((N_l d_l^2 + N_s d_s 2))^{1/2}$$

where $P_c$ is the collapsed profile of the device,
$N_l$ is the number of large filaments,
$N_s$ is the number of small filaments,
$d_l$ is the diameter of the large filaments in inches, and
$d_s$ is the diameter of the small filaments in inches.

Using this expression, the collapsed profile $P_c$ may be less than about 1.0 mm for some embodiments of particular clinical value. In some embodiments of particular clinical value, the device may be constructed so as to have all three factors ($S_{radial}$, $P_{max}$ and $P_c$) above within the ranges discussed above; $S_{radial}$ between about 0.014 lbf and about 0.284 lbf, or between about 0.015 lbf and about 0.065 lbf, $P_{max}$ less than about 300 microns and $P_c$ less than about 1.0 mm, simultaneously. In some such embodiments, the device may be made to include about 70 filaments to about 300 filaments. In some cases, the filaments may have an outer transverse dimension or diameter of about 0.0004 inches to about 0.002 inches. In some cases the filaments may have an outer transverse dimension or diameter of about 0.0005 inches to about 0.0015 inches. In some cases the filaments may have an outer transverse dimension or diameter of about 0.00075 inches to about 0.00125 inches.

As has been discussed, some embodiments of devices for treatment of a patient's vasculature call for sizing the device which approximates (or with some over-sizing) the vascular site dimensions to fill the vascular site. One might assume that scaling of a device to larger dimensions and using larger filaments would suffice for such larger embodiments of a device. However, for the treatment of brain aneurysms, the diameter or profile of the radially collapsed device is limited by the catheter sizes that can be effectively navigated within the small, tortuous vessels of the brain. Further, as a device is made larger with a given or fixed number of resilient filaments having a given size or thickness, the pores or openings between junctions of the filaments become correspondingly larger. In addition, for a given filament size the flexural modulus or stiffness of the filaments and thus the structure decrease with increasing device dimension. Flexural modulus may be defined as the ratio of stress to strain. Thus, a device may be considered to have a high flexural modulus or be stiff if the strain (deflection) is low under a given force. A stiff device may also be said to have low compliance.

Figure 2:
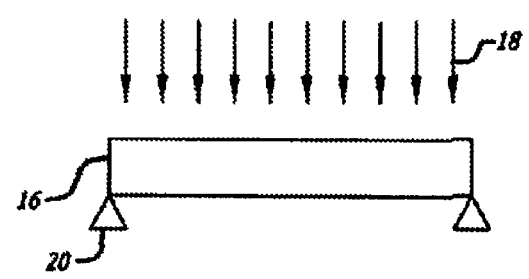
FIG. 2 is an elevation view of a beam supported by two simple supports and a plurality of arrows indicating force against the beam.
Figure 3:
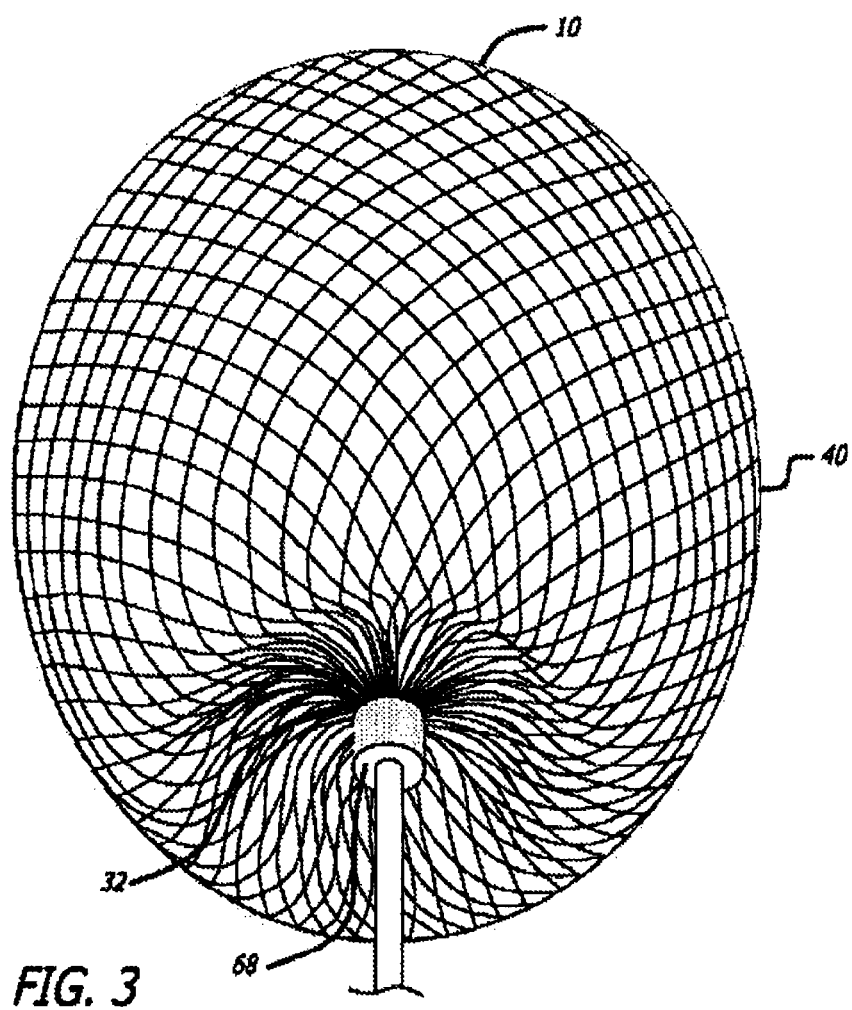
FIG. 3 is a bottom perspective view of an embodiment of a device for treatment of a patient's vasculature.

To properly configure larger size devices for treatment of a patient's vasculature, it may be useful to model the force on a device when the device is deployed into a vascular site or defect, such as a blood vessel or aneurysm, that has a diameter or transverse dimension that is smaller than a nominal diameter or transverse dimension of the device in a relaxed unconstrained state. As discussed, it may be advisable to "over-size" the device in some cases so that there is a residual force between an outside surface of the device and an inside surface of the vascular wall. The inward radial force on a device 10 that results from over-sizing is illustrated schematically in FIG. 1 with the arrows 12 in the figure representing the inward radial force. As shown in FIG. 2, these compressive forces on the filaments 14 of the device in FIG. 1 can be modeled as a simply supported beam 16 with a distributed load or force as shown by the arrows 18 in the figure. It can be seen from the equation below for the deflection of a beam with two simple supports 20 and a distributed load that the deflection is a function of the length, L to the 4th power:

$$\text{Deflection of Beam} = 5FL^4/384EI$$

where F=force,
L=length of beam,
E=Young's Modulus, and
I=moment of inertia.

Thus, as the size of the device increases and L increases, the compliance increases substantially. Accordingly, an outward radial force exerted by an outside surface of the filaments 14 of the device 10 against a constraining force when inserted into a vascular site such as blood vessel or aneurysm is lower for a given amount of device compression or over-sizing. This force may be important in some applications to assure device stability and to reduce the risk of migration of the device and potential distal embolization.

In some embodiments, a combination of small and large filament sizes may be utilized to make a device with a desired radial compliance and yet have a collapsed profile that is configured to fit through an inner lumen of commonly used microcatheters. A device fabricated with even a small number of relatively large filaments 14 can provide reduced radial compliance (or increased stiffness) compared to a device made with all small filaments. Even a relatively small number of larger filaments may provide a substantial increase in bending stiffness due to change in the moment of Inertia that results from an increase in diameter without increasing the total cross sectional area of the filaments. The moment of inertia (I) of a round wire or filament may be defined by the equation:

$$I=\pi d^4/64$$

where d is the diameter of the wire or filament.

Since the moment of inertia is a function of filament diameter to the fourth power, a small change in the diameter greatly increases the moment of inertia. Thus, a small change in filament size can have substantial impact on the deflection at a given load and thus the compliance of the device.

Thus, the stiffness can be increased by a significant amount without a large increase in the cross sectional area of a collapsed profile of the device 10. This may be particularly important as device embodiments are made larger to treat large aneurysms. While large cerebral aneurysms may be relatively rare, they present an important therapeutic challenge as some embolic devices currently available to physicians have relatively poor results compared to smaller aneurysms.

As such, some embodiments of devices for treatment of a patient's vasculature may be formed using a combination of filaments 14 with a number of different diameters such as 2, 3, 4, 5 or more different diameters or transverse dimensions. In device embodiments where filaments with two different diameters are used, some larger filament embodiments may have a transverse dimension of about 0.001 inches to about 0.004 inches and some small filament embodiments may have a transverse dimension or diameter of about 0.0004 inches and about 0.0015 inches, more specifically, about 0.0004 inches to about 0.001 inches. Some structures may use filaments having a transverse dimension of up to about 0.001 inches. The ratio of the number of large filaments to the number of small filaments may be between about 2 and 12 and may also be between about 4 and 8. In some embodiments, the difference in diameter or transverse dimension between the larger and smaller filaments may be less than about 0.004 inches, more specifically, less than about 0.0035 inches, and even more specifically, less than about 0.002 inches. As discussed generally above, it may not always be necessary for all wires or filaments to meet the parameters for the various relationships discussed herein. This may be particularly true where relatively large numbers of filaments are being used for a distinct structure. In some cases, a filamentary structure may meet the relationship constraints discussed herein where the predominance of filaments of a permeable shell or inner structure meet a size constraint.

As discussed above, device embodiments 10 for treatment of a patient's vasculature may include a plurality of wires, fibers, threads, tubes or other filamentary elements that form a structure that serves as a permeable shell. For some embodiments, a globular shape may be formed from such filaments by connecting or securing the ends of a tubular braided structure. For such embodiments, the density of a braided or woven structure may inherently increase at or near the ends where the wires or filaments 14 are brought together and decrease at or near a middle portion 30 disposed between a proximal end 32 and distal end 34 of the permeable shell 40.

For some embodiments, an end or any other suitable portion of a permeable shell 40 may be positioned in an opening or neck of a vascular defect such as an aneurysm for treatment. As such, a braided or woven filamentary device with a permeable shell may not require the addition of a separate defect spanning structure having properties different from that of a nominal portion of the permeable shell to achieve hemostasis and occlusion of the vascular defect. Such a filamentary device may be fabricated by braiding, weaving or other suitable filament fabrication techniques. Such device embodiments may be shape set into a variety of three dimensional shapes such as discussed herein.

Referring to FIGS. 3-10, an embodiment of a device for treatment of a patient's vasculature 10 is shown. The device 10 includes a self-expanding resilient permeable shell 40 having a proximal end 32, a distal end 34, a longitudinal axis 46 and further comprising a plurality of elongate resilient filaments 14 including large filaments 48 and small filaments 50 of at least two different transverse dimensions as shown in more detail in FIGS. 5, 7 and 18. The filaments 14 have a woven structure and are secured relative to each other at proximal ends 60 and distal ends 62 thereof. The permeable shell 40 of the device has a radially constrained elongated state configured for delivery within a microcatheter 61, as shown in FIG. 11, with the thin woven filaments 14 extending longitudinally from the proximal end 42 to the distal end 44 radially adjacent each other along a length of the filaments.

As shown in FIGS. 3-6, the permeable shell 40 also has an expanded relaxed state with a globular and longitudinally shortened configuration relative to the radially constrained state. In the expanded state, the woven filaments 14 form the self-expanding resilient permeable shell 40 in a smooth path radially expanded from a longitudinal axis 46 of the device between the proximal end 32 and distal end 34. The woven structure of the filaments 14 includes a plurality of openings 64 in the permeable shell 40 formed between the woven filaments. For some embodiments, the largest of said openings 64 may be configured to allow blood flow through the openings only at a velocity below a thrombotic threshold velocity. Thrombotic threshold velocity has been defined, at least by some, as the time-average velocity at which more than 50% of a vascular graft surface is covered by thrombus when deployed within a patient's vasculature. In the context of aneurysm occlusion, a slightly different threshold may be appropriate. Accordingly, the thrombotic threshold velocity as used herein shall include the velocity at which clotting occurs within or on a device, such as device 10, deployed within a patient's vasculature such that blood flow into a vascular defect treated by the device is substantially blocked in less than about 1 hour or otherwise during the treatment procedure. The blockage of blood flow into the vascular defect may be indicated in some cases by minimal contrast agent entering the vascular defect after a sufficient amount of contrast agent has been injected into the patient's vasculature upstream of the implant site and visualized as it dissipates from that site. Such sustained blockage of flow within less than about 1 hour or during the duration of the implantation procedure may also be referred to as acute occlusion of the vascular defect.

As such, once the device 10 is deployed, any blood flowing through the permeable shell may be slowed to a velocity below the thrombotic threshold velocity and thrombus will begin to form on and around the openings in the permeable shell 40. Ultimately, this process may be configured to produce acute occlusion of the vascular defect within which the device 10 is deployed. For some embodiments, at least the distal end of the permeable shell 40 may have a reverse bend in an everted configuration such that the secured distal ends 62 of the filaments 14 are withdrawn axially within the nominal permeable shell structure or contour in the expanded state. For some embodiments, the proximal end of the permeable shell further includes a reverse bend in an everted configuration such that the secured proximal ends 60 of the filaments 14 are withdrawn axially within the nominal permeable shell structure 40 in the expanded state. As used herein, the term everted may include a structure that is everted, partially everted and/or recessed with a reverse bend as shown in the device embodiment of FIGS. 3-6. For such embodiments, the ends 60 and 62 of the filaments 14 of the permeable shell or hub structure disposed around the ends may be withdrawn within or below the globular shaped periphery of the permeable shell of the device.

The elongate resilient filaments 14 of the permeable shell 40 may be secured relative to each other at proximal ends 60 and distal ends 62 thereof by one or more methods including welding, soldering, adhesive bonding, epoxy bonding or the like. In addition to the ends of the filaments being secured together, a distal hub 66 may also be secured to the distal ends 62 of the thin filaments 14 of the permeable shell 40 and a proximal hub 68 secured to the proximal ends 60 of the thin filaments 14 of the permeable shell 40. The proximal hub 68 may include a cylindrical member that extends proximally beyond the proximal ends 60 of the thin filaments so as to form a cavity 70 within a proximal portion of the proximal hub 68. The proximal cavity 70 may be used for holding adhesives such as epoxy, solder or any other suitable bonding agent for securing an elongate detachment tether 72 that may in turn be detachably secured to a delivery apparatus such as is shown in FIGS. 11-15.

For some embodiments, the elongate resilient filaments 14 of the permeable shell 40 may have a transverse cross section that is substantially round in shape and be made from a superelastic material that may also be a shape memory metal. The shape memory metal of the filaments of the permeable shell 40 may be heat set in the globular configuration of the relaxed expanded state as shown in FIGS. 3-6. Suitable superelastic shape memory metals may include alloys such as NiTi alloy and the like. The superelastic properties of such alloys may be useful in providing the resilient properties to the elongate filaments 14 so that they can be heat set in the globular form shown, fully constrained for delivery within an inner lumen of a microcatheter and then released to self-expand back to substantially the original heat set shape of the globular configuration upon deployment within a patient's body.

The device 10 may have an everted filamentary structure with a permeable shell 40 having a proximal end 32 and a distal end 34 in an expanded relaxed state. The permeable shell 40 has a substantially enclosed configuration for the embodiments shown. Some or all of the permeable shell 40 of the device 10 may be configured to substantially block or impede fluid flow or pressure into a vascular defect or otherwise isolate the vascular defect over some period of time after the device is deployed in an expanded state. The permeable shell 40 and device 10 generally also has a low profile, radially constrained state, as shown in FIG. 11, with an elongated tubular or cylindrical configuration that includes the proximal end 32, the distal end 34 and a longitudinal axis 46. While in the radially constrained state, the elongate flexible filaments 14 of the permeable shell 40 may be disposed substantially parallel and in close lateral proximity to each other between the proximal end and distal end forming a substantially tubular or compressed cylindrical configuration.

Figure 4:
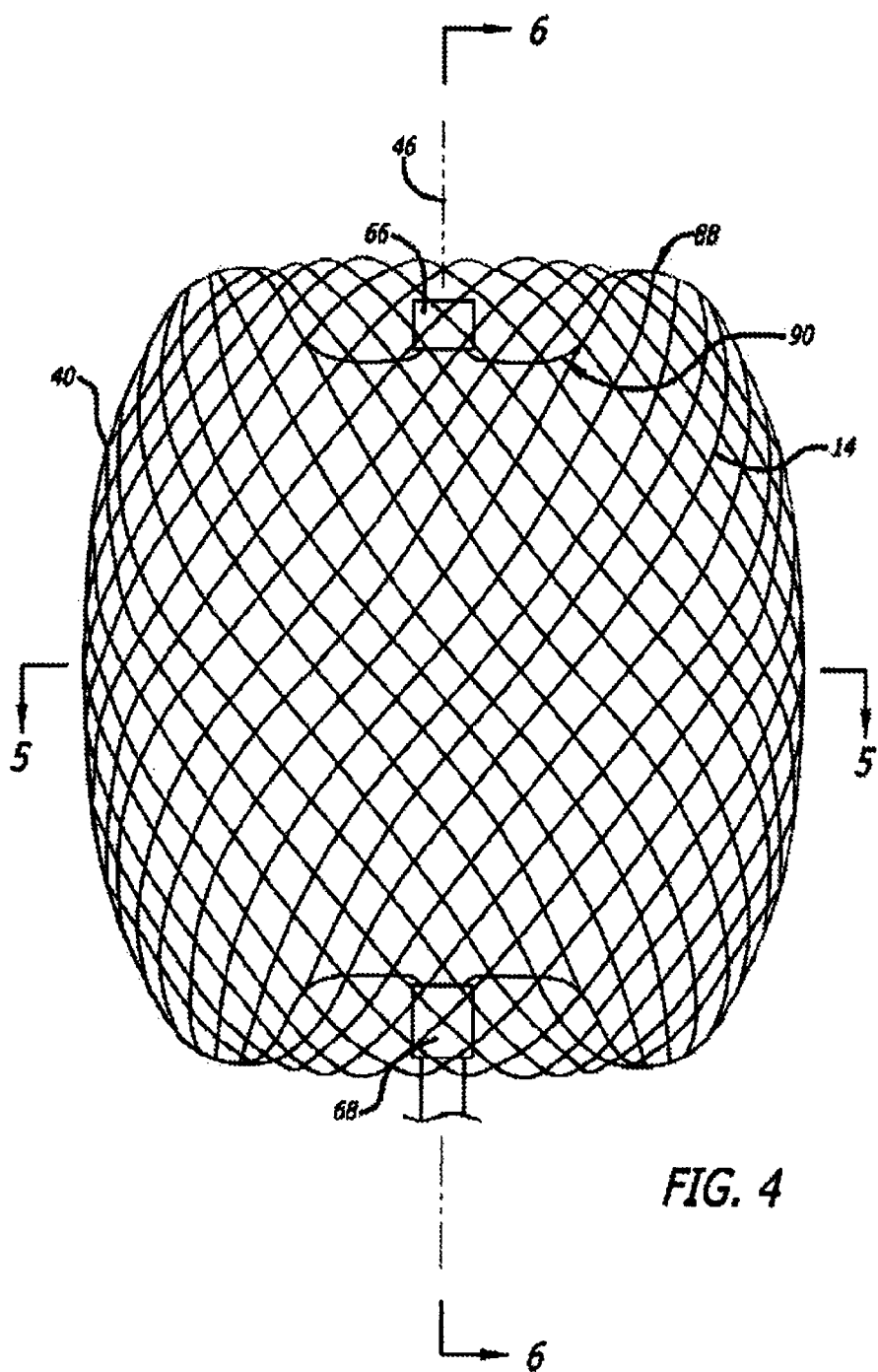
FIG. 4 is an elevation view of the device for treatment of a patient's vasculature of FIG. 3.
Figure 5:
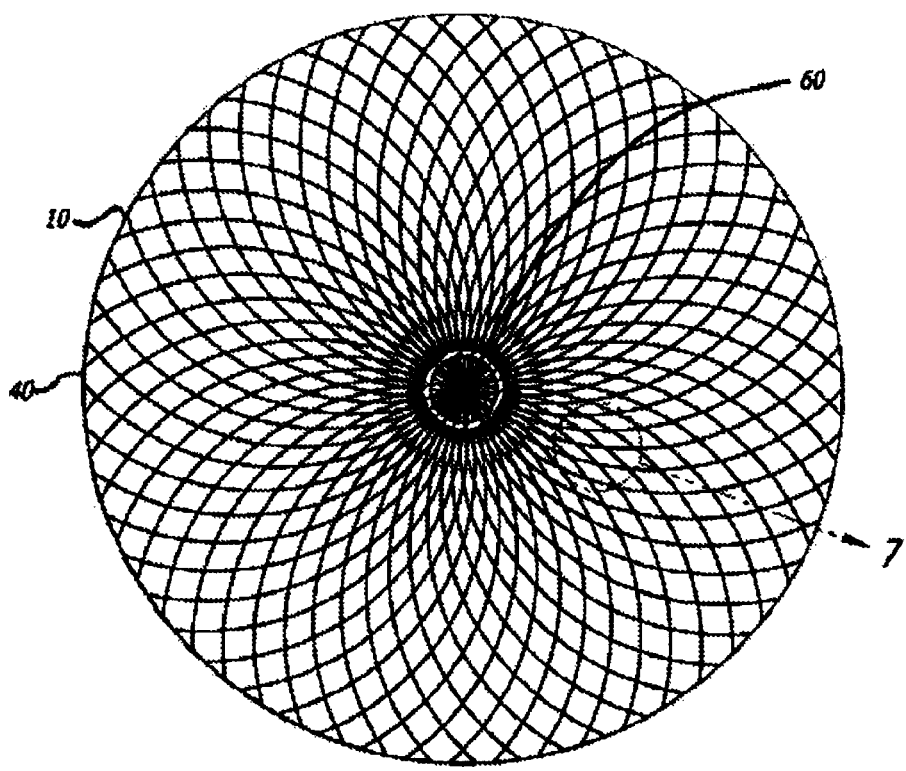
FIG. 5 is a transverse cross sectional view of the device of FIG. 4 taken along lines 5-5 in FIG. 4.

Proximal ends 60 of at least some of the filaments 14 of the permeable shell 40 may be secured to the proximal hub 68 and distal ends 62 of at least some of the filaments 14 of the permeable shell 40 are secured to the distal hub 66, with the proximal hub 68 and distal hub 66 being disposed substantially concentric to the longitudinal axis 46 as shown in FIG. 4. The ends of the filaments 14 may be secured to the respective hubs 66 and 68 by any of the methods discussed above with respect to securement of the filament ends to each other, including the use of adhesives, solder, welding and the like. A middle portion 30 of the permeable shell 40 may have a first transverse dimension with a low profile suitable for delivery from a microcatheter as shown in FIG. 11. Radial constraint on the device 10 may be applied by an inside surface of the inner lumen of a microcatheter, such as the distal end portion of the microcatheter 61 shown, or it may be applied by any other suitable mechanism that may be released in a controllable manner upon ejection of the device 10 from the distal end of the catheter. In FIG. 11 a proximal end or hub 68 of the device 10 is secured to a distal end of an elongate delivery apparatus 110 of a delivery system 112 disposed at the proximal hub 68 of the device 10.

Some device embodiments 10 having a braided or woven filamentary structure may be formed using about 10 filaments to about 300 filaments 14, more specifically, about 10 filaments to about 100 filaments 14, and even more specifically, about 60 filaments to about 80 filaments 14. Some embodiments of a permeable shell 40 may include about 70 filaments to about 300 filaments extending from the proximal end 32 to the distal end 34, more specifically, about 100 filaments to about 200 filaments extending from the proximal end 32 to the distal end 34. For some embodiments, the filaments 14 may have a transverse dimension or diameter of about 0.0008 inches to about 0.004 inches. The elongate resilient filaments 14 in some cases may have an outer transverse dimension or diameter of about 0.0005 inch to about 0.005 inch, more specifically, about 0.001 inch to about 0.003 inch, and in some cases about 0.0004 inches to about 0.002 inches. For some device embodiments 10 that include filaments 14 of different sizes, the large filaments 48 of the permeable shell 40 may have a transverse dimension or diameter that is about 0.001 inches to about 0.004 inches and the small filaments 50 may have a transverse dimension or diameter of about 0.0004 inches to about 0.0015 inches, more specifically, about 0.0004 inches to about 0.001 inches. In addition, a difference in transverse dimension or diameter between the small filaments 50 and the large filaments 48 may be less than about 0.004 inches, more specifically, less than about 0.0035 inches, and even more specifically, less than about 0.002 inches. For embodiments of permeable shells 40 that include filaments 14 of different sizes, the number of small filaments 50 of the permeable shell 40 relative to the number of large filaments 48 of the permeable shell 40 may be about 2 to 1 to about 15 to 1, more specifically, about 2 to 1 to about 12 to 1, and even more specifically, about 4 to 1 to about 8 to 1.

The expanded relaxed state of the permeable shell 40, as shown in FIG. 4, has an axially shortened configuration relative to the constrained state such that the proximal hub 68 is disposed closer to the distal hub 66 than in the constrained state. Both hubs 66 and 68 are disposed substantially concentric to the longitudinal axis 46 of the device and each filamentary element 14 forms a smooth arc between the proximal and distal hubs 66 and 68 with a reverse bend at each end. A longitudinal spacing between the proximal and distal hubs 66 and 68 of the permeable shell 40 in a deployed relaxed state may be about 25 percent to about 75 percent of the longitudinal spacing between the proximal and distal hubs 66 and 68 in the constrained cylindrical state, for some embodiments. The arc of the filaments 14 between the proximal and distal ends 32 and 34 may be configured such that a middle portion of each filament 14 has a second transverse dimension substantially greater than the first transverse dimension.

For some embodiments, the permeable shell 40 may have a first transverse dimension in a collapsed radially constrained state of about 0.2 mm to about 2 mm and a second transverse dimension in a relaxed expanded state of about 4 mm to about 30 mm. For some embodiments, the second transverse dimension of the permeable shell 40 in an expanded state may be about 2 times to about 150 times the first transverse dimension, more specifically, about 10 times to about 25 times the first or constrained transverse dimension. A longitudinal spacing between the proximal end 32 and distal end 34 of the permeable shell 40 in the relaxed expanded state may be about 25% percent to about 75% percent of the spacing between the proximal end 32 and distal end 34 in the constrained cylindrical state. For some embodiments, a major transverse dimension of the permeable shell 40 in a relaxed expanded state may be about 4 mm to about 30 mm, more specifically, about 9 mm to about 15 mm, and even more specifically, about 4 mm to about 8 mm.

Figure 6:
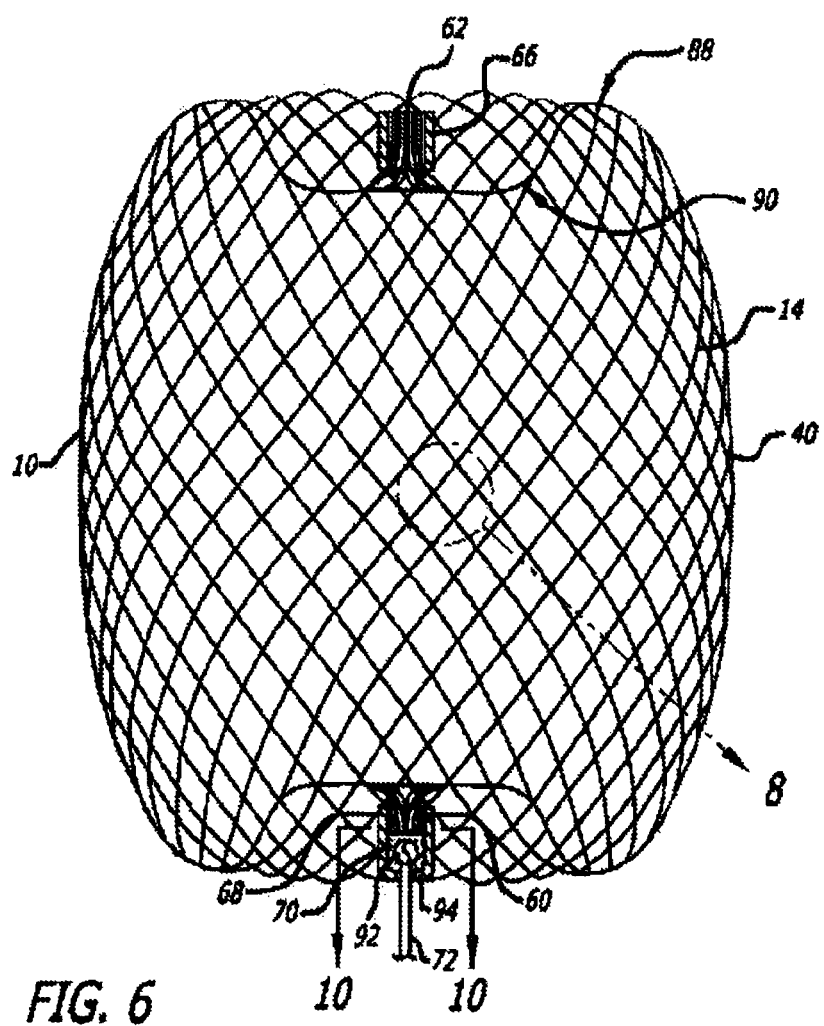
FIG. 6 shows the device of FIG. 4 in longitudinal section taken along lines 6-6 in FIG. 4.
Figure 9:
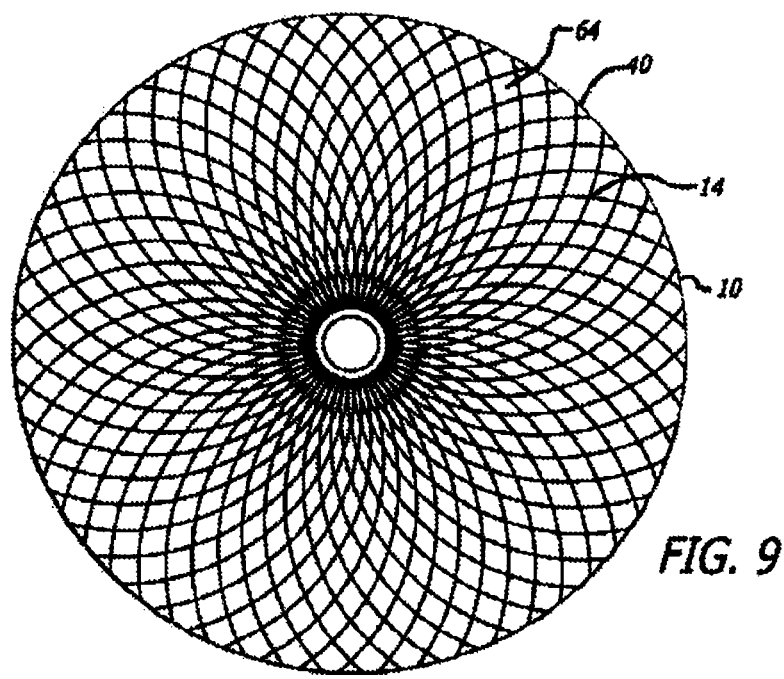
FIG. 9 is a proximal end view of the device of FIG. 3.

An arced portion of the filaments 14 of the permeable shell 40 may have a sinusoidal-like shape with a first or outer radius 88 and a second or inner radius 90 near the ends of the permeable shell 40 as shown in FIG. 6. This sinusoid-like or multiple curve shape may provide a concavity in the proximal end 32 that may reduce an obstruction of flow in a parent vessel adjacent a vascular defect. For some embodiments, the first radius 88 and second radius 90 of the permeable shell 40 may be between about 0.12 mm to about 3 mm. For some embodiments, the distance between the proximal end 32 and distal end 34 may be less than about 60% of the overall length of the permeable shell 40 for some embodiments. Such a configuration may allow for the distal end 34 to flex downward toward the proximal end 32 when the device 10 meets resistance at the distal end 34 and thus may provide longitudinal conformance. The filaments 14 may be shaped in some embodiments such that there are no portions that are without curvature over a distance of more than about 2 mm. Thus, for some embodiments, each filament 14 may have a substantially continuous curvature. This substantially continuous curvature may provide smooth deployment and may reduce the risk of vessel perforation. For some embodiments, one of the ends 32 or 34 may be retracted or everted to a greater extent than the other so as to be more longitudinally or axially conformal than the other end.

The first radius 88 and second radius 90 of the permeable shell 40 may be between about 0.12 mm to about 3 mm for some embodiments. For some embodiments, the distance between the proximal end 32 and distal end 34 may be more than about 60% of the overall length of the expanded permeable shell 40. Thus, the largest longitudinal distance between the inner surfaces may be about 60% to about 90% of the longitudinal length of the outer surfaces or the overall length of device 10. A gap between the hubs 66 and 68 at the proximal end 32 and distal end 34 may allow for the distal hub 66 to flex downward toward the proximal hub 68 when the device 10 meets resistance at the distal end and thus provides longitudinal conformance. The filaments 14 may be shaped such that there are no portions that are without curvature over a distance of more than about 2 mm. Thus, for some embodiments, each filament 14 may have a substantially continuous curvature. This substantially continuous curvature may provide smooth deployment and may reduce the risk of vessel perforation. The distal end 34 may be retracted or everted to a greater extent than the proximal end 32 such that the distal end portion of the permeable shell 40 may be more radially conformal than the proximal end portion. Conformability of a distal end portion may provide better device conformance to irregular shaped aneurysms or other vascular defects. A convex surface of the device may flex inward forming a concave surface to conform to curvature of a vascular site.

Figure 10:
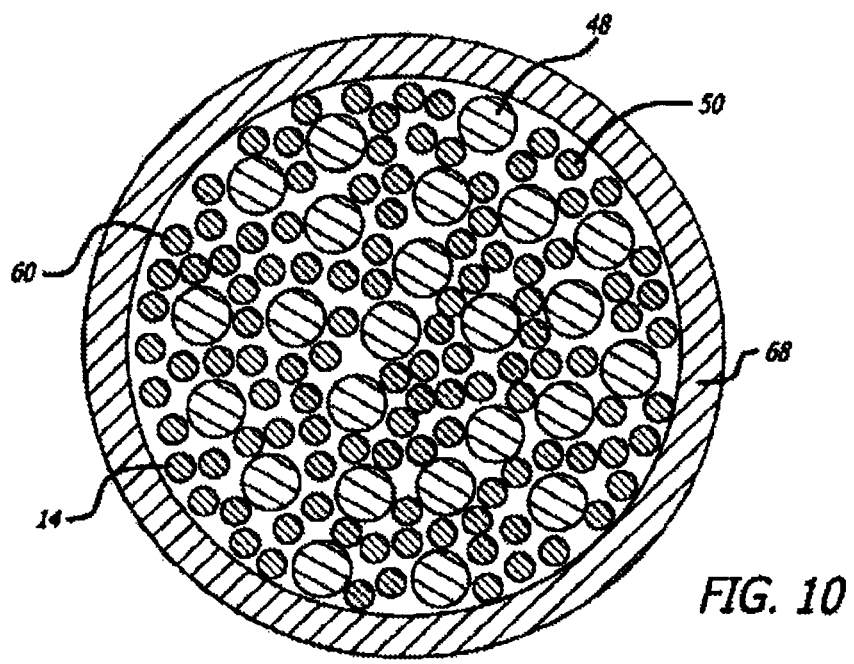
FIG. 10 is a transverse sectional view of a proximal hub portion of the device in FIG. 6 indicated by lines 10-10 in FIG. 6.
Figure 11:
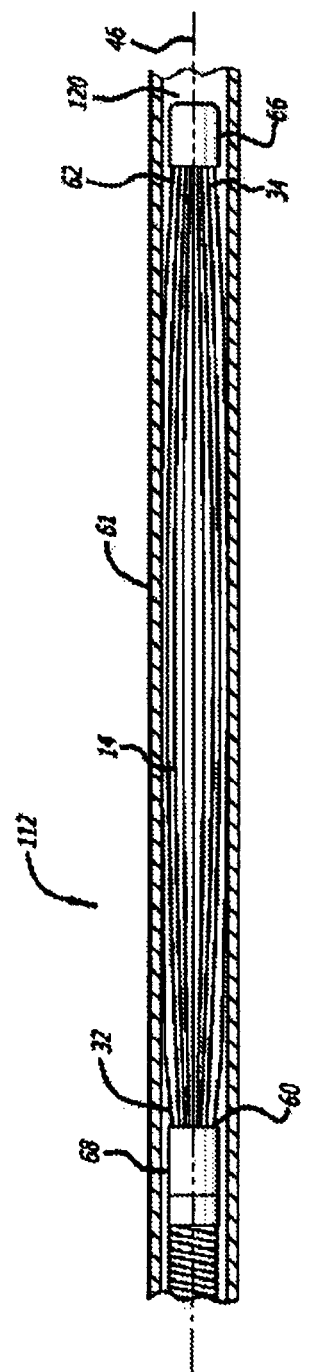
FIG. 11 is an elevation view in partial section of a distal end of a delivery catheter with the device for treatment of a patient's vasculature of FIG. 3 disposed therein in a collapsed constrained state.

FIG. 10 shows an enlarged view of the filaments 14 disposed within a proximal hub 68 of the device 10 with the filaments 14 of two different sizes constrained and tightly packed by an outer ring of the proximal hub 68. The tether member 72 may optionally be disposed within a middle portion of the filaments 14 or within the cavity 70 of the proximal hub 68 proximal of the proximal ends 60 of the filaments 14 as shown in FIG. 6. The distal end of the tether 72 may be secured with a knot 92 formed in the distal end thereof which is mechanically captured in the cavity 70 of the proximal hub 68 formed by a proximal shoulder portion 94 of the proximal hub 68. The knotted distal end 92 of the tether 72 may also be secured by bonding or potting of the distal end of the tether 72 within the cavity 70 and optionally amongst the proximal ends 60 of the filaments 14 with mechanical compression, adhesive bonding, welding, soldering, brazing or the like. The tether embodiment 72 shown in FIG. 6 has a knotted distal end 92 potted in the cavity of the proximal hub 68 with an adhesive. Such a tether 72 may be a dissolvable, severable or releasable tether that may be part of a delivery apparatus 110 used to deploy the device 10 as shown in FIG. 11 and FIGS. 23-26. FIG. 10 also shows the large filaments 48 and small filaments 50 disposed within and constrained by the proximal hub 68 that may be configured to secure the large and small filaments 48 and 50 in place relative to each other within the outer ring of the proximal hub 68.

FIGS. 7 and 8 illustrate some configuration embodiments of braided filaments 14 of a permeable shell 40 of the device 10 for treatment of a patient's vasculature. The braid structure in each embodiment is shown with a circular shape 100 disposed within a pore 64 of a woven or braided structure with the circular shape 100 making contact with each adjacent filament segment. The pore opening size may be determined at least in part by the size of the filament elements 14 of the braid, the angle overlapping filaments make relative to each other and the picks per inch of the braid structure. For some embodiments, the cells or openings 64 may have an elongated substantially diamond shape as shown in FIG. 7, and the pores or openings 64 of the permeable shell 40 may have a substantially more square shape toward a middle portion 30 of the device 10, as shown in FIG. 8. The diamond shaped pores or openings 64 may have a length substantially greater than the width particularly near the hubs 66 and 68. In some embodiments, the ratio of diamond shaped pore or opening length to width may exceed a ratio of 3 to 1 for some cells. The diamond-shaped openings 64 may have lengths greater than the width thus having an aspect ratio, defined as Length/Width of greater than 1. The openings 64 near the hubs 66 and 68 may have substantially larger aspect ratios than those farther from the hubs as shown in FIG. 7. The aspect ratio of openings 64 adjacent the hubs may be greater than about 4 to 1. The aspect ratio of openings 64 near the largest diameter may be between about 0.75 to 1 and about 2 to 1 for some embodiments. For some embodiments, the aspect ratio of the openings 64 in the permeable shell 40 may be about 0.5 to 1 to about 2 to 1.

The pore size defined by the largest circular shapes 100 that may be disposed within openings 64 of the braided structure of the permeable shell 40 without displacing or distorting the filaments 14 surrounding the opening 64 may range in size from about 0.005 inches to about 0.01 inches, more specifically, about 0.006 inches to about 0.009 inches, even more specifically, about 0.007 inches to about 0.008 inches for some embodiments. In addition, at least some of the openings 64 formed between adjacent filaments 14 of the permeable shell 40 of the device 10 may be configured to allow blood flow through the openings 64 only at a velocity below a thrombotic threshold velocity. For some embodiments, the largest openings 64 in the permeable shell structure 40 may be configured to allow blood flow through the openings 64 only at a velocity below a thrombotic threshold velocity. As discussed above, the pore size may be less than about 0.016 inches, more specifically, less than about 0.012 inches for some embodiments. For some embodiments, the openings 64 formed between adjacent filaments 14 may be about 0.005 inches to about 0.04 inches.

Referring to FIGS. 12-15, a delivery apparatus embodiment 110 of the delivery system 112 of FIG. 11 is shown in more detail. The apparatus 110 includes an elongate core wire 114 that extends from a proximal end 116 of the apparatus 110 to a distal section 118 of the apparatus 110 as shown in FIG. 12. The core wire 114 is configured to provide sufficient column strength to push a constrained device 10 for treatment of a patient's vasculature through an inner lumen 120 of the microcatheter 61 of the delivery system 112 as shown in FIG. 11. The core wire 114 also has sufficient tensile strength to withdraw or proximally retract the device 10 from a position outside the microcatheter 61 and axially within the inner lumen 120 of the microcatheter 61. The tether 72 that extends proximally from the proximal hub 68 is secured to the distal end of the core wire 114 with a length of shrinkable tubing 122 that is disposed over a portion of the tether 72 and a distal section of the core wire 114 and shrunk over both as shown in FIG. 13, although any other suitable means of securement may be used.

A heater coil 124 electrically coupled to a first conductor 126 and a second conductor 128 is disposed over a distal most portion of the tether 72. The heater coil 124 may also be covered with a length of polymer tubing 130 disposed over the heater coil 124 distal of the heat shrink tubing 122 that serves to act as a heat shield and minimizes the leakage of heat from the heater coil 124 into the environment, such as the patient's blood stream, around the delivery apparatus 110. Once the heat shrink tubing 122 and insulating polymer tubing 130 have been secured to the distal section 118 of the apparatus 110, the proximal portion of the tether 72 disposed proximal of the heat shrink tubing 122 may be trimmed as shown in FIG. 13. An over coil 132 that extends from a distal end 134 of the delivery apparatus 110 to a proximal section 136 of the apparatus 110 may then be disposed over the heater coil 124, core wire 114, tether 72, first conductor 126 and second conductor 128 to hold these elements together, produce a low friction outer surface and maintain a desired flexibility of the delivery apparatus 110. The proximal section 136 of the apparatus 110 includes the proximal terminus of the over coil 132 which is disposed distal of a first contact 138 and second contact 140 which are circumferentially disposed about the proximal section 136 of the core wire 114, insulated therefrom, and electrically coupled to the first conductor 126 and second conductor 128, respectively as shown in FIG. 15.

The heater coil 124 may be configured to receive electric current supplied through the first conductor 126 and second conductor 128 from an electrical energy source 142 coupled to the first contact 138 and second contact 140 at the proximal section 136 of the apparatus 110. The electrical current passed through the heater coil 124 heats the heater coil to a temperature above the melting point of the tether material 72 so as to melt the tether 72 and sever it upon deployment of the device 10.

Embodiments of the delivery apparatus 110 may generally have a length greater than the overall length of a microcatheter 61 to be used for the delivery system 112. This relationship allows the delivery apparatus 110 to extend, along with the device 10 secured to the distal end thereof, from the distal port of the inner lumen 120 of the microcatheter 61 while having sufficient length extending from a proximal end 150 of the microcatheter 61, shown in FIG. 17 discussed below, to enable manipulation thereof by a physician. For some embodiments, the length of the delivery apparatus 110 may be about 170 cm to about 200 cm. The core wire 114 may be made from any suitable high strength material such as stainless steel, NiTi alloy, or the like. Embodiments of the core wire 114 may have an outer diameter or transverse dimension of about 0.010 inch to about 0.015 inch. The over coil 132 may have an outer diameter or transverse dimension of about 0.018 inch to about 0.03 inch. Although the apparatus embodiment 110 shown in FIGS. 12-15 is activated by electrical energy passed through a conductor pair, a similar configuration that utilizes light energy passed through a fiber optic or any other suitable arrangement could be used to remotely heat a distal heating member or element such as the heater coil 124 to sever the distal portion of the tether 72. In addition, other delivery apparatus embodiments are discussed and incorporated herein that may also be used for any of the device embodiments 10 for treatment of a patient's vasculature discussed herein.

Other delivery and positioning system embodiments may provide for the ability to rotate a device for treatment of a patient's vasculature in-vivo without translating torque along the entire length of the delivery apparatus. Some embodiments for delivery and positioning of devices 10 are described in co-owned International PCT Patent Application No. PCT/US2008/065694. The delivery and positioning apparatus may include a distal rotating member that allows rotational positioning of the device. The delivery and positioning apparatus may include a distal rotating member that rotates an implant in-vivo without the transmission of torque along the entire length of the apparatus. Optionally, delivery system may also rotate the implant without the transmission of torque in the intermediate portion between the proximal end and the distal rotatable end. The delivery and positioning apparatus may be releasably secured to any suitable portion of the device for treatment of a patient's vasculature.

Device embodiments discussed herein may be releasable from any suitable flexible, elongate delivery apparatus or actuator such as a guidewire or guidewire-like structure. The release of device embodiments from such a delivery apparatus may be activated by a thermal mechanism, as discussed above, electrolytic mechanism, hydraulic mechanism, shape memory material mechanism, or any other mechanism known in the art of endovascular implant deployment.

Embodiments for deployment and release of therapeutic devices, such as deployment of embolic devices or stents within the vasculature of a patient, may include connecting such a device via a releasable connection to a distal portion of a pusher or other delivery apparatus member. The therapeutic device 10 may be detachably mounted to the distal portion of the apparatus by a filamentary tether 72, string, thread, wire, suture, fiber, or the like, which may be referred to above as the tether. The tether 72 may be in the form of a monofilament, rod, ribbon, hollow tube, or the like. Some embodiments of the tether may have a diameter or maximum thickness of between about 0.05 mm and 0.2 mm. The tether 72 may be configured to be able to withstand a maximum tensile load of between about 0.5 kg and 5 kg. For some embodiments, due to the mass of the device 10 being deployed which may be substantially greater than some embolic devices, some known detachment devices may lack sufficient tensile strength to be used for some embodiments discussed herein. As such, it may be desirable to use small very high strength fibers for some tether embodiments having a "load at break" greater than about 15 Newtons. For some embodiments, a tether made from a material known as Dyneema Purity® available from Royal DSM, Heerlen, Netherlands may be used.

The tether 72 may be severed by the input of energy such as electric current to a heating element causing release of the therapeutic device. For some embodiments, the heating element may be a coil of wire with high electrical resistivity such as a platinum-tungsten alloy. The tether member may pass through or be positioned adjacent the heater element. The heater may be contained substantially within the distal portion of the delivery apparatus to provide thermal insulation to reduce the potential for thermal damage to the surrounding tissues during detachment. In another embodiment, current may pass through the tether that also acts as a heating element.

Many materials may be used to make tether embodiments 72 including polymers, metals and composites thereof. One class of materials that may be useful for tethers includes polymers such as polyolefin, polyolefin elastomer such as polyethylene, polyester (PET), polyamide (Nylon), polyurethane, polypropylene, block copolymer such as PEBAX® or Hytrel®, and ethylene vinyl alcohol (EVA); or rubbery materials such as silicone, latex, and Kraton. In some cases, the polymer may also be cross-linked with radiation to manipulate its tensile strength and melt temperature. Another class of materials that may be used for tether embodiment may include metals such as nickel titanium alloy (Nitinol), gold, platinum, tantalum and steel. Other materials that may be useful for tether construction includes wholly aromatic polyester polymers which are liquid crystal polymers (LCP) that may provide high performance properties and are highly inert. A commercially available LCP polymer is Vectran®, which is produced by Kuraray Co. (Tokyo, Japan). The selection of the material may depend on the melting or softening temperature, the power used for detachment, and the body treatment site. The tether may be joined to the implant and/or the pusher by crimping, welding, knot tying, soldering, adhesive bonding, or other means known in the art.

Figure 16:
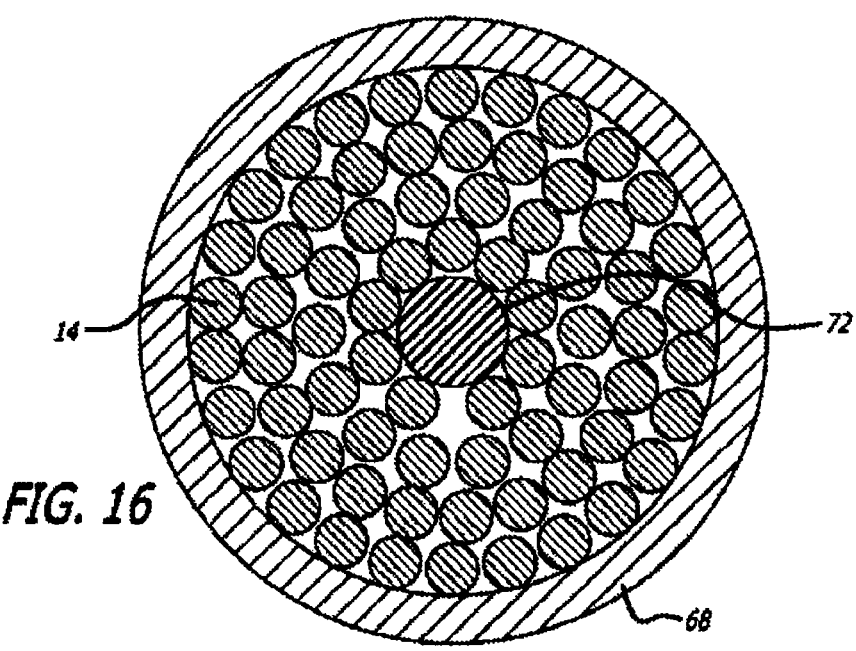
FIG. 16 illustrates an embodiment of a filament configuration for a device for treatment of a patient's vasculature.

It should be noted also that many variations of filament and proximal hub construction such as is detailed above with regard to FIG. 10 may be used for useful embodiments of a device for treatment of a patient's vasculature 10. FIG. 16 shows an enlarged view in transverse cross section of a proximal hub configuration. For the embodiment shown, the filaments 14 are disposed within a proximal hub 68 or end portion of the device 10 with the filaments 14 constrained and tightly packed by an outer ring of the proximal hub 68. A tether member 72 may be disposed within a middle portion of the filaments 14 or within a cavity of the proximal hub 68 proximal of the proximal ends 60 of the filaments 14. Such a tether 72 may be a dissolvable, severable or releasable tether that may be part of a release apparatus as discussed above used to deploy the device.

FIG. 16 illustrates in transverse cross section an embodiment of a proximal hub 68 showing the configuration of filaments which may be tightly packed and radially constrained by an inside surface of the proximal hub 68. In some embodiments, the braided or woven structure of the permeable shell 40 formed from such filaments 14 may be constructed using a large number of small filaments. The number of filaments 14 may be greater than 125 and may also be between about 80 filaments and about 180 filaments. As discussed above, the total number of filaments 14 for some embodiments may be about 70 filaments to about 300 filaments, more specifically, about 100 filaments to about 200 filaments. In some embodiments, the braided structure of the permeable shell 40 may be constructed with two or more sizes of filaments 14. For example, the structure may have several larger filaments that provide structural support and several smaller filaments that provide the desired pore size and density and thus flow resistance to achieve a thrombotic threshold velocity in some cases. For some embodiments, small filaments 50 of the permeable shell 40 may have a transverse dimension or diameter of about 0.0006 inches to about 0.002 inches for some embodiments and about 0.0004 inches to about 0.001 inches in other embodiments. The large filaments 48 may have a transverse dimension or diameter of about 0.0015 inches to about 0.004 inches in some embodiments and about 0.001 inches to about 0.004 inches in other embodiments. The filaments 14 may be braided in a plain weave that is one under, one over structure (shown in FIGS. 7 and 8) or a supplementary weave; more than one warp interlace with one or more than one weft. The pick count may be varied between about 25 and 200 picks per inch (PPI).

For some embodiments, the permeable shell 40 or portions thereof may be porous and may be highly permeable to liquids. In contrast to most vascular prosthesis fabrics or grafts which typically have a water permeability below 2,000 ml/min/cm$^2$ when measured at a pressure of 120 mmHg, the permeable shell 40 of some embodiments discussed herein may have a water permeability greater than about 2,000 ml/min/cm$^2$, in some cases greater than about 2,500 ml/min/cm$^2$. For some embodiments, water permeability of the permeable shell 40 or portions thereof may be between about 2,000 and 10,000 ml/min/cm$^2$, more specifically, about 2,000 ml/min/cm$^2$ to about 15,000 ml/min/cm$^2$, when measured at a pressure of 120 mmHg.

Device embodiments and components thereof may include metals, polymers, biologic materials and composites thereof. Suitable metals include zirconium-based alloys, cobalt-chrome alloys, nickel-titanium alloys, platinum, tantalum, stainless steel, titanium, gold, and tungsten. Potentially suitable polymers include but are not limited to acrylics, silk, silicones, polyvinyl alcohol, polypropylene, polyvinyl alcohol, polyesters (e.g., polyethylene terephthalate or PET), PolyEtherEther Ketone (PEEK), polytetrafluoroethylene (PTFE), polycarbonate urethane (PCU) and polyurethane (PU). Device embodiments may include a material that degrades or is absorbed or eroded by the body. A bioresorbable (e.g., breaks down and is absorbed by a cell, tissue, or other mechanism within the body) or bioabsorbable (similar to bioresorbable) material may be used. Alternatively, a bioerodable (e.g., erodes or degrades over time by contact with surrounding tissue fluids, through cellular activity or other physiological degradation mechanisms), biodegradable (e.g., degrades over time by enzymatic or hydrolytic action, or other mechanism in the body), or dissolvable material may be employed. Each of these terms is interpreted to be interchangeable. Potentially suitable bioabsorbable materials include polylactic acid (PLA), poly (alpha-hydroxy acid) such as poly-L-lactide (PLLA), poly-D-lactide (PDLA), polyglycolide (PGA), polydioxanone, polycaprolactone, polygluconate, polylactic acid-polyethylene oxide copolymers, modified cellulose, collagen, poly (hydroxybutyrate), polyanhydride, polyphosphoester, poly (amino acids), or related copolymer materials. An absorbable composite fiber may be made by combining a reinforcement fiber made from a copolymer of about 18% glycolic acid and about 82% lactic acid with a matrix material consisting of a blend of the above copolymer with about 20% polycaprolactone (PCL).

In any of the suitable device embodiments 10 discussed herein, the permeable shell structure 40, or any other suitable permeable shell structure discussed herein, may include one or more fixation elements or surfaces to facilitate fixation of the device within a blood vessel or other vascular site. The fixation elements may comprise hooks, barbs, protrusions, pores, micro-features, texturing, bioadhesives or combinations thereof. Embodiments of the support structure may be fabricated from a tube of metal where portions are removed. The removal of material may be done by laser, electrical discharge machining (EDM), photochemical etching and traditional machining techniques. In any of the described embodiments, the support structure may be constructed with a plurality of wires, cut or etched from a sheet of a material, cut or etched from a tube or a combination thereof as in the art of vascular stent fabrication.

Permeable shell embodiments 40 may be formed at least in part of wire, ribbon, or other filamentary elements 14. These filamentary elements 14 may have circular, elliptical, ovoid, square, rectangular, or triangular cross-sections. Permeable shell embodiments 40 may also be formed using conventional machining, laser cutting, electrical discharge machining (EDM) or photochemical machining (PCM). If made of a metal, it may be formed from either metallic tubes or sheet material. Permeable shell embodiments 40 may be heat formed to maintain their shape. In some embodiments, this may be done at a temperature of around 500° C.

Figure 17:
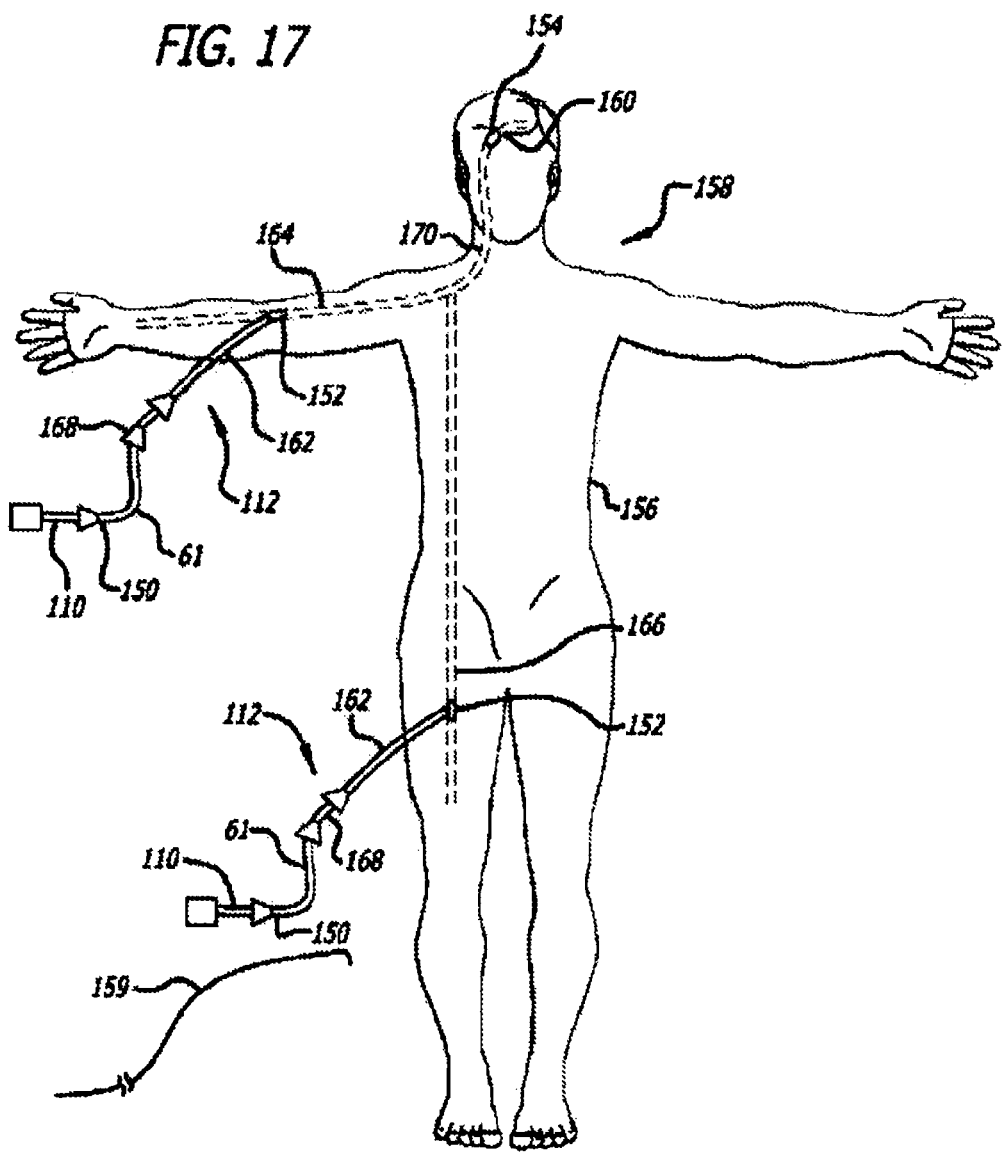
FIG. 17 is a schematic view of a patient being accessed by an introducer sheath, a microcatheter and a device for treatment of a patient's vasculature releasably secured to a distal end of a delivery device or actuator.
Figure 18:
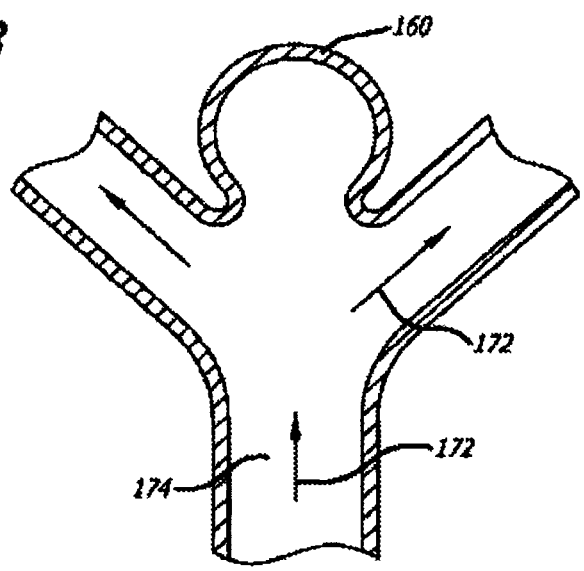
FIG. 18 is a sectional view of a terminal aneurysm.

Device embodiments 10 discussed herein may be delivered and deployed from a delivery and positioning system 112 that includes a microcatheter 61, such as the type of microcatheter 61 that is known in the art of neurovascular navigation and therapy. Device embodiments for treatment of a patient's vasculature 10 may be elastically collapsed and restrained by a tube or other radial restraint, such as an inner lumen 120 of a microcatheter 61, for delivery and deployment. The microcatheter 61 may generally be inserted through a small incision 152 accessing a peripheral blood vessel such as the femoral artery or brachial artery. The microcatheter 61 may be delivered or otherwise navigated to a desired treatment site 154 from a position outside the patient's body 156 over a guidewire 159 under fluoroscopy or by other suitable guiding methods. The guidewire 159 may be removed during such a procedure to allow insertion of the device 10 secured to a delivery apparatus 110 of the delivery system 112 through the inner lumen 120 of a microcatheter 61 in some cases. FIG. 17 illustrates a schematic view of a patient 158 undergoing treatment of a vascular defect 160 as shown in FIG. 18. An access sheath 162 is shown disposed within either a radial artery 164 or femoral artery 166 of the patient 158 with a delivery system 112 that includes a microcatheter 61 and delivery apparatus 110 disposed within the access sheath 162. The delivery system 112 is shown extending distally into the vasculature of the patient's brain adjacent a vascular defect 160 in the patient's brain.

Access to a variety of blood vessels of a patient may be established, including arteries such as the femoral artery 166, radial artery 164, and the like in order to achieve percutaneous access to a vascular defect 160. In general, the patient 158 may be prepared for surgery and the access artery is exposed via a small surgical incision 152 and access to the lumen is gained using the Seldinger technique where an introducing needle is used to place a wire over which a dilator or series of dilators dilates a vessel allowing an introducer sheath 162 to be inserted into the vessel. This would allow the device to be used percutaneously. With an introducer sheath 162 in place, a guiding catheter 168 is then used to provide a safe passageway from the entry site to a region near the target site 154 to be treated. For example, in treating a site in the human brain, a guiding catheter 168 would be chosen which would extend from the entry site 152 at the femoral artery up through the large arteries extending around the heart through the aortic arch, and downstream through one of the arteries extending from the upper side of the aorta such as the carotid artery 170. Typically, a guidewire 159 and neurovascular microcatheter 61 are then placed through the guiding catheter 168 and advanced through the patient's vasculature, until a distal end 151 of the microcatheter 61 is disposed adjacent or within the target vascular defect 160, such as an aneurysm. Exemplary guidewires 159 for neurovascular use include the Synchro2® made by Boston Scientific and the Glidewire® Gold Neuro made by MicroVention Terumo. Typical guidewire sizes may include 0.014 inches and 0.018 inches. Once the distal end 151 of the catheter 61 is positioned at the site, often by locating its distal end through the use of radiopaque marker material and fluoroscopy, the catheter is cleared. For example, if a guidewire 159 has been used to position the microcatheter 61, it is withdrawn from the catheter 61 and then the implant delivery apparatus 110 is advanced through the microcatheter 61.

Delivery and deployment of device embodiments 10 discussed herein may be carried out by first compressing the device 10, or any other suitable device for treatment of a patient's vasculature discussed herein, to a radially constrained and longitudinally flexible state as shown in FIG. 11. The device 10 may then be delivered to a desired treatment site 154 while disposed within the microcatheter 61, and then ejected or otherwise deployed from a distal end 151 of the microcatheter 61. In other method embodiments, the microcatheter 61 may first be navigated to a desired treatment site 154 over a guidewire 159 or by other suitable navigation techniques. The distal end of the microcatheter 61 may be positioned such that a distal port of the microcatheter 61 is directed towards or disposed within a vascular defect 160 to be treated and the guidewire 159 withdrawn. The device 10 secured to a suitable delivery apparatus 110 may then be radially constrained, inserted into a proximal portion of the inner lumen 120 of the microcatheter 61 and distally advanced to the vascular defect 160 through the inner lumen 120.

Once disposed within the vascular defect 160, the device 10 may then be allowed to assume an expanded relaxed or partially relaxed state with the permeable shell 40 of the device spanning or partially spanning a portion of the vascular defect 160 or the entire vascular defect 160. The device 10 may also be activated by the application of an energy source to assume an expanded deployed configuration once ejected from the distal section of the microcatheter 61 for some embodiments. Once the device 10 is deployed at a desired treatment site 154, the microcatheter 61 may then be withdrawn.

Figure 19:
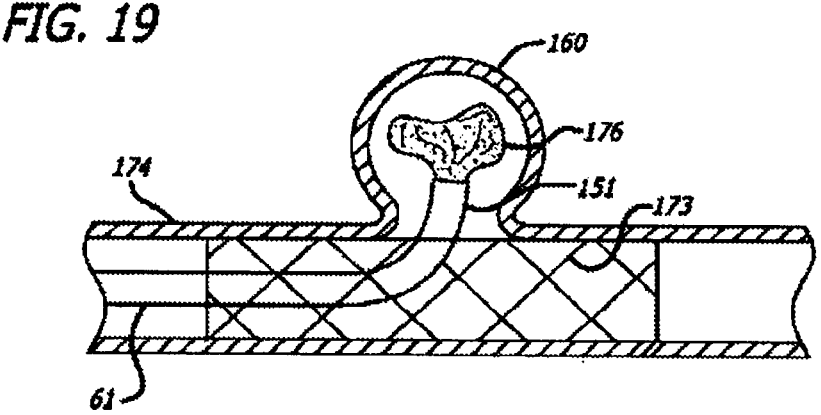
FIG. 19 is a sectional view of an aneurysm.

Some embodiments of devices for the treatment of a patient's vasculature 10 discussed herein may be directed to the treatment of specific types of defects of a patient's vasculature. For example, referring to FIG. 18, an aneurysm 160 commonly referred to as a terminal aneurysm is shown in section. Terminal aneurysms occur typically at bifurcations in a patient's vasculature where blood flow, indicated by the arrows 172, from a supply vessel splits into two or more branch vessels directed away from each other. The main flow of blood from the supply vessel 174, such as a basilar artery, sometimes impinges on the vessel where the vessel diverges and where the aneurysm sack forms. Terminal aneurysms may have a well-defined neck structure where the profile of the aneurysm 160 narrows adjacent the nominal vessel profile, but other terminal aneurysm embodiments may have a less defined neck structure or no neck structure. FIG. 19 illustrates a typical berry type aneurysm 160 in section where a portion of a wall of a nominal vessel section weakens and expands into a sack like structure ballooning away from the nominal vessel surface and profile. Some berry type aneurysms may have a well-defined neck structure as shown in FIG. 19, but others may have a less defined neck structure or none at all. FIG. 19 also shows some optional procedures wherein a stent 173 or other type of support has been deployed in the parent vessel 174 adjacent the aneurysm. Also, shown is embolic material 176 being deposited into the aneurysm 160 through a microcatheter 61. Either or both of the stent 173 and embolic material 176 may be so deployed either before or after the deployment of a device for treatment of a patient's vasculature 10.

Prior to delivery and deployment of a device for treatment of a patient's vasculature 10, it may be desirable for the treating physician to choose an appropriately sized device 10 to optimize the treatment results. Some embodiments of treatment may include estimating a volume of a vascular site or defect 160 to be treated and selecting a device 10 with a volume that is substantially the same volume or slightly over-sized relative to the volume of the vascular site or defect 160. The volume of the vascular defect 160 to be occluded may be determined using three-dimensional angiography or other similar imaging techniques along with software that calculates the volume of a selected region. The amount of over-sizing may be between about 2% and 15% of the measured volume. In some embodiments, such as a very irregular shaped aneurysm, it may be desirable to under-size the volume of the device 10. Small lobes or "daughter aneurysms" may be excluded from the volume, defining a truncated volume that may be only partially filled by the device without affecting the outcome. Such a method embodiment may also include implanting or deploying the device 10 so that the vascular defect 160 is substantially filled volumetrically by a combination of device and blood contained therein. The device 10 may be configured to be sufficiently conformal to adapt to irregular shaped vascular defects 160 so that at least about 75%, in some cases about 80%, of the vascular defect volume is occluded by a combination of device 10 and blood contained therein.

Figure 20:
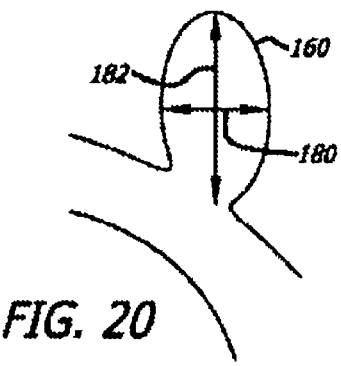
FIG. 20 is a schematic view in section of an aneurysm showing perpendicular arrows that indicate interior nominal longitudinal and transverse dimensions of the aneurysm.
Figure 21:
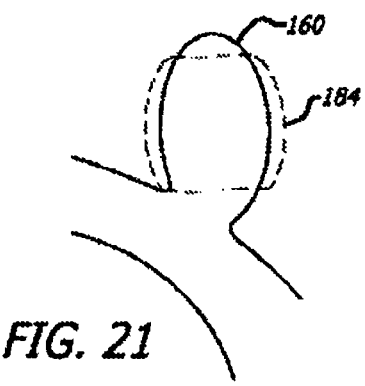
FIG. 21 is a schematic view in section of the aneurysm of FIG. 20 with a dashed outline of a device for treatment of a patient's vasculature in a relaxed unconstrained state that extends transversely outside of the walls of the aneurysm.
Figure 22:
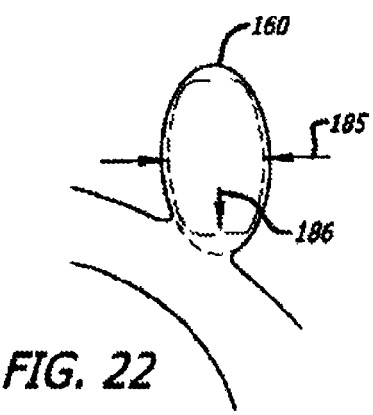
FIG. 22 is a schematic view in section of an outline of a device represented by the dashed line in FIG. 21 in a deployed and partially constrained state within the aneurysm.

In particular, for some treatment embodiments, it may be desirable to choose a device 10 that is properly oversized in a transverse dimension so as to achieve a desired conformance, radial force and fit after deployment of the device 10. FIGS. 20-22 illustrate a schematic representation of how a device 10 may be chosen for a proper fit after deployment that is initially oversized in a transverse dimension by at least about 10% of the largest transverse dimension of the vascular defect 160 and sometimes up to about 100% of the largest transverse dimension. For some embodiments, the device 10 may be oversized a small amount (e.g., less than about 1.5 mm) in relation to measured dimensions for the width, height or neck diameter of the vascular defect 160.

In FIG. 20, a vascular defect 160 in the form of a cerebral aneurysm is shown with horizontal arrows 180 and vertical arrows 182 indicating the approximate largest interior dimensions of the defect 160. Arrow 180 extending horizontally indicates the largest transverse dimension of the defect 160. In FIG. 21, a dashed outline 184 of a device for treatment of the vascular defect 10 is shown superimposed over the vascular defect 160 of FIG. 20 illustrating how a device 10 that has been chosen to be approximately 20% oversized in a transverse dimension would look in its unconstrained, relaxed state. FIG. 22 illustrates how the device 10 which is indicated by the dashed line 184 of FIG. 21 might conform to the interior surface of the vascular defect 160 after deployment whereby the nominal transverse dimension of the device 10 in a relaxed unconstrained state has now been slightly constrained by the inward radial force 185 exerted by the vascular defect 160 on the device 10. In response, as the filaments 14 of the device 10 and thus the permeable shell 40 made therefrom have a constant length, the device 10 has assumed a slightly elongated shape in the axial or longitudinal axis of the device 10 so as to elongate and better fill the interior volume of the defect 160 as indicated by the downward arrow 186 in FIG. 22.

Figure 23:
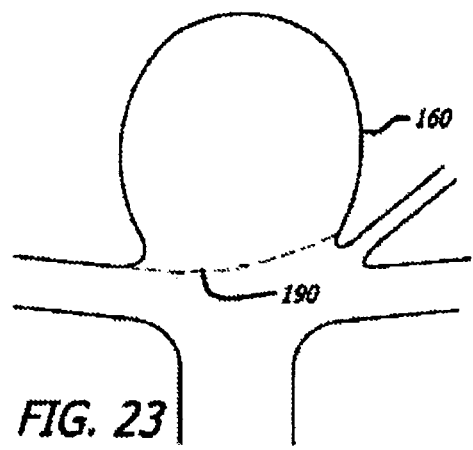
FIGS. 23-26 show a deployment sequence of a device for treatment of a patient's vasculature.
Figure 24:
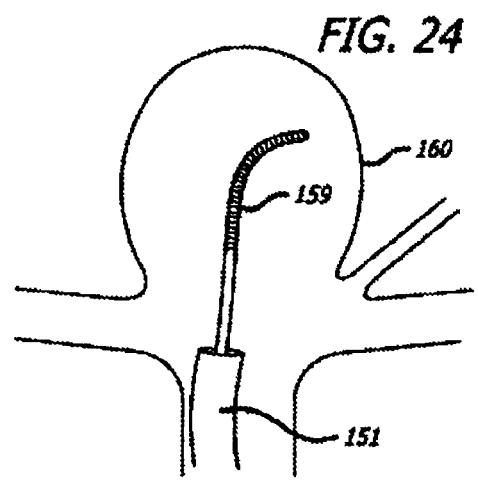

Once a properly sized device 10 has been selected, the delivery and deployment process may then proceed. It should also be noted also that the properties of the device embodiments 10 and delivery system embodiments 112 discussed herein generally allow for retraction of a device 10 after initial deployment into a defect 160, but before detachment of the device 10. Therefore, it may also be possible and desirable to withdraw or retrieve an initially deployed device 10 after the fit within the defect 160 has been evaluated in favor of a differently sized device 10. An example of a terminal aneurysm 160 is shown in FIG. 23 in section. The tip 151 of a catheter, such as a microcatheter 61 may be advanced into or adjacent the vascular site or defect 160 (e.g., aneurysm) as shown in FIG. 24. For some embodiments, an embolic coil or other vaso-occlusive device or material 176 (as shown for example in FIG. 19) may optionally be placed within the aneurysm 160 to provide a framework for receiving the device 10. In addition, a stent 173 may be placed within a parent vessel 174 of some aneurysms substantially crossing the aneurysm neck prior to or during delivery of devices for treatment of a patient's vasculature discussed herein (also as shown for example in FIG. 19). An example of a suitable microcatheter 61 having an inner lumen diameter of about 0.020 inches to about 0.022 inches is the Rapid Transit® manufactured by Johnson & Johnson. Examples of some suitable microcatheters 61 may include microcatheters having an inner lumen diameter of about 0.026 inch to about 0.028 inch, such as the Rebar® by Covidien, the Renegade Hi-Flow® by Boston Scientific Corporation, and the Mass Transit™ by Johnson & Johnson. Suitable microcatheters having an inner lumen diameter of about 0.031 inch to about 0.033 inch may include the Marksman™ by Covidien and the Vasco 28™ by Balt Extrusion. A suitable microcatheter 61 having an inner lumen diameter of about 0.039 inch to about 0.041 inch includes the Vasco 35 by Balt Extrusion. These microcatheters 61 are listed as exemplary embodiments only, other suitable microcatheters may also be used with any of the embodiments discussed herein.

Figure 25:
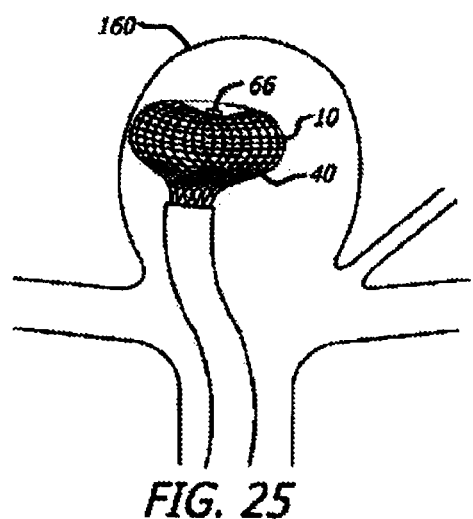

Detachment of the device 10 from the delivery apparatus 110 may be controlled by a control switch 188 disposed at a proximal end of the delivery system 112, which may also be coupled to an energy source 142, which severs the tether 72 that secures the proximal hub 68 of the device 10 to the delivery apparatus 110. While disposed within the microcatheter 61 or other suitable delivery system 112, as shown in FIG. 11, the filaments 14 of the permeable shell 40 may take on an elongated, non-everted configuration substantially parallel to each other and a longitudinal axis of the catheter 61. Once the device 10 is pushed out of the distal port of the microcatheter 61, or the radial constraint is otherwise removed, the distal ends 62 of the filaments 14 may then axially contract towards each other so as to assume the globular everted configuration within the vascular defect 160 as shown in FIG. 25.

The device 10 may be inserted through the microcatheter 61 such that the catheter lumen 120 restrains radial expansion of the device 10 during delivery. Once the distal tip or deployment port of the delivery system 112 is positioned in a desirable location adjacent or within a vascular defect 160, the device 10 may be deployed out the distal end of the catheter 61 thus allowing the device to begin to radially expand as shown in FIG. 25. As the device 10 emerges from the distal end of the delivery system 112, the device 10 expands to an expanded state within the vascular defect 160, but may be at least partially constrained by an interior surface of the vascular defect 160.

Figure 26:
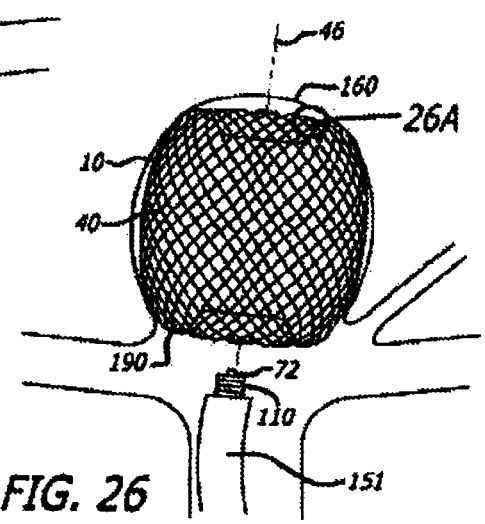

Upon full deployment, radial expansion of the device 10 may serve to secure the device 10 within the vascular defect 160 and also deploy the permeable shell 40 across at least a portion of an opening 190 (e.g., aneurysm neck) so as to at least partially isolate the vascular defect 160 from flow, pressure or both of the patient's vasculature adjacent the vascular defect 160 as shown in FIG. 26. The conformability of the device 10, particularly in the neck region 190 may provide for improved sealing.

For some embodiments, once deployed, the permeable shell 40 may substantially slow flow of fluids and impede flow into the vascular site and thus reduce pressure within the vascular defect 160. For some embodiments, the device 10 may be implanted substantially within the vascular defect 160, however, in some embodiments, a portion of the device 10 may extend into the defect opening or neck 190 or into branch vessels.

Once the device 10 has been deployed in the vascular defect, the isolation of the defect, slowing of flow, reduce pressure or any combination of these effects may case thrombus formation within an interior volume of the device 10, outside the device 10 or on the device itself or some component thereof. In some cases, device embodiments for treatment of a patient's vasculature 10 may generally be fabricated by braiding a substantially tubular braided structure with filamentary elements 14, forming the braided tubular structure into a desired shape, and heat setting the braided formed filaments into the desired shape. Once so formed, the ends of the elongate resilient filaments 14 may then be secured together relative to each other by any of the methods discussed above and proximal and distal hubs 66 and 68 added.

Figure 27:
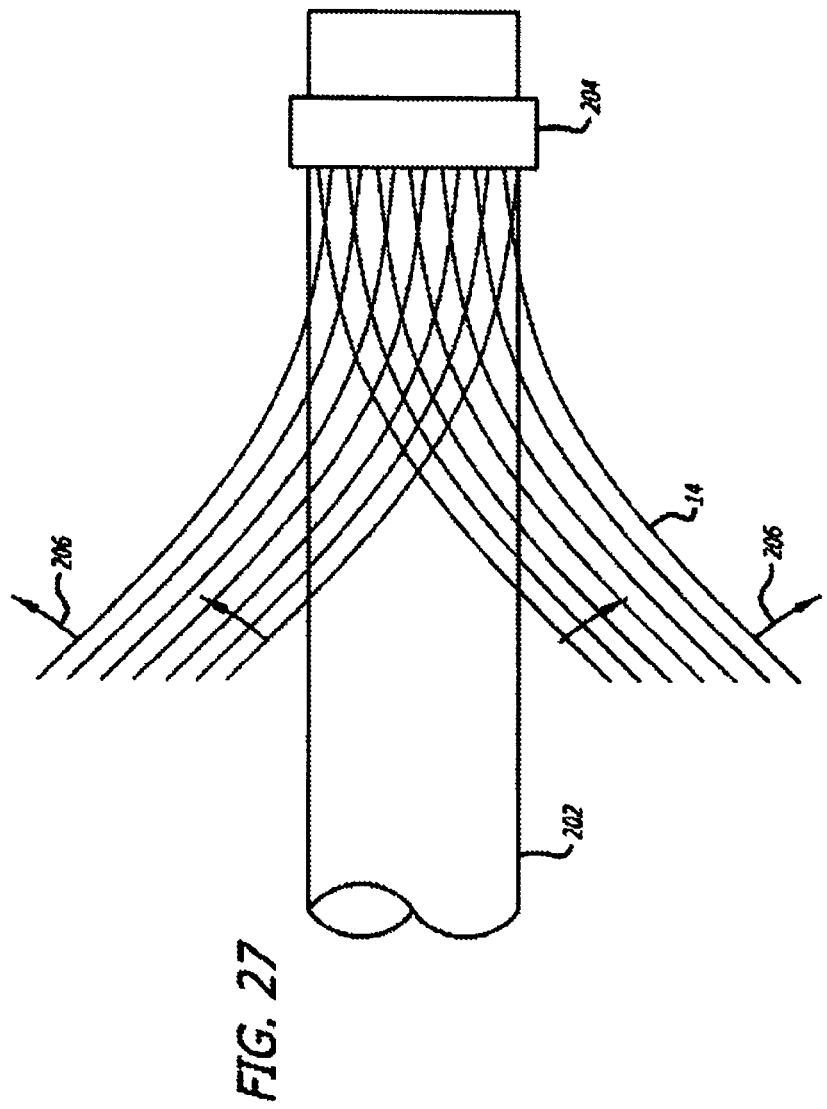
FIG. 27 is an elevation view of a mandrel used for manufacture of a braided tubular member for construction of an embodiment of a device for treatment of a patient's vasculature with the initiation of the braiding process shown.
Figure 28:
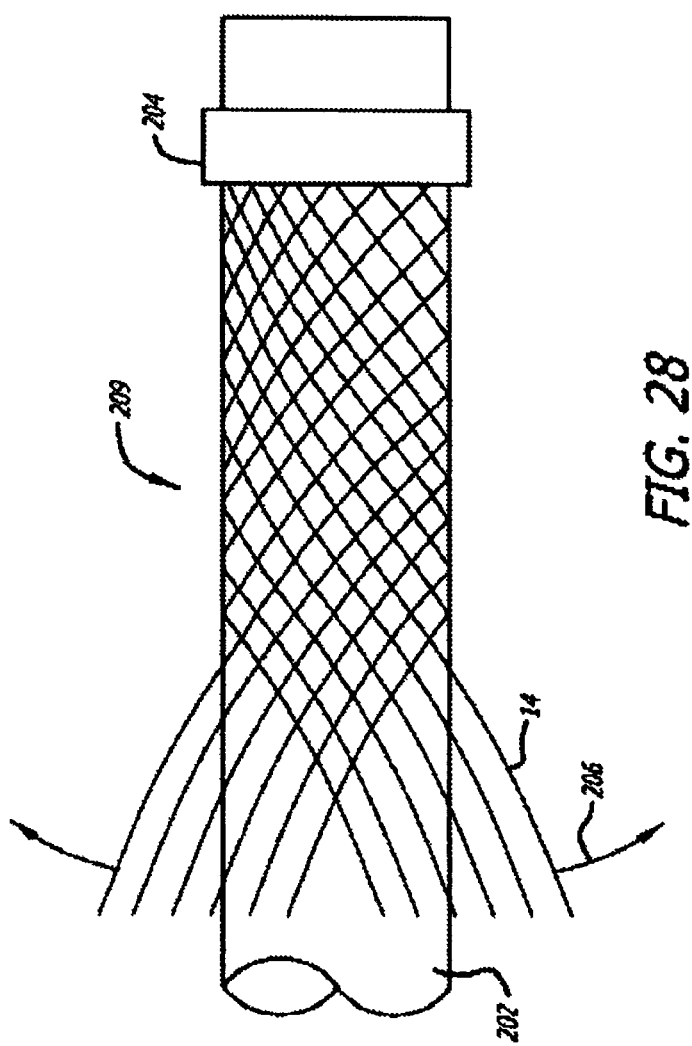
FIG. 28 is an elevation view of a braiding process for a braided tubular member used for manufacture of a device.

Such a braiding process may be carried out by automated machine fabrication or may also be performed by hand. An embodiment of a process for braiding a tubular braided structure by a manual process is shown in FIG. 27. A plurality of elongate resilient filaments 14 are secured at one end of an elongate cylindrical braiding mandrel 202 by a constraining band 204. The band 204 may include any suitable structure that secured the ends of the filaments 14 relative to the mandrel 202 such as a band of adhesive tape, an elastic band, an annular clamp or the like. The loose ends of the filaments 14 opposite the secured ends are being manipulated in a braided or woven pattern as indicated by the arrows 206 to achieve a one over-one under braid pattern for generation of a braided tubular member 208. As discussed above, although a one over-one under simple braid pattern is shown and discussed, other braid or weave patterns may also be used. One such example of another braid configuration may include a two over-one under pattern. FIG. 28 illustrates the braided tubular member 208 taking shape and lengthening as the braiding process continues as indicated by the arrows 206 in FIG. 28. Once the braided tubular member 208 achieves sufficient length, it may be removed from the braiding mandrel 202 and positioned within a shaping fixture such as the shaping fixture embodiments shown in FIGS. 29 and 30.

Figure 29:
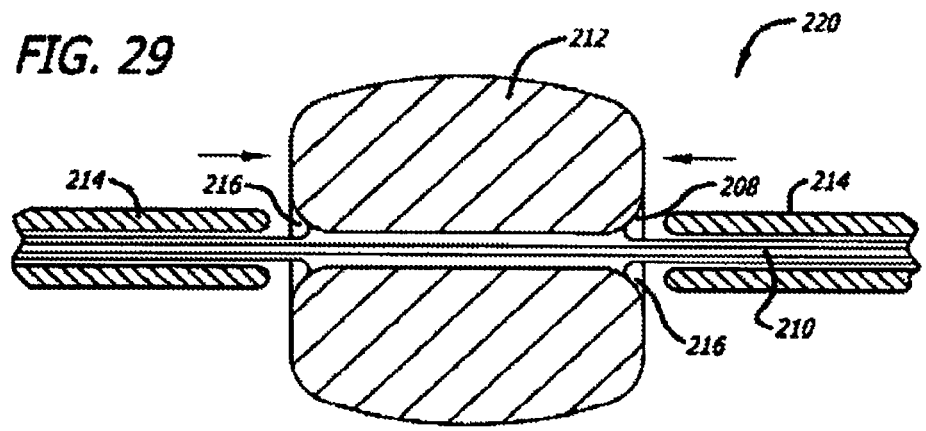
FIG. 29 is an elevation view in partial section of an embodiment of a fixture for heat setting a braided tubular member for manufacture of a device for treatment of a patient's vasculature.

FIG. 29 shows the tubular braided member 208 disposed over an internal rod mandrel 210 that extends through central lumens of an internal ball mandrel 212 and a pair of opposed recessed end forming mandrels 214. The tubular braided member 208 is also disposed over an outer surface of the internal ball mandrel 212 and within an inner lumen of each of the end forming mandrels 214. In order to hold the braided tubular member 208 onto an outer surface contour of the internal ball mandrel 212, including the recessed ends 216 thereof, the end forming mandrels 214 are configured to be pushed against and into the recessed ends 216 of the internal ball mandrel 212 such that the inside surface of the braided tubular member 208 is held against the outer contour of the internal ball mandrel 212 and fixed in place. This entire fixture 220 with the inside surface of the braided tubular structure 208 held against the outside surface of the internal ball mandrel 212 may then be subjected to an appropriate heat treatment such that the resilient filaments 14 of the braided tubular member 208 assume or are otherwise shape-set to the outer contour of the central ball mandrel 212. In some embodiments, the filamentary elements 14 of the permeable shell 40 may be held by a fixture configured to hold the permeable shell 40 in a desired shape and heated to about 475-525 degrees C. for about 5-10 minutes to shape-set the structure.

The central ball mandrel 212 may be configured to have any desired shape so as to produce a shape set tubular braided member 208 that forms a permeable shell 40 having a desired shape and size such as the globular configuration of the device 10 of FIGS. 3-6 above, or any other suitable configuration. As such, the central ball mandrel 212 may also be a globular-shaped ball with recesses in opposing sides for the hubs 66 and 68 that is placed inside the tubular braid 208. A mold or molds that have one or more pieces that are assembled to form a cavity with the desired device shape may also be used in conjunction with or in place of the end forming mandrels 214. Once the heat set process is complete, fibers, coatings, and/or surface treatments may be added to certain filaments, portions of filaments, or all of the permeable shell 40 structure that results. Further, for some embodiments of device processing, the permeable shell 40 may be formed as discussed above by securing proximal ends 60 and distal ends 62 of elongate filamentary elements 14, or to respective proximal and distal hubs 66 and 68.

Figure 30:
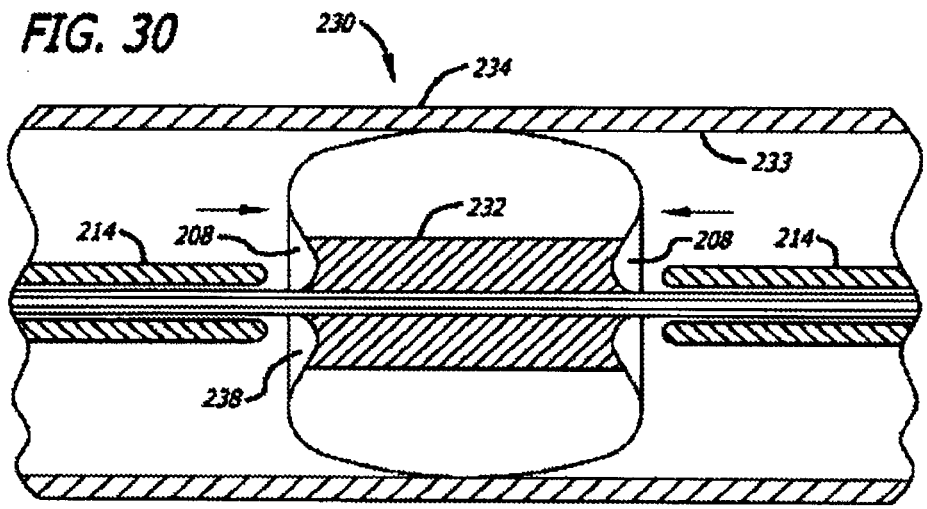
FIG. 30 is an elevation view in partial section of an embodiment of a fixture for heat setting a braided tubular member for manufacture of a device for treatment of a patient's vasculature.

FIG. 30 shows another embodiment of a fixture for shape setting the permeable shell 40 of a device for treatment of a patient's vasculature. The fixture embodiment 230 of FIG. 30 may be used in essentially the same manner as the fixture embodiment 220 of FIG. 29, except that instead of a central ball mandrel 212, an internal tube mandrel 232 is used in conjunction with an external tube restraint 234 in order to hold the shape of the braided tubular member 208 during the heat setting process. More specifically, the tubular braided member 208 is disposed over an internal rod mandrel 210 that extends through central lumens of the internal tube mandrel 232 and a pair of opposed recessed end forming mandrels 214. The tubular braided member 208 is also disposed over an outer surface of the internal tube mandrel 232 and within an inner lumen of each of the end forming mandrels 214.

In order to hold the braided tubular member 208 into a desired shape, including the recessed ends thereof, the end forming mandrels 214 are configured to be pushed against and into recessed ends 238 of the internal tube mandrel 232 such that the inside surface of the braided tubular member 208 is held against the outer contour of the internal tube mandrel 232 and fixed in place at the ends of the tube mandrel 232.

Between the ends of the tube mandrel 232, the braided tubular member 208 radially expands outwardly until it touches and is radially constrained by an inside surface of an external tube mandrel 234. The combination of axial restraint and securement of the braided tubular member 208 at the ends of the internal tube mandrel 232 in conjunction with the inward radial restraint on an outside surface of the braided tubular member 208 disposed between the proximal and distal ends thereof, may be configured to produce a desired globular configuration suitable for the permeable shell 40 of the device 10.

Once again, this entire fixture 230 with the inside surface of the ends of the braided tubular structure 208 held against the outside surface of the ends of the internal tube mandrel 232 and an outside surface of the braided tubular member 208 radially constrained by an inside surface 233 of the external tube member 234, may then be subjected to an appropriate heat treatment. The heat treatment may be configured such that the resilient filaments 14 of the braided tubular member 208 assume or are otherwise shape-set to the globular contour of the filaments 14 generated by the fixture 230. In some embodiments, the filamentary elements 14 of the permeable shell 40 may be held by a fixture configured to hold the braided tubular member 208 in a desired shape and heated to about 475-525 degrees C. for about 5-10 minutes to shape-set the structure. The internal tube mandrel 232 and inside surface 233 of the external tube member 234 may be so configured to have any desired shape so as to produce a shape set tubular braided member 208 that forms a permeable shell 40 having a desired shape and size such as the globular configuration of the device of FIGS. 3-6 above, or any other suitable configuration.

For some embodiments, material may be attached to filaments 14 of the permeable shell 40 of a device 10 such that it substantially reduces the size of the fenestrations, cells or pores 64 between filaments 14 and thus reduces the porosity in that area. For example, coating embodiments may be disposed on portions of the filaments 14 to create small fenestrations or cells and thus higher density of the permeable shell 40. Active materials such as a responsive hydrogel may be attached or otherwise incorporated into permeable shell 40 of some embodiments such that it swells upon contact with liquids over time to reduce the porosity of the permeable shell 40.

Device embodiment 10 and any other suitable device embodiment discussed herein may be coated with various polymers to enhance its performance, fixation and/or biocompatibility. In addition, device embodiments 10 may be made of various biomaterials known in the art of implant devices including but not limited to polymers, metals, biological materials and composites thereof. Device embodiments discussed herein may include cells and/or other biologic material to promote healing. Device embodiments discussed herein may also be constructed to provide the elution or delivery of one or more beneficial drugs, other bioactive substances or both into the blood or the surrounding tissue.

In some cases, permeable shell embodiments 40 of devices for treatment of a patient's vasculature 10 may include multiple layers. A first or outer layer may be constructed from a material with low bioactivity and hemocompatibility so as to minimize platelet aggregation or attachment and thus the propensity to form clot and thrombus. Optionally, an outer layer may be coated or incorporate an antithrombogenic agent such as heparin or other antithrombogenic agents described herein or known in the art. One or more inner layers disposed towards the vascular defect in a deployed state relative to the first layer may be constructed of materials that have greater bioactivity and/or promote clotting and thus enhance the formation of an occlusive mass of clot and device within the vascular defect. Some materials that have been shown to have bioactivity and/or promote clotting include silk, polylactic acid (PLA), polyglycolic acid (PGA), collagen, alginate, fibrin, fibrinogen, fibronectin, Methylcellulose, gelatin, Small Intestinal Submucosa (SIS), poly-N-acetylglucosamine and copolymers or composites thereof.

Bioactive agents suitable for use in the embodiments discussed herein may include those having a specific action within the body as well as those having nonspecific actions. Specific action agents are typically proteinaceous, including thrombogenic types and/or forms of collagen, thrombin and fibrogen (each of which may provide an optimal combination of activity and cost), as well as elastin and von Willebrand factor (which may tend to be less active and/or expensive agents), and active portions and domains of each of these agents. Thrombogenic proteins typically act by means of a specific interaction with either platelets or enzymes that participate in a cascade of events leading eventually to clot formation. Agents having nonspecific thrombogenic action are generally positively charged molecules, e.g., polymeric molecules such as chitosan, polylysine, poly(ethylenimine) or acrylics polymerized from acrylimide or methacrylamide which incorporate positively-charged groups in the form of primary, secondary, or tertiary amines or quaternary salts, or non-polymeric agents such as (tridodecylmethylammonium chloride). Positively charged hemostatic agents promote clot formation by a non-specific mechanism, which includes the physical adsorption of platelets via ionic interactions between the negative charges on the surfaces of the platelets and the positive charges of the agents themselves.

Device embodiment 10 and any other suitable device embodiment discussed herein may include a surface treatment or coating on a portion, side or all surfaces that promotes or inhibits thrombosis, clotting, healing or other embolization performance measure. The surface treatment or coating may be a synthetic, biologic or combination thereof. For some embodiments, at least a portion of an inner surface of the permeable shell 40 may have a surface treatment or coating made of a biodegradable or bioresorbable material such as a polylactide, polyglycolide or a copolymer thereof. Another surface treatment or coating material that may enhance the embolization performance of a device includes a polysaccharide such as an alginate based material. Some coating embodiments may include extracellular matrix proteins such as ECM proteins. One example of such a coating may be Finale™ Prohealing coating which is commercially available from Surmodics Inc., Eden Prairie, Minn. Another exemplary coating may be Polyzene-F, which is commercially available from CeloNovo BioSciences, Inc., Newnan, Ga. In some embodiments, the coatings may be applied with a thickness that is less than about 25% of a transverse dimension of the filaments 14.

Antiplatelet agents may include aspirin, glycoprotein IIb/IIIa receptor inhibitors (including, abciximab, eptifibatide, tirofiban, lamifiban, fradafiban, cromafiban, toxifiban, XV454, lefradafiban, klerval, lotrafiban, orbofiban, and xemilofiban), dipyridamole, apo-dipyridamole, persantine, prostacyclin, ticlopidine, clopidogrel, cromafiban, cilostazol, and nitric oxide. To deliver nitric oxide, device embodiments may include a polymer that releases nitric oxide. Device embodiments 10 may also deliver or include an anticoagulant such as heparin, low molecular weight heparin, hirudin, warfarin, bivalirudin, hirudin, argatroban, forskolin, ximelagatran, vapiprost, prostacyclin and prostacyclin analogues, dextran, synthetic antithrombin, Vasoflux, argatroban, efegatran, tick anticoagulant peptide, Ppack, HMG-CoA reductase inhibitors, and thromboxane A2 receptor inhibitors.

In some embodiments, the permeable shell 40 of a device 10 may be coated with a composition that may include nanoscale structured materials or precursors thereof (e.g., self-assembling peptides). The peptides may have with alternating hydrophilic and hydrophobic monomers that allow them to self-assemble under physiological conditions. The composition may comprise a sequence of amino acid residues. In some embodiments, the permeable shell may include a thin metallic film material. The thin film metal may be fabricated by sputter deposition and may be formed in multiple layers. The thin film may be a nickel-titanium alloy also known as nitinol.

Figure 31:
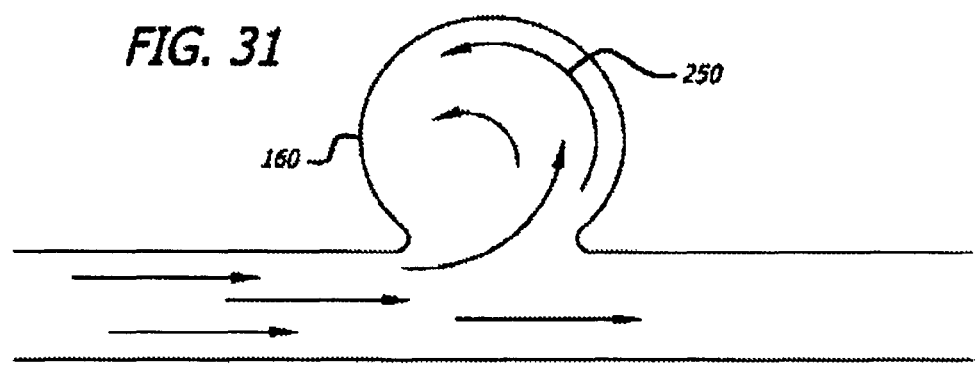
FIG. 31 is an elevation view in section that illustrates a flow of blood within an aneurysm of a patient's vasculature.

In some instances, saccular aneurysms may have a generally circular flow dynamic of blood as indicated by arrows 250 shown in FIG. 31. While the shell of a single layer device, such as device 10, slows flow into the aneurysm, thrombosis and embolization may be further enhanced by an internal porous structure. In particular, a structure that is formed so that the circular flow 250, and in particular the highest velocity region is forced to pass through one or more porous layers may have a synergistic treatment effect and promote rapid thrombosis.

As discussed above with regard to the deployment method embodiment shown in FIGS. 23-26, once a properly sized device for treatment of a patient's vasculature 10 has been selected, the delivery and deployment process may take place. During deployment, the tip of a microcatheter 61 may be advanced into or adjacent the vascular site or defect 160. The device for treatment of a patient's vasculature 10 may be inserted through the microcatheter 61 such that the catheter lumen restrains radial expansion of the device during delivery. Once the distal tip or deployment port of the delivery system is positioned in a desirable location adjacent or within a vascular defect 160, the device 10 may be deployed out the distal end of the catheter thus allowing the device to begin to radially expand as shown in FIG. 25. As the device emerges from the distal end of the delivery system, the device 10 expands radially outward to an expanded state within an interior volume the vascular defect. Upon deployment, the device 10 may also be at least partially constrained by an interior surface of the vascular defect 160 depending on the sizing of the device relative to the size of the interior surface of the vascular defect 160. Upon full deployment, radial expansion of the device 10 may serve to exert an outward radial force of the outside surface of the device against the inside surface of the vascular defect to mechanically secure the device within the vascular defect. Deployment of the device 10 may serve to partially isolate the vascular defect from flow, pressure or both coming from the patient's vasculature adjacent the vascular defect.

In any of the device embodiments discussed or incorporated herein for treatment of a patient's vascular defect or aneurysm, the device may comprise one or more composite filaments. A composite filament (e.g., wires) may be defined as a filament that comprises a plurality of materials in either a mixture or alloy or in a composite structure where two materials are physically combined into one. The addition of at least some composite wires into the device may provide improved visibility of the device under external imaging such as x-ray, fluoroscopy, magnetic resonance imaging and the like. In some embodiments, composite wires may provide improved mechanical characteristics.

Figure 32:
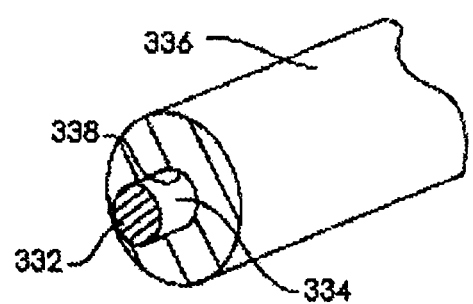
FIG. 32 is a perspective view in section of a of a composite filament embodiment.

For some composite filament embodiments, the composite filaments may be disposed in a coaxial arrangement with one material substantially inside the other as shown in FIG. 32. One known method of fabrication of such a coaxial composite wire is a drawn filled tube wire wherein the materials of the drawn filled tube are combined but retain their individual mechanical properties. Drawn filled tube wires are commercially available from Ft. Wayne Metals, Ft. Wayne, Indiana. In some cases, the process for producing drawn filled tube filaments may include extreme compressive forces such that the mechanical bond between an outer surface 334 of the internal fill wire 332 and an internal surface 338 of the external tube 336 is metallurgically sound. In some instances, a plurality of external tubes, each of a different material, may be layered over the internal wire and each other in order to combine the mechanical properties of the plurality of materials. For such embodiments, the drawn filled tube filament may include 2, 3, 4, 5 or more external tube layers. In some embodiments, the drawn filled tube wires are formed of a combination of an external nitinol (NiTi) tube and a highly radiopaque fill wire that may be concentrically disposed within the external tube. Various radiopaque materials and metals known in the art may be used as the fill wire including but not limited to gold, platinum, tantalum and the like. One advantage of a composite with a NiTi exterior and internal highly radiopaque fill wire is that the device can substantially maintain its highly elastic or superelastic behavior and the majority of the blood contacting surfaces remain nitinol. This allows for a device with substantially improved visibility under x-ray imaging while maintaining the proper range of mechanical characteristics.

In some cases, the specific construction of a drawn filled tube wire or filament may be important in order to maintain desired performance characteristics of a device for treatment of a vascular defect. More specifically, it may be important to balance the stiffness, elasticity and radiopacity of the composition. In particular, for drawn filled tube filament embodiments that include an internal wire 332 of ductile radiopaque material such as platinum and an outer tube 336 of an elastic or superelastic material such as NiTi, it can be necessary to carefully balance the ratio of the percent cross sectional area of the internal wire with regard to the overall cross sectional area of the filament. Such a ratio may be referred to as a fill ratio. If an embodiment includes too little radiopaque or highly radiopaque internal tube material relative to the external tube material, there may not be sufficient radiopacity and visibility. On the other hand, if an embodiment includes too much internal wire material with respect to the elastic external tube, the mechanical properties of the ductile radiopaque material may overwhelm the elastic properties of the outer tube material and the filaments may be prone to taking a set after compression etc. resulting in permanent deformation. For some embodiments, a desired composite or drawn filled tube wire may be constructed with a fill ratio of cross sectional area of internal fill wire to cross sectional area of the entire composite filament of between about 10% and about 50%, more specifically between about 20% and about 40%, and even more specifically, between about 25% and about 35%.

In some embodiments, the number of composite wires may be between about 40 and 190, and between about 50 and 190 in other embodiments, and between about 70 and 150 in other embodiments. In some embodiments, the devices for treatment of a patient's vasculature may have at least about 25% composite wires relative to the total number of wires and in some embodiments such devices may have at least about 40% composite wires relative to a total number of wires in the device. For example, a first subset of elongate resilient filaments may comprise filaments, each having a composite of highly radiopaque material and a high strength material, and a second subset of elongate resilient filaments may consist essentially of a high strength material. For example, the highly radiopaque material may comprise platinum, platinum alloy such as 90% platinum/10% iridium, or gold or tantalum. The high strength material may comprise NiTi. While composite wires may provide enhanced visualization and/or mechanical characteristics, they may in some configurations have reduced tensile strength in comparison to NiTi wires of a similar diameter. In other configurations, depending on their diameter, the composite wires may increase the collapsed profile of the devices. Therefore, it may be beneficial to minimize the number. Lower percentages of composite wires may not be sufficiently visible with current imaging equipment particularly in neurovascular applications where the imaging is done through the skull. In addition, too many composite wires (or composite wires with extremely high fill ratios) may result in devices with excessive artifact on CT or MRI imaging. The described ratios and amounts of highly radiopaque material provide a unique situation for neurovascular implants where the periphery of the device is just visible under transcranial fluoroscopy but the device imaged area is not completely obliterated (i.e., due to artifact) as it is with conventional embolic coils that are made substantially out of platinum or platinum alloys.

One manner of achieving the desired degree of radiopacity is by selecting a particular combination of fill ratio of the composite wires and the percent of composite wires in relation to the total number of wires. Devices according to embodiments having a single layer braided (woven) structure were constructed. For example, an embodiment of a braided structure comprising 72 composite Platinum/NiTi drawn filled tube wires having a 0.00075" diameter and a platinum fill ratio of 30% and 72 NiTi wires having a 0.00075" diameter was constructed. The total percent of platinum (by total % cross sectional area) in the braided structure was about 15%. Another embodiment of a braided structure comprising 108 composite Platinum/NiTi drawn filled tube wires having a 0.001" diameter and a platinum fill ratio of 30% and 72 NiTi wires having a 0.00075" diameter was constructed. The total percent of platinum in the braided structure was about 22%. Still another embodiment of a braided structure comprising 72 composite Platinum/NiTi drawn filled tube wires having a 0.00125" diameter and a platinum fill ratio of 30% and 108 NiTi wires having a 0.00075" diameter was constructed. The total percent of platinum in the braided structure was about 19.5%. Yet another embodiment of a braided structure comprising 108 composite Platinum/NiTi drawn filled tube wires having a 0.00125" diameter and a platinum fill ratio of 30% and 108 NiTi wires having a 0.00075" diameter was constructed. The total percent of platinum in the braided structure was about 22%. Devices constructed according to each of these embodiments were each implanted into living bodies and imaged using fluoroscopy. In each case, the periphery of the device was visible under transcranial fluoroscopy but the device imaged area was not completely obliterated (i.e., due to artifact).

In some embodiments the total cross sectional area of the highly radiopaque material is between about 11% and about 30% of the total cross sectional area of the plurality of elongate elements. In some embodiments the total cross sectional area of the highly radiopaque material is between about 15% and about 30% of the total cross sectional area of the plurality of elongate elements. In some embodiments the total cross sectional area of the highly radiopaque material is between about 15% and about 22% of the total cross sectional area of the plurality of elongate elements. In some embodiments the total cross sectional area of the highly radiopaque material is between about 19% and about 30% of the total cross sectional area of the plurality of elongate elements. In some embodiments the total cross sectional area of the highly radiopaque material is between about 11% and about 18.5% of the total cross sectional area of the plurality of elongate elements.

Because the radiopacity of the composite filaments comprising a highly radiopaque material can allow sufficient device visualization (e.g., on fluoroscopy), it may be desired to make one or more of the hubs from less radiopaque or non-radiopaque materials. In some embodiments, platinum, platinum alloy (e.g., 90% Platinum/10% Iridium), may not be desired, if their radiopacity would overpower the radiopacity of the composite filaments, and thus, make their delineation difficult. The use of less radiopaque or non-radiopaque materials to make the hubs may thus be desired in these embodiments, but can also be used on the hubs of other embodiments. One or more titanium or titanium alloy hubs or NiTi hubs may be used in place of highly radiopaque hubs. The use of titanium, titanium alloy, or NiTi hubs may also aid in welding to NiTi filaments, as their melt temperatures are more closely matched than if, for example, platinum, platinum alloy, or gold hubs were being used. The result can be a joint between the filaments and the hub that has a higher tensile breakage force. Joints of this variety were constructed and demonstrated an approximately 48% improvement in tensile force.

Figure 33:
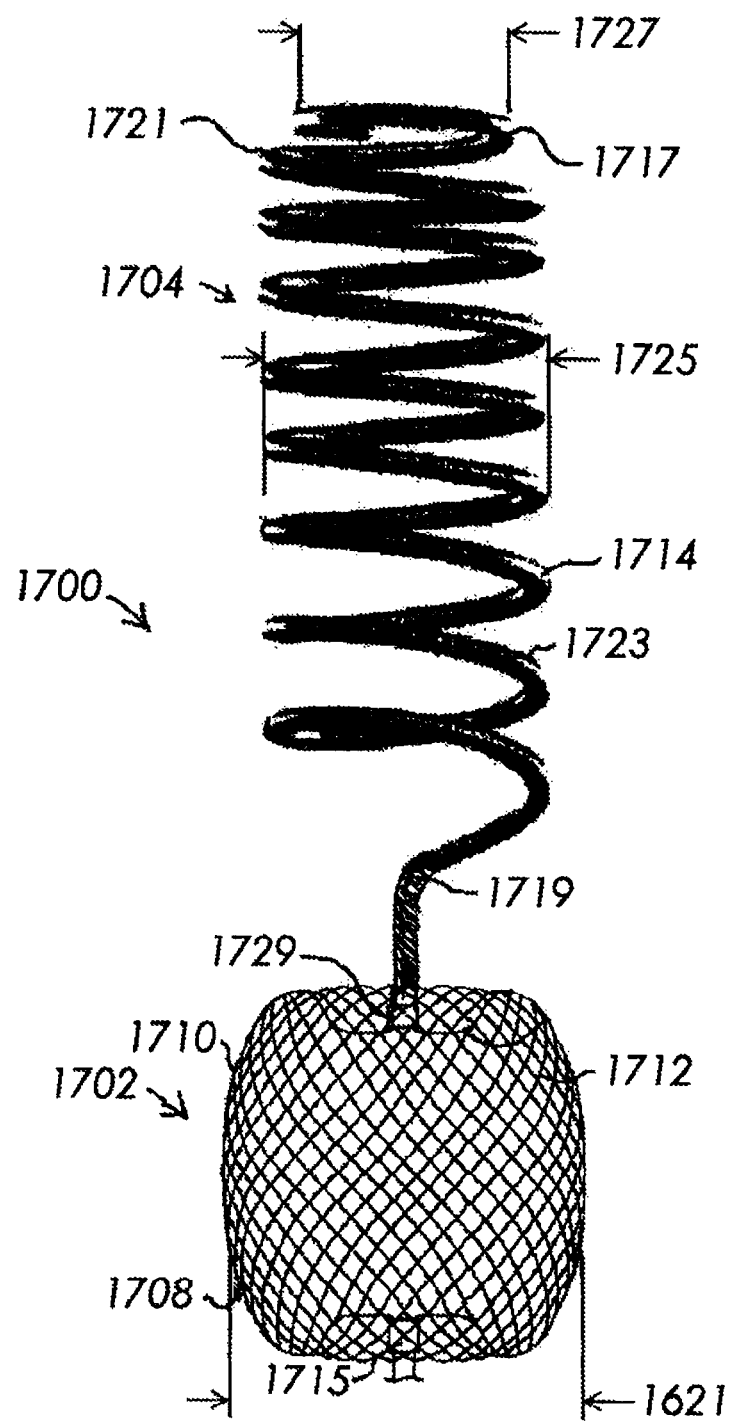
FIG. 33 is an elevation view of an embodiment of a device for treatment of a patient's vasculature.

FIG. 33 illustrates an embodiment of a combination mesh and coil device 1700 for treatment of a vascular defect. The combination mesh and coil device 1700 comprises a mesh portion 1702 and a coil portion 1704. The mesh portion 1702 has a proximal end 1708 and a distal end 1710, and may incorporate any number of the embodiments described herein, but is generally braided from filaments 1712. The filaments 1712 may be secured at the proximal end 1708 with a marker band 1715. The coil portion 1704 comprises a proximal end 1719 and a distal end 1721, and may be constructed from a primary platinum or platinum alloy coil (for example, 92% Platinum, 8% Tungsten), wound into one of more secondary diameters. The coil portion 1704 may be wound from single-filar or multi-filar wire 1723 having a diameter of between 0.0008 inches and 0.005 inches, or between 0.001 inches and 0.0035 inches. The secondary diameter 1725 may approximate the diameter 1621 of the mesh portion 1702, or may be less than the diameter 1621 of the mesh portion 1702, depending on the application. For example, it may be configured to be about one-half of the diameter 1621 of the mesh portion 1702. The distal end 1721 may include one or more first loops 1717 having a reduced secondary diameter 1727. The coil portion 1704 may be secured to the mesh portion 1702 at a band 1729, which may or may not need to be radiopaque, because of the general radiopacity of the platinum material of the coil portion 1704. The combination mesh and coil device 1700 is configured to have a relaxed, expanded state, as shown in FIG. 33, wherein the mesh portion 1702 is a globular or other shape, and the coil portion 1704 has its one or more secondary diameters 1725, 1727. The combination mesh and coil device 1700 also has a radially constrained, elongated state for delivery through a microcatheter, wherein the mesh portion 1702 is collapsed and elongated, and the coil portion 1704, is straightened and elongated.

The potential utility of the coil portion 1704 is multifold. First, the coil portion 1704, being the initial portion of the combination mesh and coil device 1700 that is delivered to the vascular defect, can atraumatically track around the diameter of the vascular defect, and aid the engagement of the combination mesh and coil device 1700 within the vascular defect. The secondary diameter 1725 of one or more loops 1714 may be chosen to approximate the diameter 1621 of the mesh portion 1702, or in some cases be slightly larger, so that the coil portion 1704 may form a three-dimensional frame around the vascular defect, with the mesh portion 1702 being expanded within this three-dimensional frame. The reduced secondary diameter 1727 may be chosen to be 50% to 85% of the secondary diameter 1725, and serves to keep the coil portion 1704 within the vascular defect, and out of, for example, the parent vessel, as the coil portion 1704 is first being inserted within the vascular defect. An additional use of the coil portion 1704 is to serve as a biasing member for pushing the expanded mesh portion 1702 against the opening of the vascular defect (such as the neck of an aneurysm). This can allow a smaller diameter mesh portion 1702 to effectively disrupt flow inside a larger diameter vascular defect, without having to volumetrically fill the entire vascular defect. These uses will be illustrated in more detail in the following figures.

FIGS. 34A-34B illustrate a method for implanting a combination mesh and coil device 1700b through a microcatheter 1761 into an aneurysm 160 having a neck 167 and a dome 161. The combination mesh and coil device 1700b comprises a mesh portion 1702b and a coil portion 1704b.

In FIG. 34A, the coil portion 1704a is delivered out of the microcatheter 1761. The coil portion 1704b has helical shape and has a significant spring constant in the axial direction. The length of the helix (i.e., number of coils) is chosen, so that the coil portion 1704b will be able to be axially compressed between the dome 161 of the aneurysm 160 and the mesh portion 1702b when the mesh portion 1702b is delivered completely out of the microcatheter 1761 and self-expands in a portion adjacent the neck 167 of the aneurysm 160 (FIG. 34B). After the delivery of the entire combination mesh and coil device 1700b into the aneurysm 160, the combination mesh and coil device 1700b is detached from its delivery apparatus 1732b and the microcatheter 1761 is retracted and removed from the patient. The delivery apparatus 1732b may be removed completely from the microcatheter 1761, before the microcatheter 1761 is retracted and removed from the patient, or may be only retracted within the microcatheter 1761. The mesh portion 1702b may incorporate at least some radiopaque filaments, for example made from platinum or platinum alloy. The compressed coil portion 1704b places a force F onto the expanded mesh portion 1702b which holds it against the neck 167 of the aneurysm 160. A force (axial bias) of as high of 0.27 grams or higher has been predicted to be exerted from flow momentum on a basilar tip aneurysm neck during a portion of each cardiac cycle. The spring constant of the coil portion 1704b can be configured so that when at least partially compressed, a force F (axial bias) of greater than 0.27 grams is applied on the mesh portion 1702b and thus against the neck 167 of the aneurysm. The basilar tip aneurysm typically has the highest flow of cerebral aneurysms. Calculating the effect that systolic and diastolic blood pressure have on the expansion and contraction and of a blood vessel and aneurysm at the neck and the area surrounding the neck, some assumptions can be made to further expand the requirements of the force F. Choosing a low diastolic pressure of 40 mm Hg and a neck diameter of 2.5 mm, a force of 2.67 grams is predicted. Choosing a high diastolic pressure of 120 mm Hg and a neck diameter of 3.6 mm, a force of 16.6 grams is predicted. Therefore, the coil portion 1704b may be configured so that when at least partially compressed, a force F of greater than 0.27 grams, or more particularly a force F greater than 2.67 grams, and more particularly a force F greater than 16.6 grams is applied on the mesh portion 1702b and thus against the neck 167 of the aneurysm. Because the mesh portion 1702b does not need to fill the entire volume of the aneurysm 160, the mesh portion 1702b may be significantly smaller, and by being smaller, may fit into smaller microcatheter lumens and be deliverable through more tortuous blood vessels, and thus be usable in more remotely located aneurysms. The combination mesh and coil device 1700b is thus usable in large or giant aneurysms, but still deliverable with standard, small diameter microcatheter lumens.

FIGS. 35A-35B illustrate a method for implanting a combination mesh and coil device 1700c, through a microcatheter 1761 into an aneurysm 160 having a neck 167 and a dome 161. The combination mesh and coil device 1700c comprises a mesh portion 1702c and a coil portion 1704c. In FIG. 35A, the coil portion 1704c is delivered out of the microcatheter 1761. The coil portion 1704c has helical shape and has one or more loops. The purpose of the coil portion 1704c is to protect the aneurysm 160 while the combination mesh and coil device 1700c is delivered from the microcatheter 1761 and positioned into the aneurysm 160 before and after the mesh portion 1702c self-expands within the aneurysm 160 (FIG. 35B). After the delivery of the entire combination mesh and coil device 1700c into the aneurysm 160, the combination mesh and coil device 1700c is detached from its delivery apparatus 1732c and the microcatheter 1761 is retracted and removed from the patient. The mesh portion 1702c may incorporate at least some radiopaque filaments, for example made from platinum or platinum alloy. The combination mesh and coil devices 1700a, 1700b, 1700c may also each share one or more characteristics of each other (i.e., shape, force application, atraumatic coil).

Figure 35C:
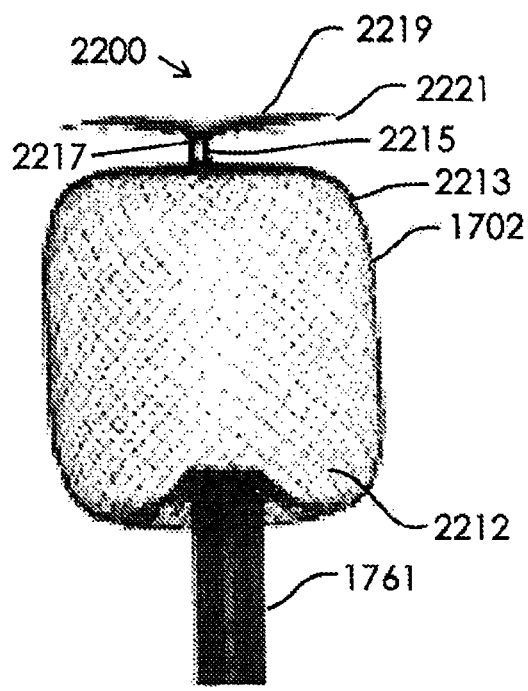
FIG. 35C illustrates an elevation view of an embodiment of a device for treatment of a patient's vasculature.
Figure 35D:
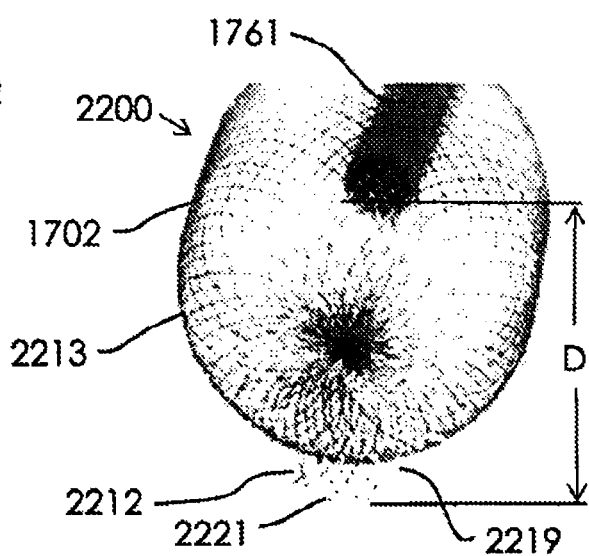
FIG. 35D illustrates a perspective view of a top of the device of FIG. 35C.
Figure 35E:
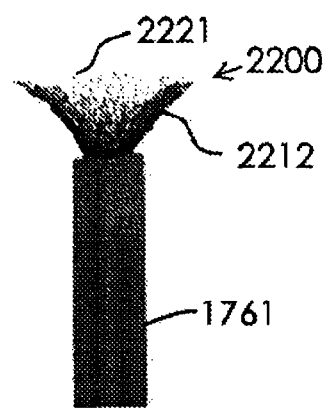
FIGS. 35E-35F illustrate the device of FIG. 35C being delivered from a microcatheter.
Figure 35F:
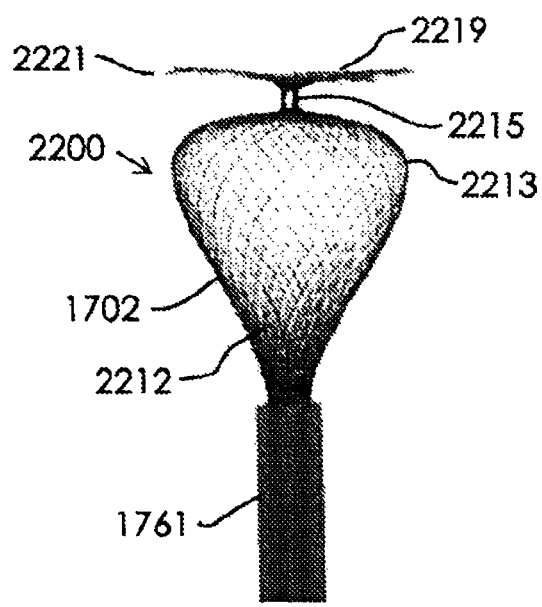

FIGS. 35C-35D illustrate an embodiment of a mesh device 2200 that has been delivered through a microcatheter 1761. The mesh device 2200 includes a mesh portion 1702 comprising filaments 2212 that are secured at a distal end 2213 at a cylindrical hub 2215. The filaments 2212, each having a filament end 2221, extend beyond a distal end 2217 of the cylindrical hub 2215 in a generally radial direction, forming a circular projection 2219 having diameter D. FIGS. 35E-3F illustrate the mesh device 2200 being delivered from the microcatheter 1761 (e.g., into a vascular defect). In some embodiments, the circular projection 2219 is analogous to the coil portion 1704b of the combination mesh and coil device 1700b of FIGS. 34A-34B, and may be configured to apply a biasing force. In some embodiments, the filaments 2212 are braided. In some embodiments, the circular projection 2219 is configured to protect an aneurysm 160, in a manner similar to the coil portion 1704c of the combination mesh and coil device 1700c of FIGS. 35A-35B. The circular projection 2219 may include filaments 2212 that are braided, partially braided, or have the braid undone or unraveled.

Figure 36:
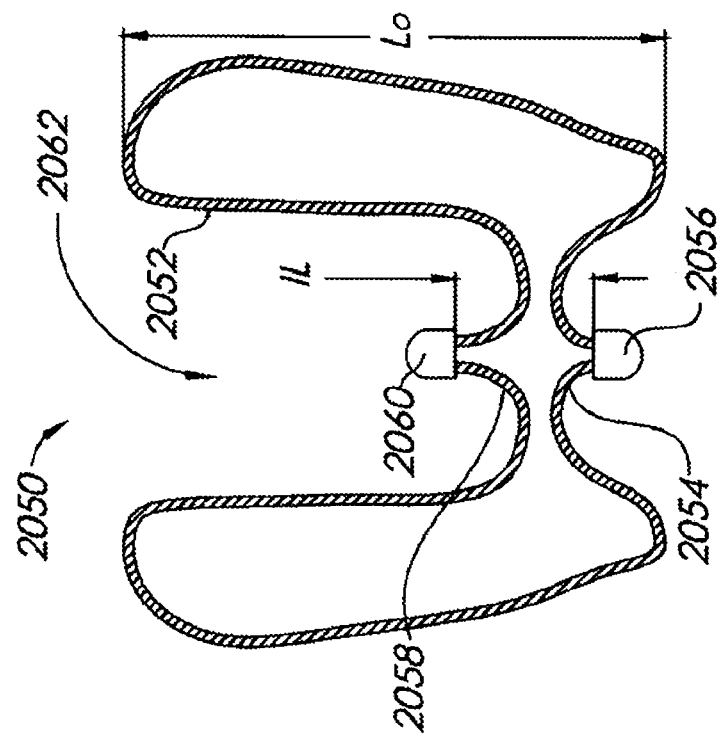
FIG. 36 is a partial cross-sectional view of an embodiment of a mesh device.

FIG. 36 illustrates an embodiment of a mesh device 2050 having a single tubular mesh structure 2052 secured at its proximal end 2054 at a proximal hub 2056, and secured at its distal end 2058 at a distal hub 2060. The inner length IL of the mesh device 2050 is relatively short in comparison to the overall length $L_O$, because of the shape that is heat set into the single tubular mesh structure 2052, the shape comprising a concavity 2062.

Figure 37:
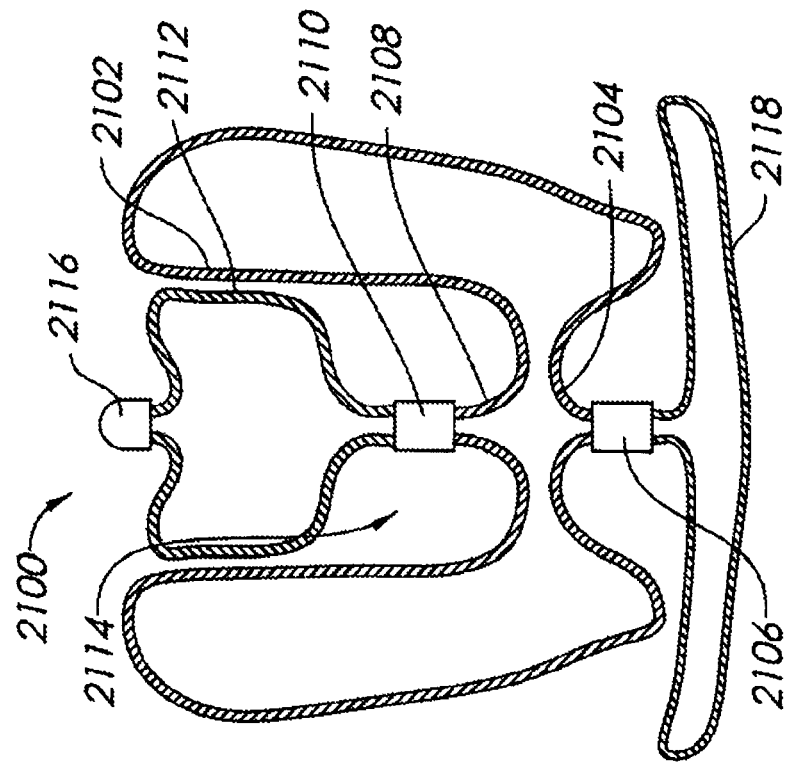
FIG. 37 is a partial cross-sectional view of an embodiment of a multi-lobe mesh device.

FIG. 37 illustrates an embodiment of a multi-lobe mesh device 2100 having a center lobe 2102 secured at its proximal end 2104 at a proximal hub 2106, and secured at its distal end 2108 at a center hub 2110, in a similar manner as the single tubular mesh structure 2052 or the mesh device 2050 of FIG. 36. However, the multi-lobe mesh device 2100 further comprises a distal lobe 2112 that is able to nest within a concavity 2114 within the center lobe 2102. The distal lobe 2112 is secured by the center hub 2110 and a distal hub 2116. Additionally, multi-lobe mesh device 2100 comprises a proximal lobe 2118, secured by the proximal hub 2106. In some embodiments, the entire multi-lobe mesh device 2100 is configured to be implanted within a vascular defect. In some embodiments the center lobe 2102 and the distal lobe 2112 are configured to reside in the vascular defect while the proximal lobe 2118 is configured to reside on the other side of the entry point to the vascular defect. For example, in FIG. 40, the proximal lobe 2118 resides at least partially in the parent artery 414 adjacent the neck 167 of the aneurysm (vascular defect 160). In some embodiments, the center lobe 2102 and the proximal lobe 2118 serve as bookends to hold the multi-lobe mesh device 2100 at the neck 167.

Figure 38:
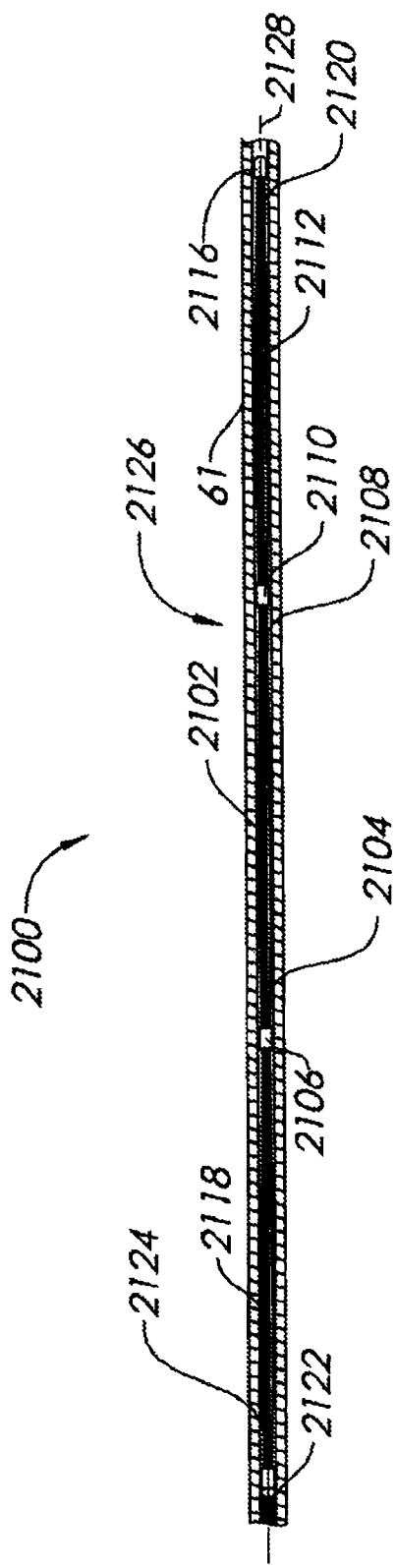
FIG. 38 is an elevation view in partial section of a distal end of a delivery catheter with the device for treatment of a patient's vasculature of FIG. 37 disposed therein in a collapsed constrained state.

Turning to FIG. 38, the multi-lobe mesh device 2100 is shown in a radially constrained state for delivery along a longitudinal axis 2128 through a microcatheter 61. The multi-lobe mesh device 2100 is releasably coupled to a delivery apparatus 2122 at its proximal end 2124. The distal end 2120 of the multi-lobe device 2100 in its radially constrained state corresponds to a distal extremity of the distal lobe 2112. The serial array 2126 of the three lobes 2112, 2102, 2118 assures that upon delivery, there are no layer overlaps that would increase profile. The multi-lobe mesh device 2100 thus has a small radially constrained profile, and may be deliverable through microcatheter 61 having an inner diameter as small as 0.021" and even as small as 0.017".

FIG. 39 illustrates a multi-lumen mesh device 2130 having a proximal lobe 2134 and a distal lobe 2132, the proximal lobe 2134 secured at a proximal hub 2136 and the distal lobe 2132 secured at the proximal hub 2136 and a center hub 2138. As in the embodiment of the multi-lobe mesh device 2100 of FIG. 40, the proximal lobe 2134 may be configured to reside within the vascular defect or to reside within the parent artery, and thus straddling the neck.

Turning to FIGS. 41 and 42, a castellated mandrel assembly 1038 is illustrated and comprises a castellated mandrel 1034 having a radiused cap 1044 within its central cavity 1046. The castellated mandrel 1034 includes a cylindrical battlement-like structure 1048 having a plurality of slots, or crenels 1052, separated by a plurality of posts, or merlons 1054. The embodiment illustrated in FIGS. 41 and 42 comprises 18 crenels 1052 and 18 merlons 1054, however, alternative embodiments may include 27 crenels 1052 and 27 merlons 1054, or other quantities. The radiused cap 1044 has a convex radius 1056 whose surface 1058 is preferably contained within the portion of the central cavity 1046 surrounded by the battlement-like structure 1048. A pin 1064 extends from the radiused cap 1044, and extends into a hole 1066 within the castellated mandrel 1034. The radiused cap 1044 may be secured to the castellated mandrel 1034 by attaching the pin 1064 to the hole 1066 using a threaded screw, adhesive, epoxy, welding, or analogous methods. The radiused cap 1044 and the castellated mandrel 1034 may be made from rigid, durable materials, such as stainless steel.

Figures 43A, 43B:
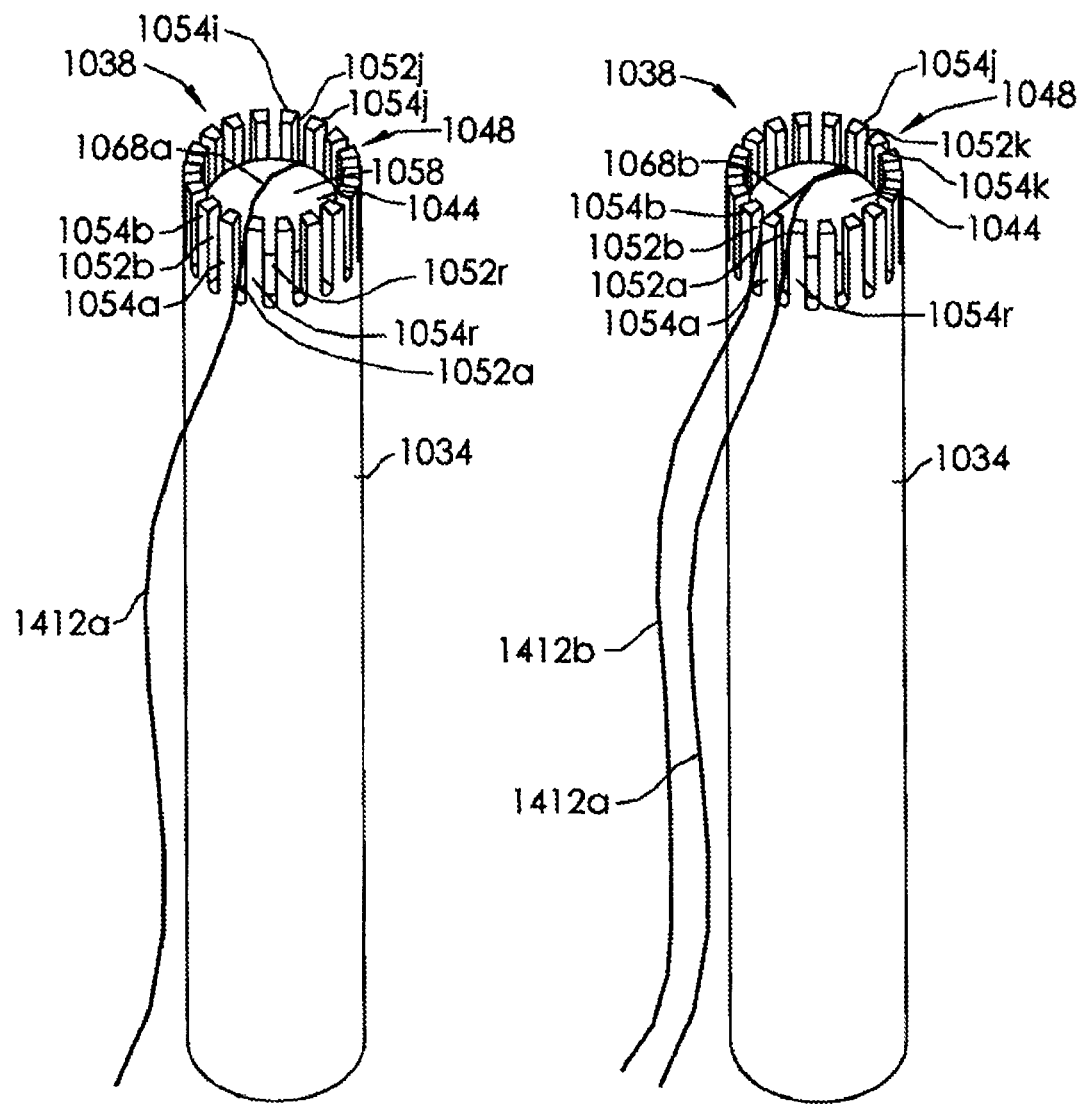
FIGS. 43A-43C illustrate the method of loading the castellated mandrel assembly of FIG. 41 for the braiding process for devices for treatment of a patient's vasculature.
Figure 43C:
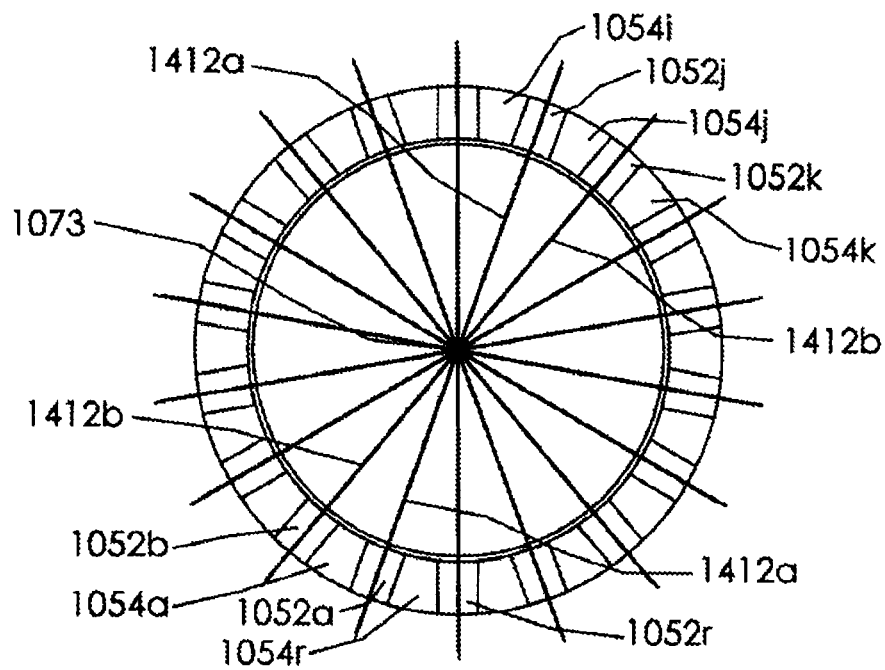

The loading of a castellated mandrel assembly 1038 for the process of constructing an embodiment of a mesh device is illustrated in FIGS. 43A-43C. Merlons 1054a-r are circumferentially arrayed around the battlement-like structure 1048, with crenels 1052a-r between each of the merlons 1054a-r. In FIG. 43A, a first filament 1412a is loaded in a downward direction into crenel 1052a (between merlons 1054r and 1054a) and crenel 1052j (between merlons 1054i and 1054j) and secured to the castellated mandrel assembly 1038. The first filament 1412a may be secured, for example, so that a central portion 1068a of the first filament 1412a is held snugly across the surface 1058 of the convex radius 1056 of the radiused cap 1044. In an 18-crenel embodiment of the castellated mandrel assembly 1038, the locations of crenel 1052a and 1052j are 180° from each other, approximating, for example, 12 o'clock and 6 o'clock locations on a clock face. However, other, non-180° configurations, such as the configuration of FIG. 43D, may be chosen for the filament 1412a, or subsequent filaments 1412 to be loaded. In FIG. 43B, a second filament 1412b is loaded in a downward direction into crenel 1052b (between merlons 1054a and 1054b) and crenel 1052k (between merlons 1054j and 1054k) and secured to the castellated mandrel assembly 1038. A central portion 1068b of the filament 1412b is crossed over the central portion 1068a of the first filament 1412a, and held snugly across the convex radius 1056 of the radiused cap 1044. This loading is continued until all filaments 1412 are loaded and secured to the castellated mandrel assembly 1038. Multiple filaments 1412 may be loaded into each of the crenels 1052, or only certain selected crenels 1052. After loading all of the filaments 1412 into the crenels 1052 and securing the filaments 1412 to the castellated mandrel assembly 1038, the filaments 1412 are ordered and extended radially, and the braiding process is performed as previously described in relation to these figures. The resulting mesh device, such as the mesh device 1800 of FIG. 47, has substantially closed distal apex 1807, because of the manner in which the filaments 1412 are layered over each other at the radiused cap 1044. The mesh device 1800 of FIG. 47 may be made with, for example, 72 to 216 filaments 1412, but because the loading of the mandrel produces the equivalent of two filaments 1412 from a single piece of wire, there are only 36 to 108 pieces of wire required. A mixture of platinum or platinum alloy filaments with Nickel-Titanium filaments may be chosen to add radiopacity to the mesh device 1800, especially at the distal end. Alternatively, drawn filled tubes (DFT) having a radiopaque (e.g., platinum or platinum alloy) core may be used. In the mesh device 1800 of FIG. 47, filament diameters may range from about 0.0005 inches to about 0.002 inches, or from about 0.00075 inches to 0.00125 inches FIG. 43C illustrates a top view of the loaded castellated mandrel assembly 1038 of the mesh device 1800, made in conjunction with the method described in FIGS. 43A-43B. Because each of the filaments 1412 crosses a center crossing point 1073, the substantially closed distal apex 1807 of the mesh device 1800 includes many layers of filaments 1412 at this center crossing point 1073. However, shaping and heat forming of the mesh device 1400 can at least partially reform some or all of the filaments 1412 at the center crossing point 1073, spreading them out in order to lessen the bulk at the center crossing point.

Figure 43D:
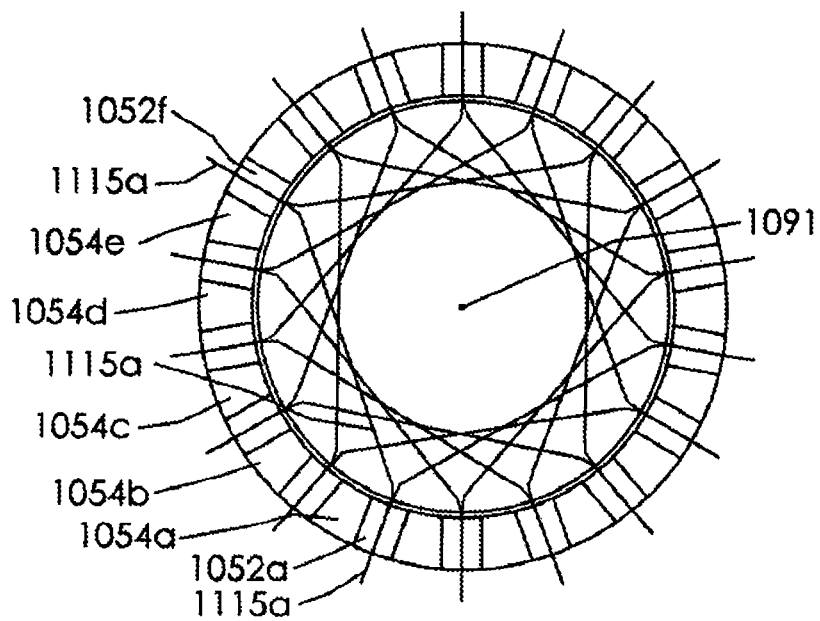
FIG. 43D illustrates an alternative embodiment for loading the castellated mandrel assembly of FIG. 41.

An alternative filament loading method is illustrated in FIG. 43D. Filaments 1115 are loaded in a staggered manner. Filament 1115a is loaded into crenels 1052a and 1052f; thus, it extends inside merlons 1054a, 1054b, 1054c, 1054d, and 1054e, and is held snugly across a portion of the convex radius 1056 of the radiused cap 1044. Filament 1115b is loaded into crenels 1052b and 1052g, and thus it extends inside merlons 1054b, 1054c, 1054d, 1054e, and 1054f; and crosses on top of filament 1115a. This is continued until all of the filaments 1115 are loaded, and the configuration of FIG. 43D is visible. In this embodiment, a central opening 1091 is formed, in contrast to the closed distal apex 1807 of the mesh device 1800. The size of the central opening 1091 can be varied, depending on both the diameter of the castellated mandrel 1034 at the battlement-like structure 1048, and the total number of crenels 1052 skipped when loading each filament 1115.

Figure 44A:
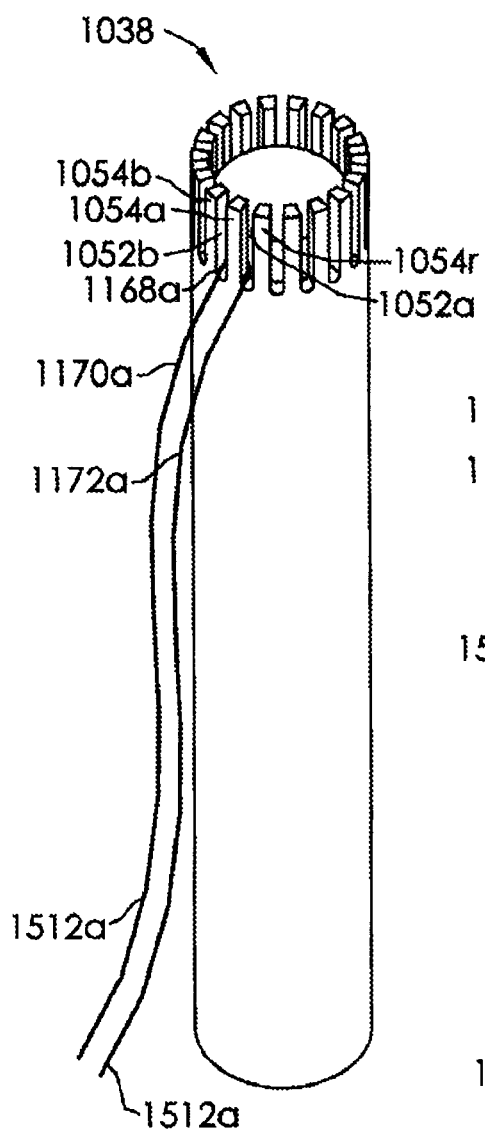
FIGS. 44A-44B illustrate the method of loading the castellated mandrel assembly of FIG. 41 for the braiding process for devices for treatment of a patient's vasculature.
Figure 44B:
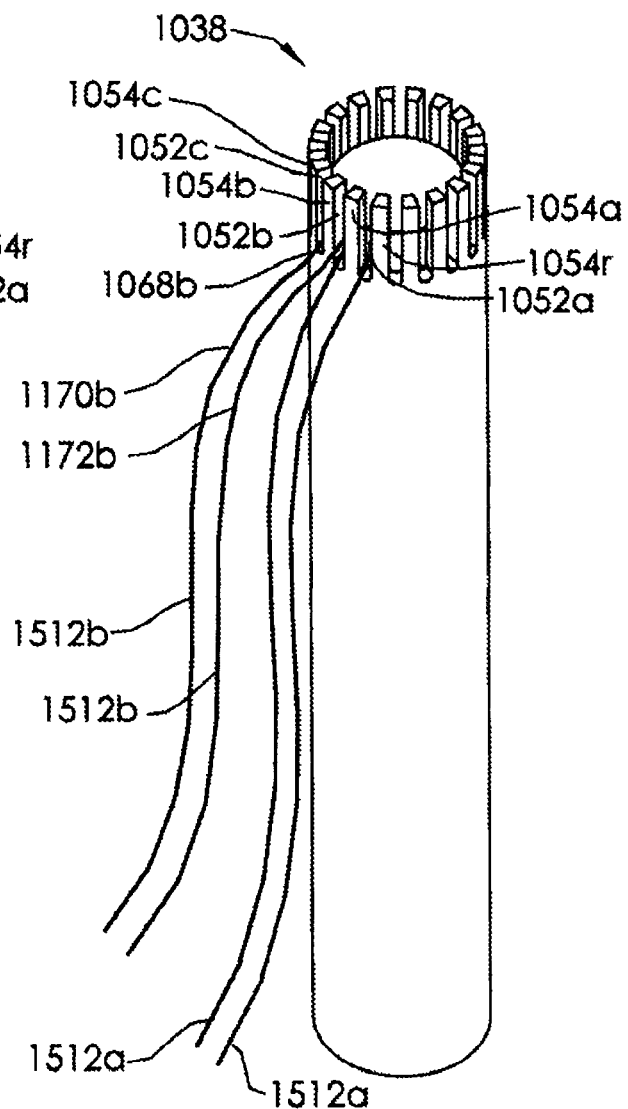

The forming of a mesh device having an open distal end is illustrated in FIGS. 44A-44B. FIG. 44A, a first filament 1512a is loaded in a downward direction into crenel 1052a (between merlons 1054r and 1054a) and crenel 1052b (between merlons 1054a and 1054b). A central portion 1168a of the first filament 1512a is held snugly around the merlon 1054a and a first portion 1170a and a second portion 1172a of the filament 1512a are secured to the castellated mandrel assembly 1038. In FIG. 44B, a second filament 1512b is loaded in a downward direction into crenel 1052b (between merlons 1054a and 1054b) and crenel 1052c (between merlons 1054b and 1054c). A central portion 1168b of the second filament 1512b is held snugly around the merlon 1054b and a first portion 1170b and a second portion 1172b are secured to the castellated mandrel assembly 1038. This loading is continued until all the filaments 1512 are loaded and secured to the castellated mandrel assembly 1038. Multiple filaments 1512 may be loaded around each of the merlons 1054, or only certain selected merlons 1054. After loading all of the filaments 1512 into the crenels 1052 and securing the filaments 1512 to the castellated mandrel assembly 1038, the filaments 1512 are ordered and extended radially, and the braiding process is performed as previously described in relation to these figures. A plurality of loops results from the central portions 1168 of the filaments 1512 that are initially curved around the merlons 1054 of the castellated mandrel assembly 1038. The diameter of the castellated mandrel 1034 at the battlement-like structure 1048 may be varied, in order to control the diameter of the open portion 1518. The number and size of the merlons 1054 may be varied in order to control the number and size of the loops 1516. The loops 1516 may serve as a blunt leading portion as the mesh device 1500 is expanded within a vascular defect, increasing the safety of its use.

Figure 45:
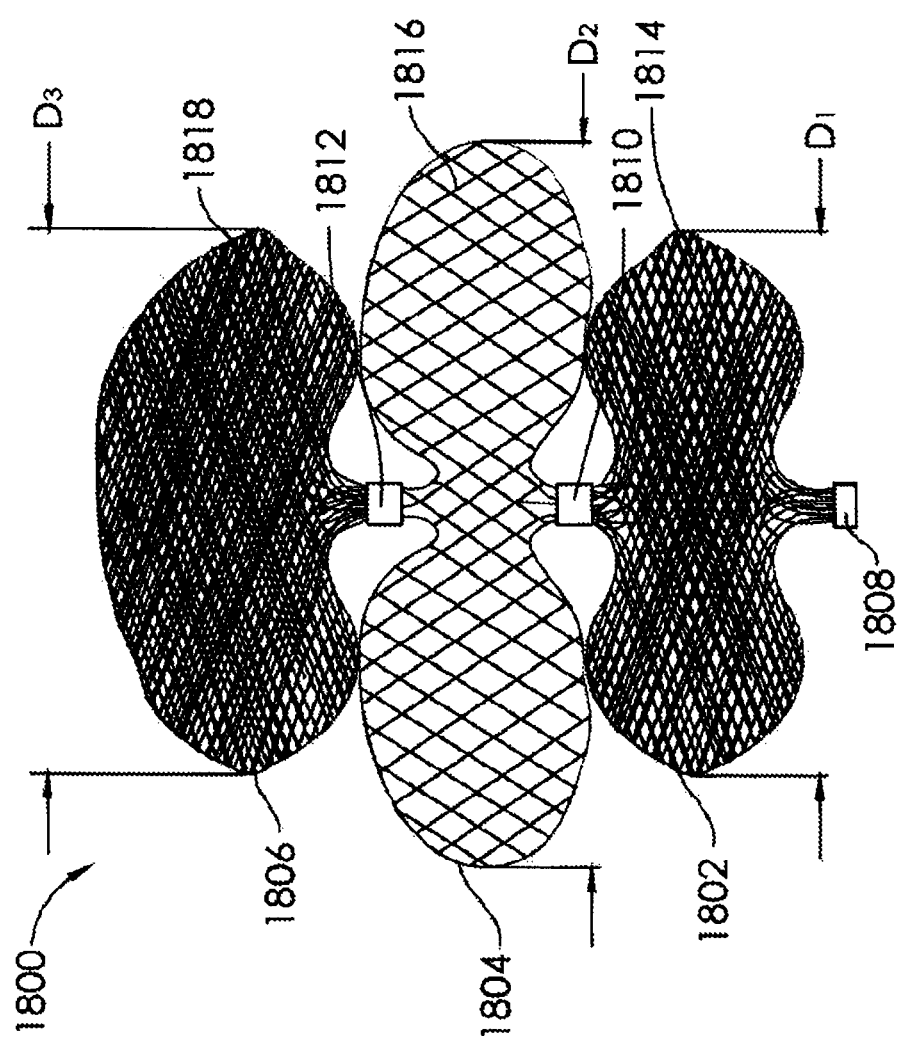
FIG. 45 is an elevation view of an embodiment of a device for treatment of a patient's vasculature.

FIG. 45 illustrates an embodiment of a multi-lobe mesh device 1800 for treatment of a patient's vasculature. In this particular embodiment, the multi-lobe mesh device 1800 comprises a proximal lobe 1802, a center lobe 1804, and a distal lobe 1806. In some embodiments, each of the lobes 1802, 1804, 1806 is formed from a single layer braided tubular member. The lobes may be individually braided, and connected together in parallel via a proximal hub 1808, a central hub 1810, and a distal hub 1812. In some embodiments, the proximal lobe 1802 may be configured to have a first porosity $P_1$, which is relatively small and configured to be placed at an entry portion or neck portion of a vascular defect, and to promote occlusion of the vascular defect. In some embodiments, the center lobe 1804 may be configured to have a radial stiffness, and overall mechanical characteristics that are configured to support the multi-lobe mesh device 1800 within the vascular defect. In some embodiments, the center lobe 1804 may have a second porosity $P_2$, which is greater than the first porosity $P_1$. In some embodiments, the distal lobe 1806 may be configured to have a third porosity $P_3$, which is relatively small and configured to be placed at a distal portion or a dome portion of a vascular defect. In some embodiments, the distal lobe 1806 having the third porosity $P_3$ may be configured to be placed adjacent a prior rupture site, and may be configured to provide a protective fine mesh to limit or eliminate re-rupture. In some embodiments, the first porosity $P_1$ of the proximal lobe 1802 may be approximately equal to the third porosity $P_3$ of the distal lobe 1806. In some embodiments, the distal lobe 1806

In some embodiments the proximal lobe 1802 may be constructed from between about 108 and about 180 filaments 1814. In some embodiments, the proximal lobe 1802 may be constructed from between about 54 and about 90 nitinol filaments and between about 54 and about 90 drawn filled tube (DFT) filaments. In some embodiments, the DFT filaments may comprise an outer, high-strength material such as nitinol, and an inner core of a highly radiopaque material, such as platinum, platinum alloy such as 90% platinum/10% iridium, or gold or tantalum. In some embodiments, the DFT filaments may comprises a cross-sectional fill area ratio of between about 10% and about 50% of the highly radiopaque material. In some embodiments, the DFT filaments may comprises a cross-sectional fill area ratio of between about 20% and about 40% of the highly radiopaque material. In some embodiments, the DFT filaments may comprises a cross-sectional fill area ratio of between about 25% and about 35% of the highly radiopaque material. In some embodiments, the proximal lobe 1802 may comprises nitinol filaments having a transverse dimension or diameter of between about 0.0004" and about 0.0006", and DFT filaments having a transverse dimension of between about 0.0006" and about 0.0009". In some embodiments, the proximal lobe 1802 may comprise about 72 nitinol filaments having a transverse dimension of about 0.0005" and about 72 DFT filaments having a transverse dimension of about 0.00075".

In some embodiments the center lobe 1804 may be constructed from between about 36 and about 54 filaments 1816. In some embodiments, the center lobe 1804 may be constructed from DFT filaments. In some embodiments, the center lobe 1804 may be constructed from nitinol filaments. In some embodiments, the center lobe 1804 may be constructed from a mixture of nitinol and DFT filaments. In some embodiments, the center lobe 1804 may comprise filaments having a transverse dimension of between about 0.0009" and about 0.0014". In some embodiments, the center lobe 1804 may comprise filaments having a transverse dimension of between about 0.001" and about 0.00125".

In some embodiments the distal lobe 1806 may be constructed from between about 108 and about 180 filaments 1818. In some embodiments, the distal lobe 1806 may be constructed from between about 54 and about 90 nitinol filaments and between about 54 and about 90 DFT filaments. In some embodiments, the DFT filaments may comprise an outer, high-strength material such as nitinol, and an inner core of a highly radiopaque material, such as platinum, platinum alloy such as 90% platinum/10% iridium, or gold or tantalum. In some embodiments, the DFT filaments may comprises a cross-sectional fill area ratio of between about 10% and about 50% of the highly radiopaque material. In some embodiments, the DFT filaments may comprises a cross-sectional fill area ratio of between about 20% and about 40% of the highly radiopaque material. In some embodiments, the DFT filaments may comprises a cross-sectional fill area ratio of between about 25% and about 35% of the highly radiopaque material. In some embodiments, the distal lobe 1806 may comprises nitinol filaments having a transverse dimension or diameter of between about 0.0004" and about 0.0006", and DFT filaments having a transverse dimension of between about 0.0006" and about 0.0009". In some embodiments, the distal lobe 1806 may comprise about 72 nitinol filaments having a transverse dimension of about 0.0005" and about 72 DFT filaments having a transverse dimension of about 0.00075". In some embodiments, the distal lobe 1806 may have an additional distal hub (and thus not be made with the castellated mandrel). In these embodiments, the additional distal hub may be radiolucent, and thus allow visualization on x-ray or fluoroscopy. In these embodiments, the filaments may be mostly or all nitinol.

Figure 46:
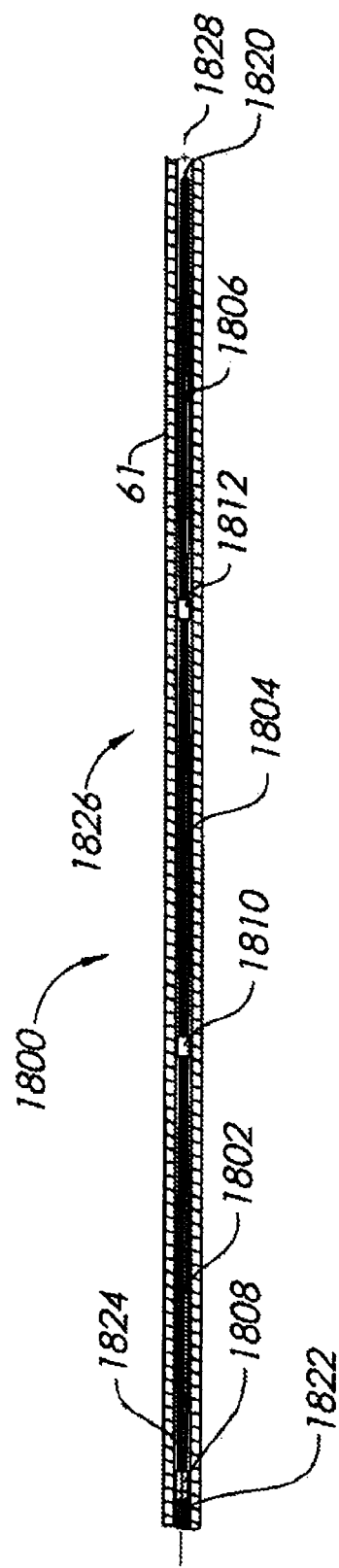
FIG. 46 is an elevation view in partial section of a distal end of a delivery catheter with the device for treatment of a patient's vasculature of FIG. 45 disposed therein in a collapsed constrained state.

In some embodiments, the multi-lobe mesh device 1800 may be constructed so that the proximal lobe 1802 has an expanded state having a first diameter $D_1$, the center lobe 1804 has an expanded state having a second diameter $D_2$, and the distal lobe 1806 has an expanded state having a third diameter $D_3$. In some embodiments, the three diameters $D_1$, $D_2$, $D_3$ may be approximately equal to each other. In some embodiments, first diameter $D_1$ and the second diameter $D_3$ may be less than the second diameter $D_2$ in order to allow the multi-lobe mesh device 1800 to conform to the shape of a vascular defect 160, such as an aneurysm. Turning to FIG. 46, the multi-lobe mesh device 1800 is shown in a radially constrained state for delivery along a longitudinal axis 1828 through a microcatheter 61. The multi-lobe mesh device 1800 is releasably coupled to a delivery apparatus 1822 at its proximal end 1824. The distal end 1820 of the multi-lobe device 1800 in its radially constrained state corresponds to a distal extremity of the distal lobe 1806. The serial array 1826 of the three lobes 1802, 1804, 1806 assures that upon delivery, there are no layer overlaps that would increase profile. The multi-lobe mesh device 1800 thus has a small radially constrained profile, and may be deliverable through microcatheter 61 having an inner diameter as small as 0.021" and even as small as 0.017".

Figure 47:
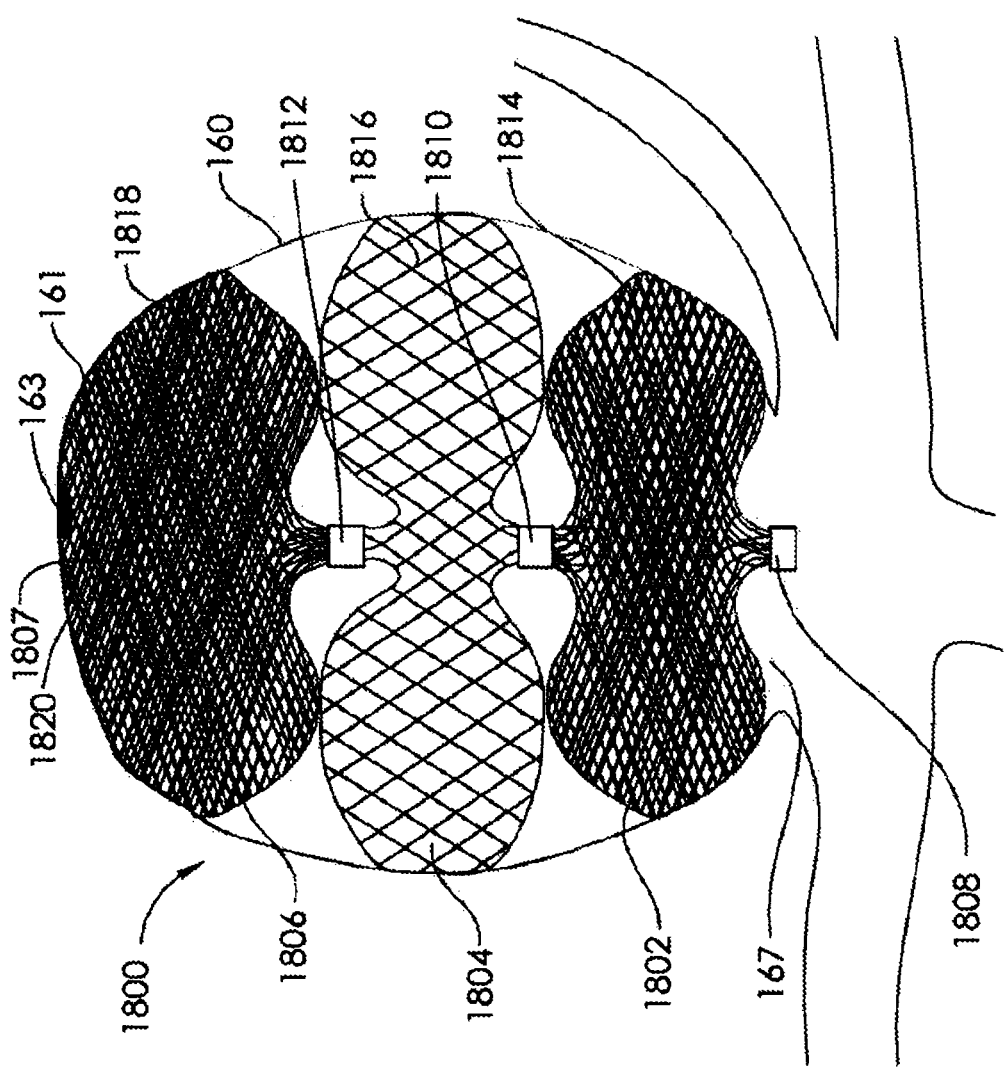
FIG. 47 is the embodiment of a device for treatment of a patient's vasculature of FIG. 45 deployed within an aneurysm.
Figures 49, 50, 51:
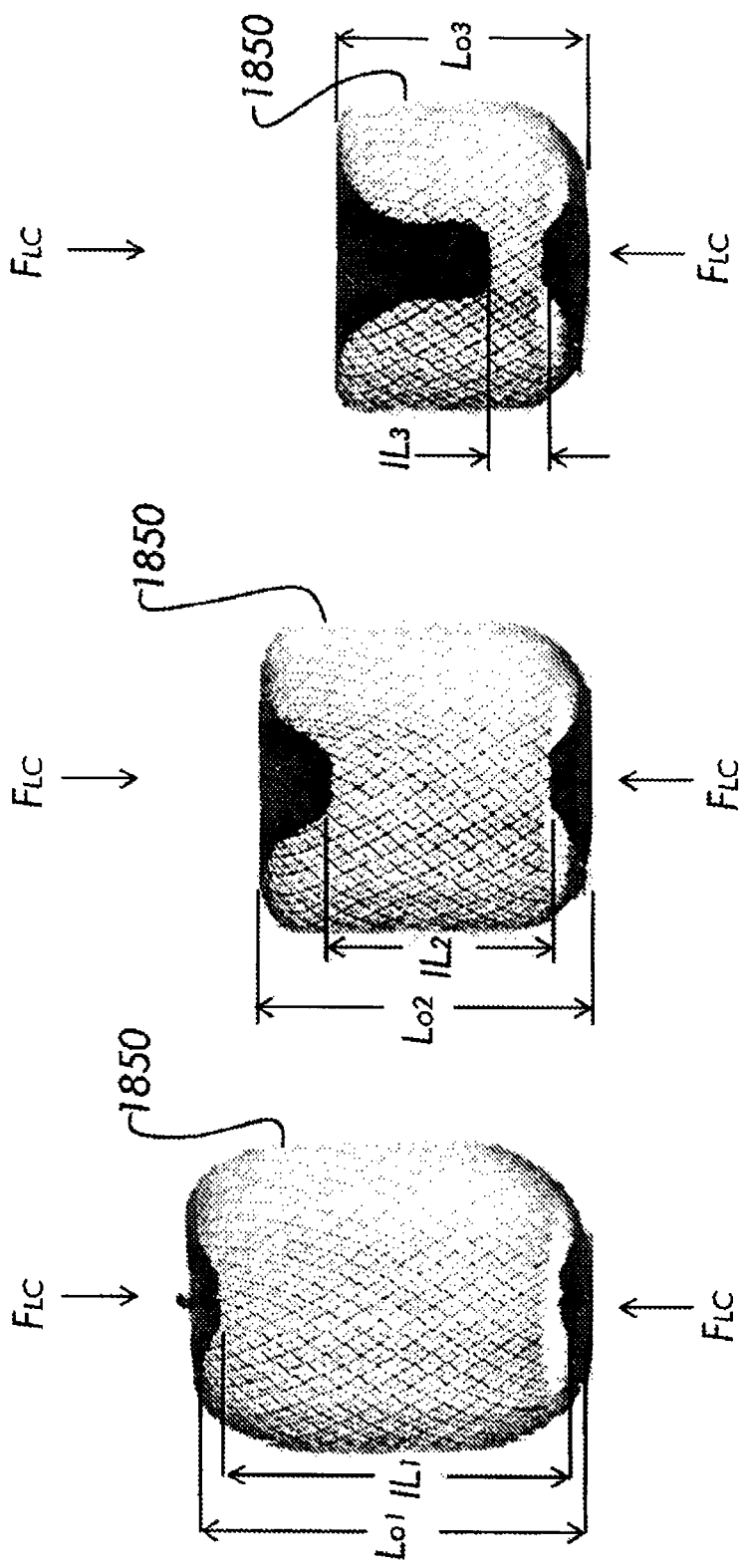
FIG. 49 is an elevation view of an embodiment of a mesh device prior to being longitudinally compressed.
FIG. 50 is an elevation view of the mesh device of FIG. 49 after a certain amount of longitudinal compression.
FIG. 51 is an elevation view of the mesh device of FIG. 49 after an additional amount of longitudinal compression.

FIG. 47 illustrates an embodiment of the multi-lobe mesh device 1800 after being delivered into a vascular defect 160. The distal lobe 1806 has been delivered so that it is located adjacent to a rupture site 163. An appropriate size of the multi-lobe mesh device 1800 has been chosen so that the center lobe 1804 is expanded within the vascular defect 160, giving it mechanical support. The proximal lobe 1802 has been delivered so that it is expanded across the neck 167. The relatively short longitudinal distance between the proximal hub 1808 and the center hub 1810, the relatively short longitudinal distance between the center hub 1810 and the distal hub 1812, and even the relatively short longitudinal distance between the distal hub 1812 and the distal end 1820, all serve to decrease the potential for the multi-lobe mesh device 1800 to undergo longitudinal compression leading to in vivo compaction. This longitudinal compression/compaction is sometimes referred to as clot contraction, and has been described by some as somewhat analogous to the shrinkage that occurs in a wound upon healing. Longitudinal compression of a mesh device 1850 is demonstrated in FIGS. 49-51. After implantation, compressive forces $F_{LC}$ from a number of different biological sources may decrease the overall length $L_O$ of the mesh device 1850 over time (from FIG. 49 to FIG. 51, $L_{O1}$, $L_{O2}$, $L_{O3}$), by forcing the distal internal end 1852 and/or the proximal internal end 1854 to approach each other while some inversion of the mesh device 1850 occurs, thus decreasing the inner length (seen in FIGS. 49-51 as $IL_1$, $IL_2$, $IL_3$). In some embodiments of the mesh device 1850, this may occur at longitudinal compressive forces $F_{LC}$ as low as 0.2 Newton, and even 0.1 Newton. Because the normal expanded configuration of the multi-lobe mesh device 1800 of FIGS. 45-47 has lobes 1802, 1804, 1806 that approximate partial longitudinal compression, additional longitudinal compression is less likely to occur. In some embodiments, the distal lobe 1806 may have an additional distal hub (and thus not be made with the castellated mandrel). In these embodiments, the additional distal hub may be radiolucent, and thus allow visualization on x-ray or fluoroscopy. In these embodiments, the filaments may be mostly or all nitinol.

Figure 48:
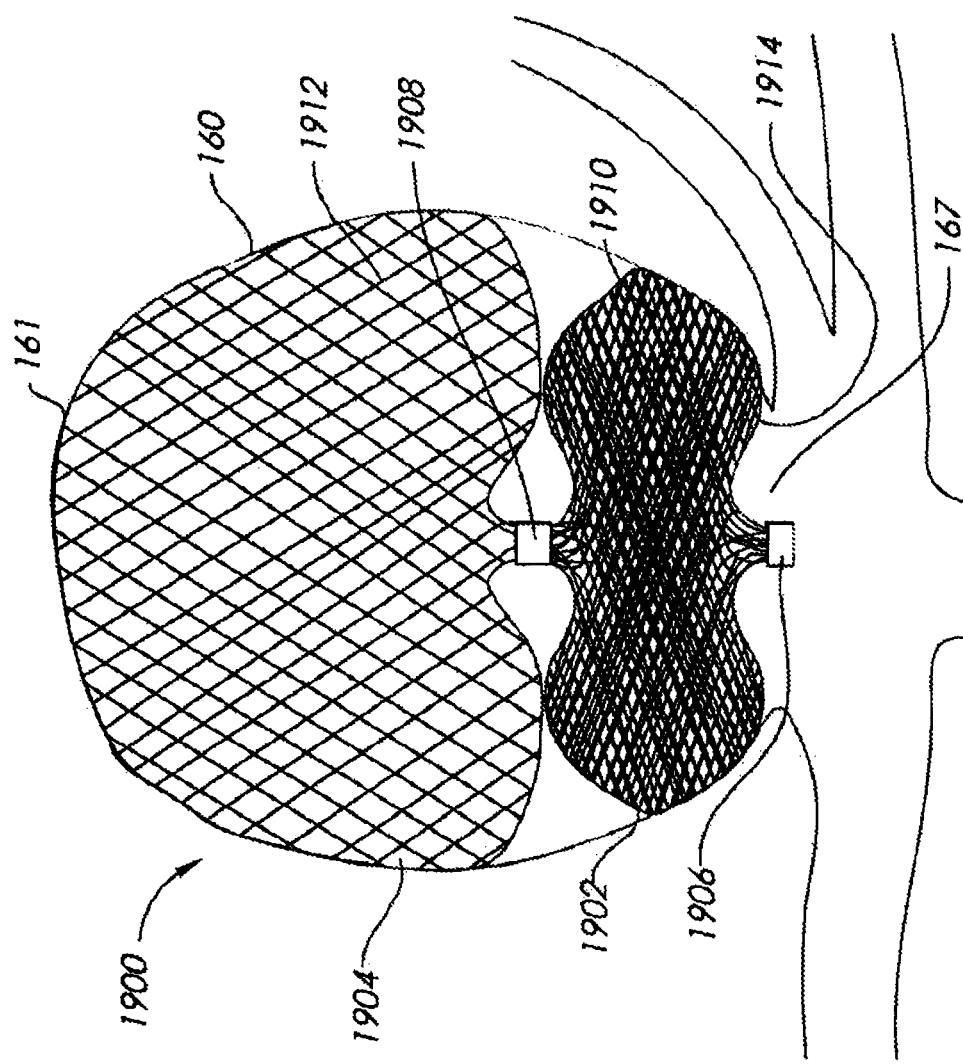
FIG. 48 is an embodiment of a device for treatment of a patient's vasculature deployed within an aneurysm.

FIG. 48 illustrates an embodiment of a multi-lobe mesh device 1900 having a proximal lobe 1902 and a support lobe 1904. The filaments 1910 of the proximal lobe 1902 and the filaments 1912 of the support lobe 1904 are secured to each other by a distal hub 1908. In some embodiments, a proximal hub 1906 secures the filaments 1910 of the proximal lobe 1902 at its proximal end 1914. In some embodiments, the proximal lobe 1902 may be constructed in a similar fashion and with similar materials as the proximal lobe 1802 of the multi-lobe mesh device 1800 of FIGS. 45-47. In some embodiments, the support lobe 1904 may be constructed in a similar fashion and with similar materials as the center lobe 1804 of the multi-lobe mesh device 1800 of FIGS. 45-47. In some embodiments, as shown in FIG. 48, the support lobe 1904 of the multi-lobe mesh device 1900 may be constructed without a hub at its distal end, as may the distal lobe 1806 of the multi-lobe mesh device 1800. In both cases, this may be done to protect the dome 161 of an aneurysm (vascular defect 160). The support lobe 1904 is configured to provide both radial support and longitudinal support within the vascular defect 160. In some embodiments, the support lobe 1904 may have an additional distal hub (and thus not be made with the castellated mandrel). In these embodiments, the additional distal hub may be radiolucent, and thus allow visualization on x-ray or fluoroscopy. In these embodiments, the filaments may be mostly or all nitinol. As described, in the multi-lobe mesh device 1800 of FIG. 47, the proximal lobe 1802 may be made with a relatively smaller porosity than the center lobe 1804, for the purpose of minimizing blood flow at the neck 167 of the aneurysm 160. The distal lobe 1806 may also have a lower porosity than the center lobe 1804 in order to inhibit rebleeding and/or accelerate healing at the rupture site 167. In some embodiments, the center lobe 1804 is constructed from larger diameter filaments than either the proximal lobe 1802 or the distal lobe 1806. This construction may allow the center lobe 1804 to provide increased radial stiffness at the center portion of the aneurysm 160, for example, to maintain the position of the multi-lobe mesh device 1800 within the aneurysm. Any of the three lobes 1802, 1804, 1806 may be constructed of filaments 1814, 1816, 1818 having more than one material and/or more than one diameter or transverse dimension. In the multi-lobe mesh device 1900 of FIG. 48, the proximal lobe 1902 may be made with a relatively smaller porosity than the support lobe 1904, for the purpose of minimizing blood flow at the neck 167 of the aneurysm 160. In some embodiments, the support lobe 1904 is constructed from larger diameter filaments than the proximal lobe 1902. This construction may allow the support lobe 1904 to provide increased radial stiffness at the center portion of the aneurysm 160, for example, to maintain the position of the multi-lobe mesh device 1900 within the aneurysm. Either of the two lobes 1902, 1904 may be constructed of filaments 1910, 1912 having more than one material and/or more than one diameter or transverse dimension.

Figure 52:
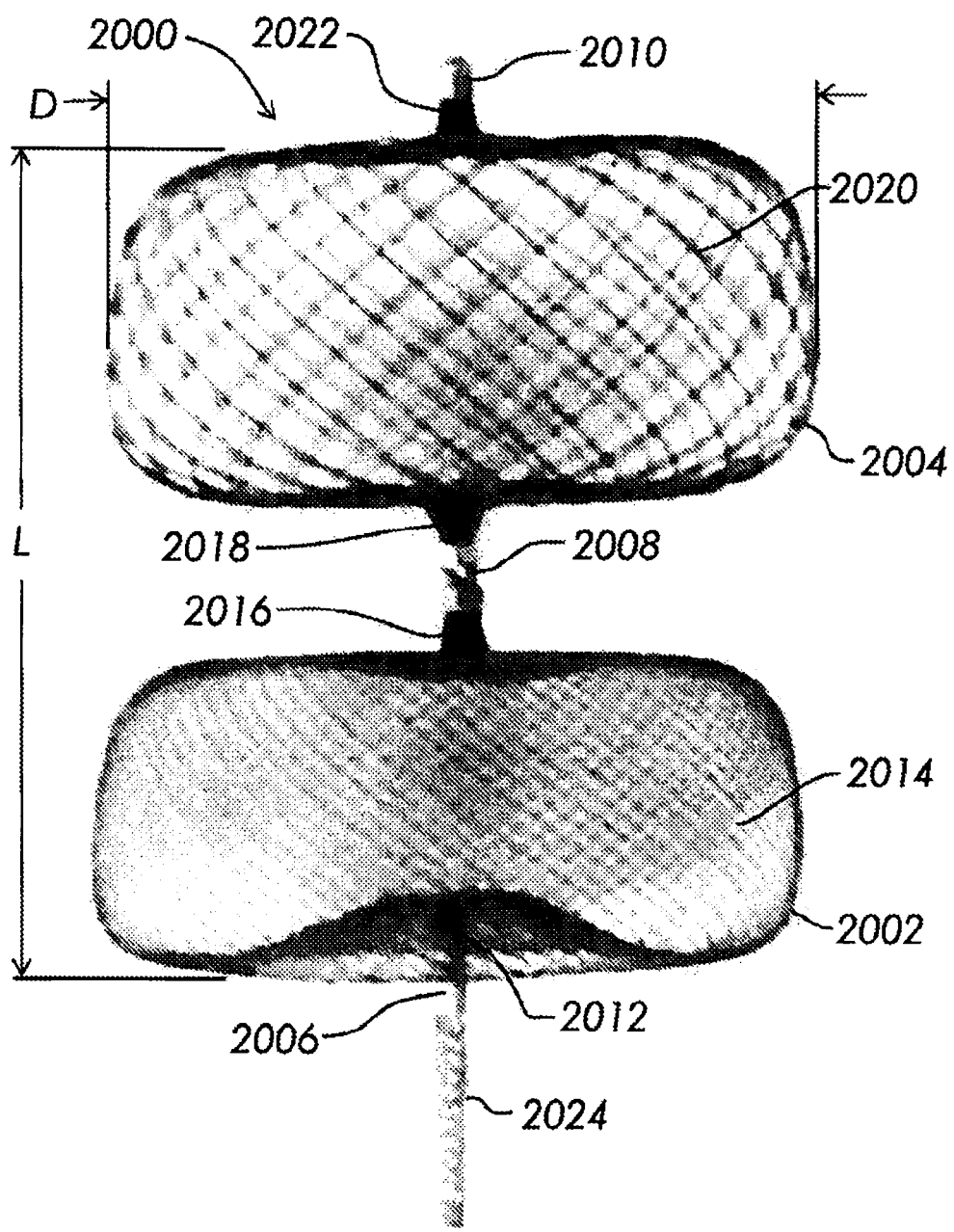
FIG. 52 illustrates an embodiment of a system including a multi-lobe mesh device.

FIG. 52 illustrates an embodiment of a multi-lobe mesh device 2000 having a proximal lobe 2002 and a support lobe 2004 that was constructed in accordance with an embodiment of the present invention. The multi-lobe mesh device 2000 has a proximal hub 2006 which secures the proximal ends 2012 of filaments 2014 of the proximal lobe 2002, a center hub 2008 which secures both the distal ends 2016 of the filaments 2014 of the proximal lobe 2002 and the proximal ends 2018 of the filaments 2020 of the support lobe 2004, and a distal hub 2010 which secures the distal ends 2022 of the filaments 2020 of the support lobe 2004. The multi-lobe mesh device 2000 is releasably secured to a delivery apparatus 2024. The multi-lobe mesh device 2000 was constructed with a relaxed, expanded diameter D of 7 mm. The proximal lobe 2002 was constructed using a combination of 72 nitinol filaments having a diameter of 0.0005" and 72 DFT filaments (nitinol outer shell with a platinum core) having a diameter of 0.00075". The support lobe 2004 was constructed using 54 DFT filaments (nitinol outer shell with a platinum core) having a diameter of 0.00125". After assembly, the multi-lobe mesh device 2000 was successfully passed through a 0.017" diameter inner lumen of a microcatheter 61 (VIA-17 produced by Sequent Medical, Inc., Aliso Viejo, CA). In comparison, standard single-lobe mesh devices having a length equivalent to the total length L of the two lobes 2002, 2004 of the multi-lobe mesh device are currently not able to pass through a 0.017" diameter inner lumen, and require a 0.021" diameter inner lumen. Actually, the collapsed profile of the support lobe 2004 is approximately 0.013" and the collapsed profile of the proximal lobe 2002 is approximately 0.011". In some embodiments, the diameter of the hubs 2006, 2008, 2010 is approximately 0.016". In the multi-lobe mesh device 2000 of FIG. 52, the proximal lobe 2002 may be made with a relatively smaller porosity than the support lobe 2004. In some embodiments, the support lobe 2004 is constructed from larger diameter filaments than the proximal lobe 2002. This construction may allow the support lobe 1904 to provide increased radial stiffness at the center portion of an aneurysm 160, for example, to maintain the position of the multi-lobe mesh device 2000 within the aneurysm. Either of the two lobes 2002, 2004 may be constructed of filaments 2014, 2020 having more than one material and/or more than one diameter or transverse dimension.

Figure 53:
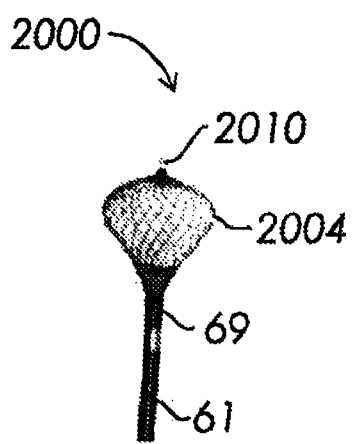
FIGS. 53-56 illustrate the system of FIG. 52 being delivered from a microcatheter.
Figure 54:
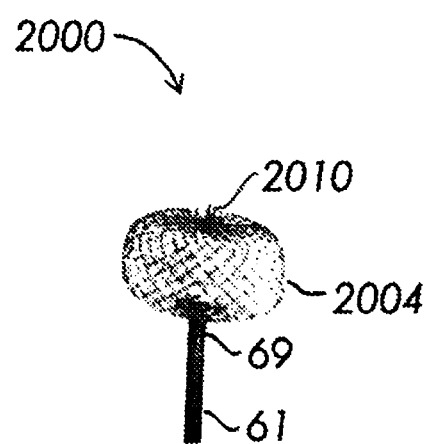
Figure 55:
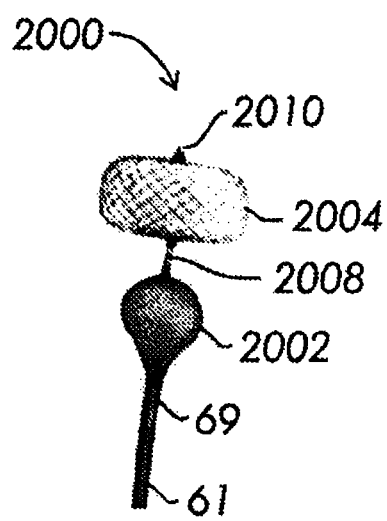
Figure 56:
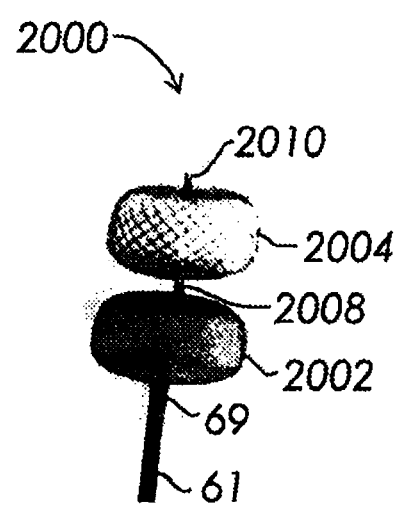

FIGS. 53-56 illustrate the in vitro delivery (simulated use) of the multi-lobe mesh device 2000 through the microcatheter 61 (VIA-17). The distal tip 69 is indicated in each of the four figures. In FIG. 53, the support lobe 2004 begins to expand as it is pushed out of the distal tip 69 of the microcatheter 61. In FIG. 54 the support lobe 2004 reaches its relaxed expanded diameter. In a vascular defect 160, the support lobe 2004 may not reach its fully relaxed expanded diameter, because the vascular defect itself may apply some compression on the support lobe 2004. In FIG. 55, the proximal lobe 2002 begins to expand as it is pushed out of the distal tip 69 of the microcatheter 61. In FIG. 56, the proximal lobe reaches its relaxed expanded diameter. In a vascular defect 160, the proximal lobe 2002 may not reach its fully relaxed expanded diameter, because the vascular defect itself may apply some compression on the proximal lobe 2002.

Figure 57A:
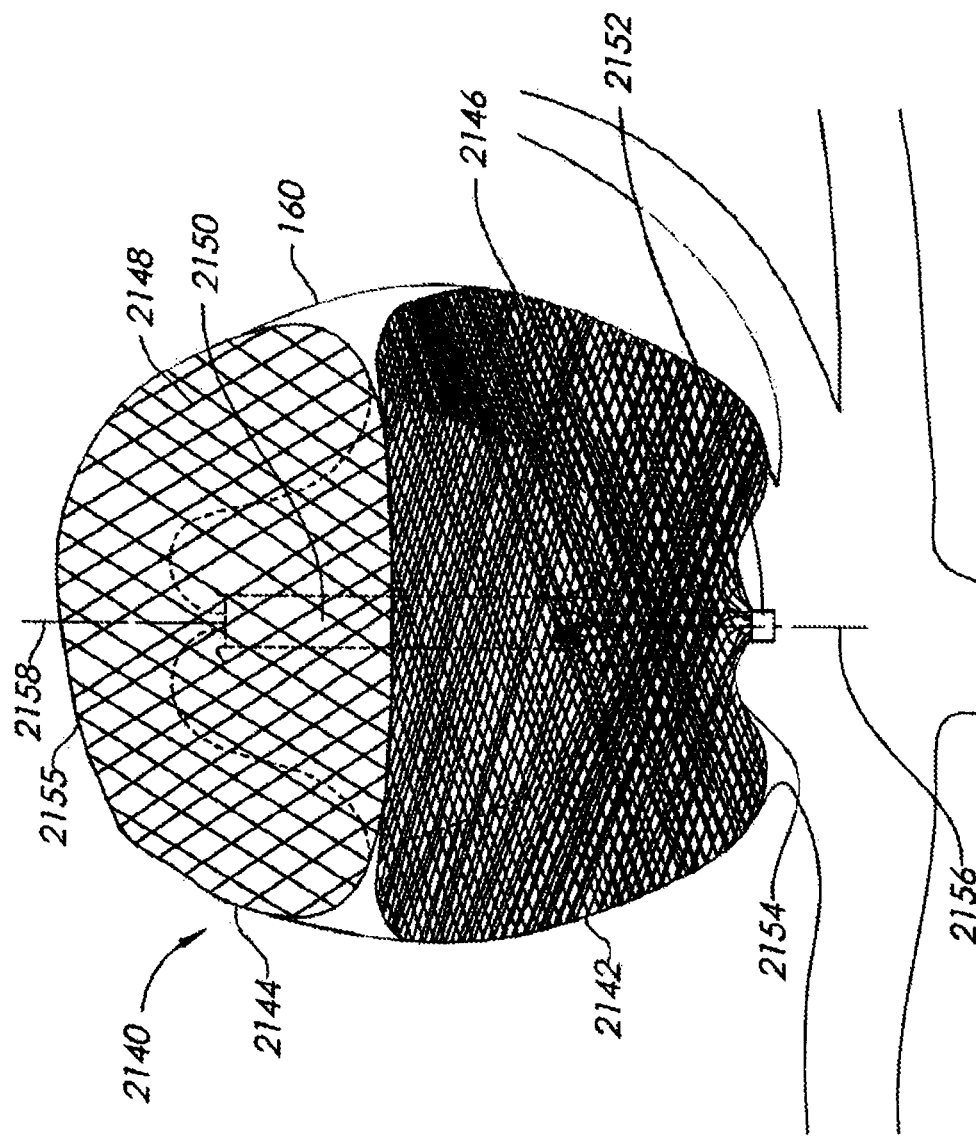
FIG. 57A is an embodiment of a multi-lobe mesh device for treatment of a patient's vasculature deployed within an aneurysm.
Figure 57B:
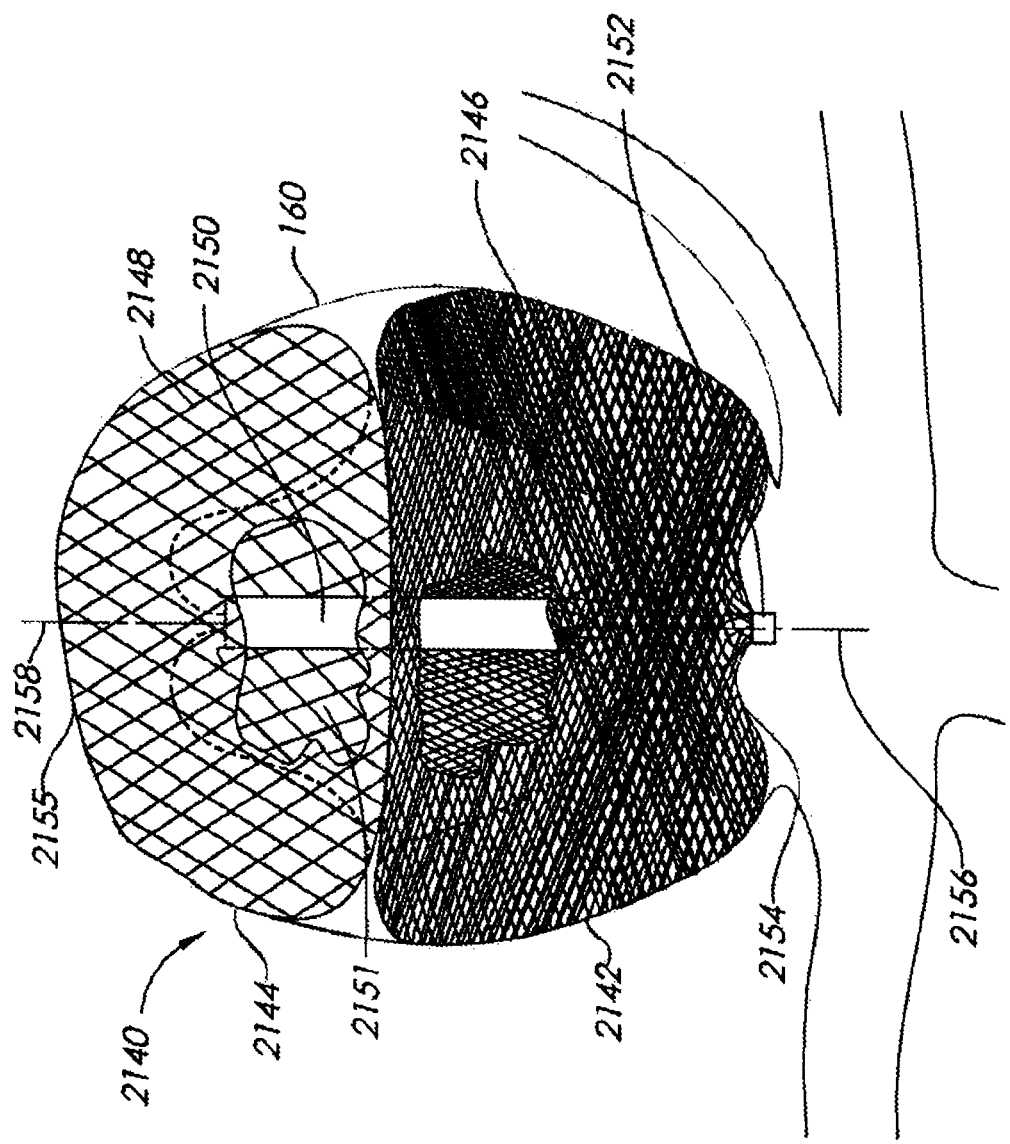
FIG. 57B is a partially cut-away view of the multi-lobe mesh device of FIG. 57A.
Figure 57C:
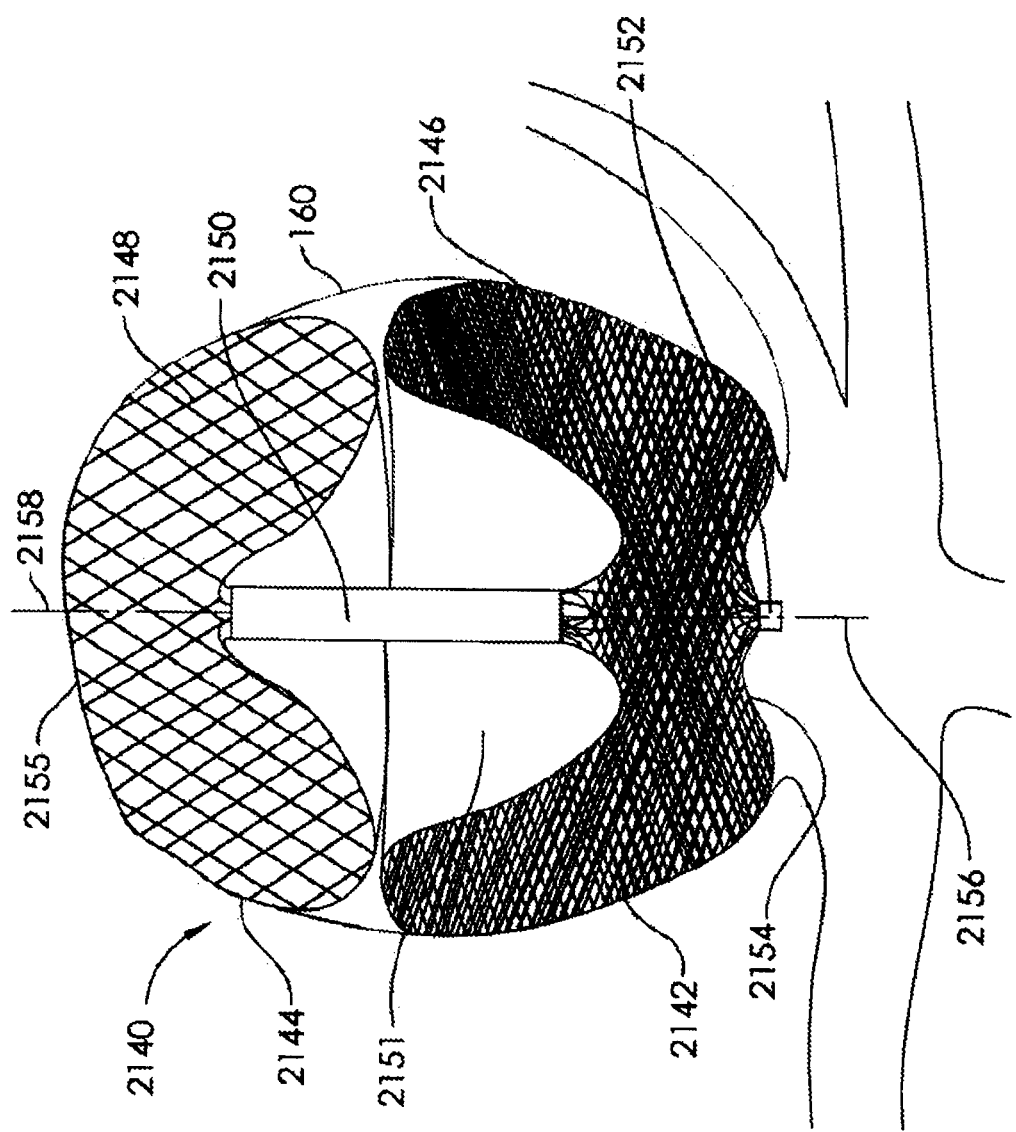
FIG. 57C is partial sectional view of the multi-lobe mesh device of FIG. 57A.
Figure 58:
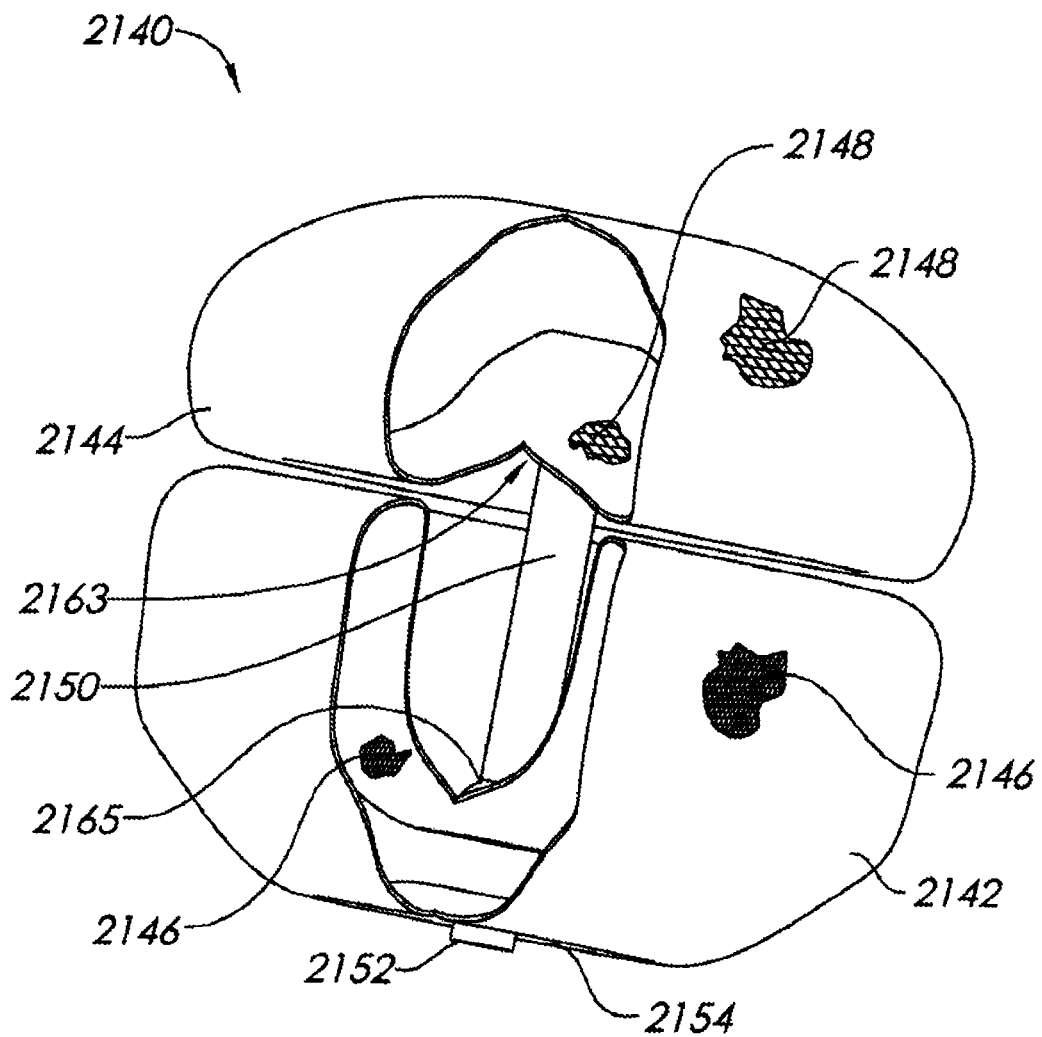
FIG. 58 is a partially cut-away perspective view of the multi-lobe mesh device of FIG. 57A.
Figure 59:
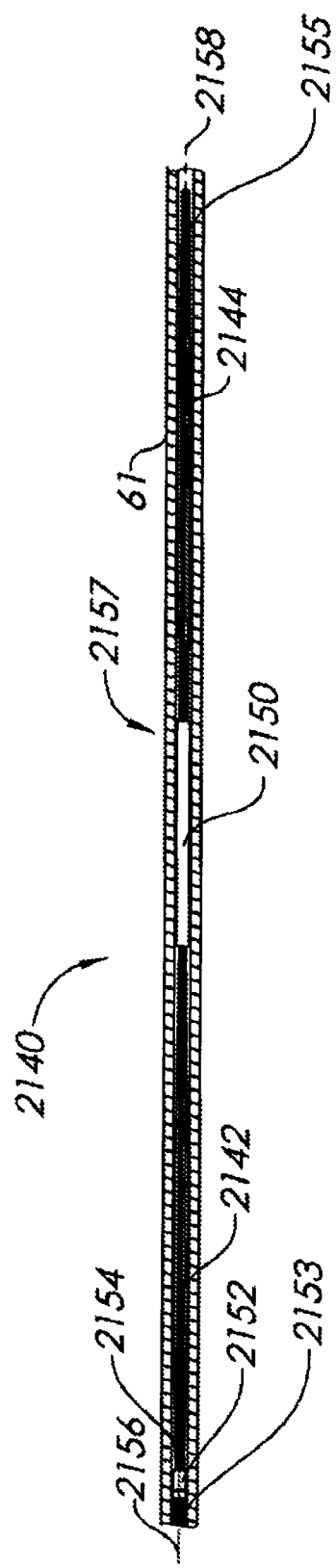
FIG. 59 is an elevation view in partial section of a distal end of a delivery catheter with the device for treatment of a patient's vasculature of FIGS. 57A-58 disposed therein in a collapsed constrained state.

FIGS. 57A-58 illustrate an embodiment of a multi-lobe mesh device 2140 having a proximal lobe 2142 and a distal lobe 2144. The filaments 2146 of the proximal lobe 2142 and the filaments 2148 of the distal lobe 2144 are secured to each other by a support member 2150. In some embodiments, a proximal hub 2152 secures the filaments 2146 of the proximal lobe 2142 at its proximal end 2154. In some embodiments, the proximal lobe 2142 may be constructed in a similar fashion and with similar materials as the proximal lobe 1802 of the multi-lobe mesh device 1800 of FIGS. 45-47. In some embodiments, the distal lobe 2144 may be constructed in a similar fashion and with similar materials as the center lobe 1804 of the multi-lobe mesh device 1800 of FIGS. 45-47. In some embodiments, the distal lobe 2144 of the multi-lobe mesh device 2140 may be constructed without a hub at its distal end 2155 (FIG. 59). This may be done to protect the dome 161 of an aneurysm (vascular defect 160). A support member 2150 is positioned between the proximal lobe 2142 and distal lobe 2144.

The distal lobe 2144 may have a generally convex shape at its distal end. The proximal lobe 2142 may have a generally convex shape at its proximal end. The support member 2150 is positioned between the distal and proximal lobes 2144, 2142. The expanded states of the distal and proximal lobes 2144, 2142 define a toroidal cavity 2151 through which the support member 2150 extends.

In some embodiments, the support member 2150 may comprise a substantially rigid cylindrical member. In some embodiments, the support member 2150 may comprises a hypo tube. Rigidity in the support member 2150 may aid in maintaining a longitudinal axis 2156 of the proximal lobe 2142 and a longitudinal axis 2158 of the distal lobe 2144 at a generally fixed angle to each other, when the proximal lobe 2142 and the distal lobe 2144 are each in their expanded configurations. Rigidity in the support member 2150 may aid in maintaining the longitudinal axis 2156 of the proximal lobe 2142 and the longitudinal axis 2158 of the distal lobe 2144 substantially parallel to each other, when the proximal lobe 2142 and the distal lobe 2144 are each in their expanded configurations. Rigidity in the support member 2150 may aid in maintaining the longitudinal axis 2156 of the proximal lobe 2142 and the longitudinal axis 2158 of the distal lobe 2144 substantially collinear with each other, when the proximal lobe 2142 and the distal lobe 2144 are each in their expanded configurations. Maintenance of alignment between the proximal lobe 2142 and the distal lobe 2144 can aid "fit" of the multi-lobe mesh device 2140 within an aneurysm. In some embodiments it can aid fit within an aneurysm having a generally symmetric shape.

In some embodiments, the distal lobe 2144 may have an additional distal hub (and thus not be made with the castellated mandrel). In these embodiments, the additional distal hub may be radiolucent, and thus allow visualization on x-ray or fluoroscopy. In these embodiments, the filaments may be mostly or all nitinol. The resistance to force that the support member 2150 provides may limit the effects of "clot compression" as described herein. In embodiment of FIGS. 57A-58, the support member 2150 constructed from a hypo tube supplies rigid axial support against both compressive forces and tensile forces between the proximal end 2163 of the distal lobe 2144 and the distal end 2165 of the proximal lobe 2142.

Turning to FIG. 59, the multi-lobe mesh device 2140 is shown in a radially constrained state for delivery along a longitudinal axis 2158 through a microcatheter 61. The multi-lobe mesh device 2140 is releasably coupled to a delivery apparatus 2153 at its proximal end 2154. The distal end 2155 of the multi-lobe device 2140 in its radially constrained state corresponds to a distal extremity of the distal lobe 2144. The serial array 2157 of the two lobes 2142, 2144 and the support member 2150 assures that upon delivery, there are no layer overlaps that would increase profile. The multi-lobe mesh device 21400 thus has a small radially constrained profile, and may be delivered through microcatheter 61 having an inner diameter as small as 0.021" and even as small as 0.017".

Figure 60:
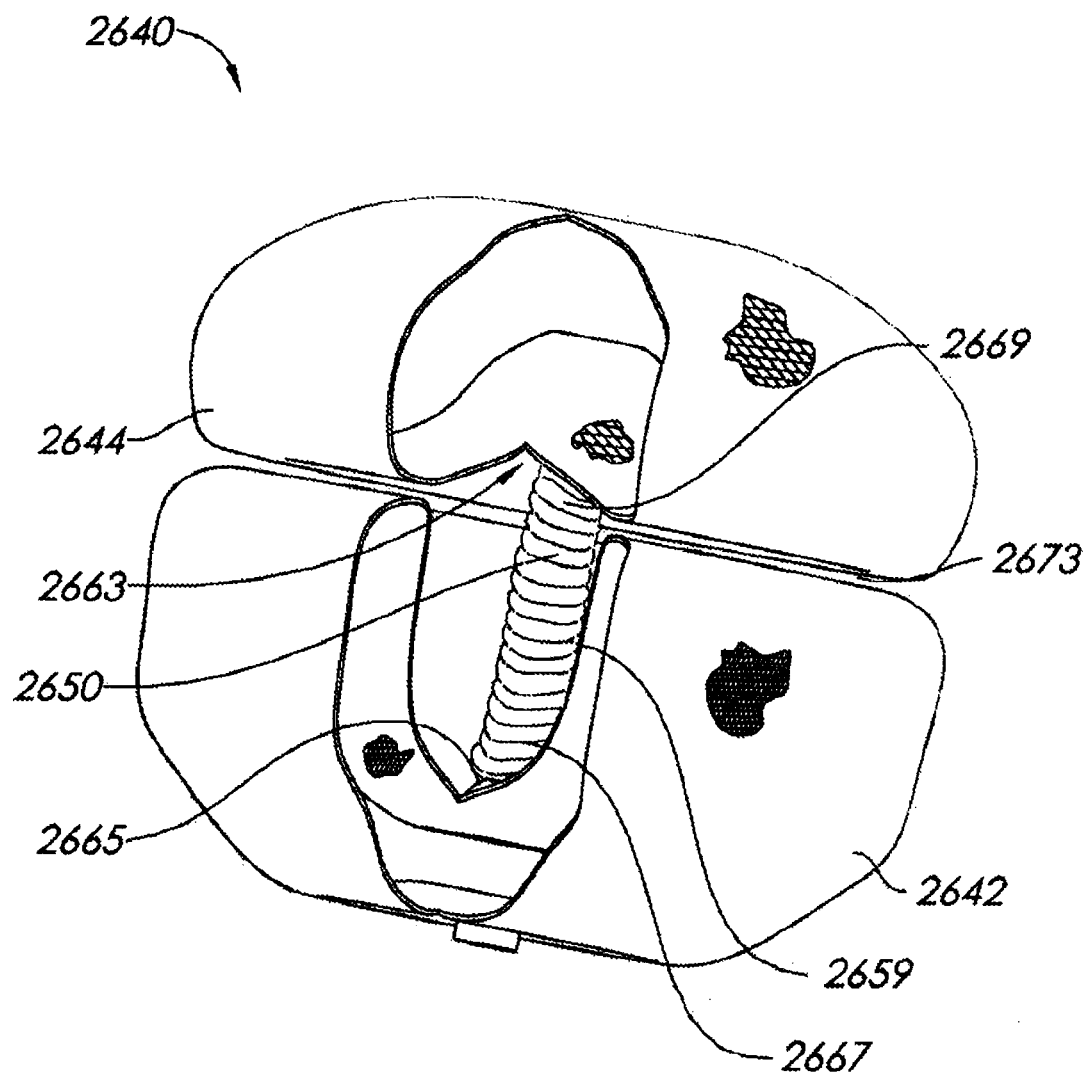
FIG. 60 is a partially cut-away perspective view of an embodiment of a multi-lobe mesh device.

In FIG. 60, a multi-lobe mesh device 2640 having similar characteristics and components to the multi-lobe mesh device 2140 of FIGS. 57A-59 is shown, but the support member 2650 of the multi-lobe mesh device 2640 comprises a coil 2659. The coil 2659 may be constructed of stainless steel, nitinol, or other suitable materials, or may be constructed from radiopaque material, such as platinum or platinum alloys. In some embodiments, the coil 2659 supplies rigid axial support against compressive forces, while allowing for some longitudinal separation or elongation between the proximal lobe 2642 and the distal lobe 2644. In some embodiments, the coil 2659 is an extension spring that applies a bias between the proximal lobe 2642 and the distal lobe 2644, forcing them together. When the extension spring is at rest, the extension spring is not compressible to a smaller length—i.e., each winding of the spring is in contact with adjacent windings at first and second circumferential points on each winding. This may aid the manufacture of the multi-lobe mesh device 2640, allowing the extension spring to be held in an at least partially extended configuration, with at least some space between winds in the spring while the distal end 2665 of the proximal lobe 2642 is attached to the proximal end 2667 of the extension spring and the proximal end 2663 of the distal lobe 2644 is attached to the distal end 2669 of the extension spring. After assembly of the extension spring with the proximal lobe 2642 and the distal lobe 2644, the extension spring serves to align the proximal lobe 2642 with the distal lobe 2644 and hold them adjacent to each other at a central portion 2673. When the multi-lobe mesh device 2640 is placed through a microcatheter having a tortuous shape, the coil 2659 adds flexibility, thus requiring less force to push the multi-lobe mesh device 2640 through the microcatheter. The multi-lobe mesh device 2640 having a coil 2659 as the support member 2650 is also more pliable and when delivered into an aneurysm may provide improved safety. The multi-lobe mesh device 2640 having a coil 2659 as the support member 2650 may also be more easily oriented and aligned within aneurysms having irregular shapes.

Figure 61:
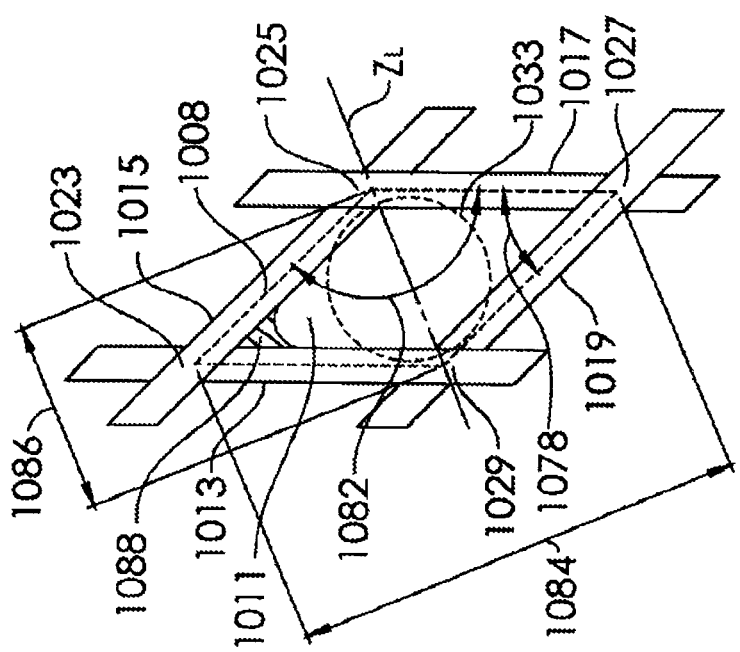
FIG. 61 is a single diamond-shaped module in a multi-lobe mesh device.

As illustrated in FIG. 61, modular braid density ($BD_M$) is a two-dimensional representation of the percent area coverage of filaments in a substantially diamond-shaped module 1008 within the braid. Braid density (BD) as described herein is different from the traditional "braid wire density" which is described in picks per inch (PPI) or picks per centimeter. "Braid wire density" is not a ratio of areas, but rather the number of wire crossings within a particular length of a tubular section. "Braid wire density" is blind to the amount of material coverage within a certain area, because it does not take into account the wire diameter or diameters. Braid density (BD), on the other hand, is specific to the percent of material coverage within a certain area. The substantially diamond-shaped module 1008 is a two-dimensional area $A_M$ inside the diamond-shaped dashed lines in FIG. 50D. The substantially diamond-shaped module 1008 includes a substantially diamond-shaped opening 1011 having an area $A_O$, which is surrounded by four filaments: a first filament 1013, a second filament 1015, a third filament 1017, and a fourth filament 1019. As will be described further, the four filaments 1013, 1015, 1017, 1019 may comprise four individual wires, or alternatively, two or more filaments may be made from the same wire. The four filaments 1013, 1015, 1017, 1019 cross each other around the diamond-shaped opening 1011 at a first crossing 1023 between first filament 1013 and second filament 1015, a second crossing 1025 between second filament 1015 and third filament 1017, a third crossing 1027 between third filament 1017 and fourth filament 1019, and a fourth crossing 1029 between fourth filament 1019 and first filament 1013. The area $A_M$ within the diamond-shaped module 1008 and the area $A_O$ within the diamond-shaped opening 1011 may each be approximated by the formula for area of a parallelogram (base multiplied by height, where height is perpendicular to the base). The four dashed lines in FIG. 61 are each centered between the two outer extents of the filament transverse thickness (e.g., filament width or circular filament diameter). Therefore, the area $A_M$ of the diamond-shaped module 1008 includes the area $A_O$ of the diamond-shaped opening 1011 and the area of one-half of the thickness of each of the four filaments 1013, 1015, 1017, 1019 surrounding the diamond-shaped opening 1011. As mentioned, two or more of the filaments may have a different thickness from each other, or all may be the same thickness. The modular braid density ($BD_M$) calculated at a single module is:

$$BD_M = (A_M - A_O)/A_M$$

where $A_M$ is area of the diamond-shaped module, and $A_O$ is the area of the diamond-shaped opening.

In an embodiment of a braided tubular member having a fixed diameter, fixed circumference, and a fixed number of filaments, the number of diamond-shaped modules 1008 fitting within the fixed circumference will not change, regardless of how sparsely or densely the braid is formed. Therefore, the module width 1084 will remain the same dimension, regardless of how sparsely or densely the braid is formed. However, the module length 1086 will be shorter as the braid is formed more densely, and the module length 1086 will be longer as the braid is formed more sparsely. During braiding, to accommodate this change in the module length 1086 without a change in module width 1084, filament 1015 and filament 1017 will slide over one another at crossing 1025 and filament 1013 and filament 1019 will slide over one another at crossing 1029 while angle 1082 and the angle across from angle 1082 change. In conjunction with this, filament 1013 and filament 1015 will swivel in relation to one another at crossing 1023 and filament 1017 and filament 1019 will swivel in relation to one another at crossing 1027 while angle 1078 and the angle across from angle 1078 change. For example, as the braid is wound more densely, angle 1082 and the angle across from angle 1082 will both increase while angle 1078 and the angle across from angle 1078 both decrease. Moreover, as the braid is wound more sparsely, angle 1082 and the angle across from angle 1082 will both decrease while angle 1078 and the angle across from angle 1078 both increase. It should be noted that angle 1082 in braiding nomenclature would be two times the "braid angle".

The increase or decrease in module length 1086 with braiding "density" change, coupled with the constant module width 1084, means that the number of modules in a certain circumferential "row" will not change with a change in angles 1078, 1082, but the number of modules in a certain axial "column" will change. To calculate the cylindrical braid density ($BD_C$), one must sum both the numerators and denominators of all of the modular braid densities within the cylindrical area having k modules, and then take the ratio:

$$BDC = \Sigma(A_Mk - A_Ok)/\Sigma(A_Mk)$$

k=1, 2, 3, . . . , n
where $A_M$ is area of the diamond-shaped module, and
$A_O$ is the area of the diamond-shaped opening, and In the case that there is some variance in the modular braid densities ($BD_M$) over a specific portion of a braided tubular member, or a mesh device made from a braided tubular member, the cylindrical braid density ($BD_C$) may be calculated. A first example of varying modular braid densities ($BD_M$) is in a transition portion 1003, where modular braid densities ($BD_M$) increase or decrease along the longitudinal axis $Z_L$. A second example of varying modular braid densities ($BD_M$) is in a mesh device having a spherical or globular shape, where the modular braid densities ($BD_M$) decrease towards the outer radius of the mesh device and increase towards the center or longitudinal axis $Z_L$ of the mesh device. It is assumed that the key braid density (BD) in a braid portion that is located near the maximum flow into a vascular defect, such as an aneurysm, is the braid density (BD) at the most expanded diameter. The braid density (BD) inherently becomes greater towards the central axis of the mesh device, because the effective diameter (and thus circumference) decreases, thus leaving less space for the same number of filaments 1005, and thus decreasing the module width 1084 of each module.

In several embodiments of mesh devices, the mesh device is formed from a braided tubular member having at least two distinct braided portions 1002, 1004, so that the mesh device itself may have at least two distinct braided portions. One of the main purposes of having at least two braided portions, is that a more sparsely braided portion may be mechanically easier to diametrically constrain for delivery within the small lumen of a microcatheter 61 and provide a more flexible device for delivering through a tortuous path, while a more densely braided portion may be more effective in disrupting blood flow, for example, when the more densely braided portion is placed at the neck or opening of an aneurysm or other vascular defect. As the second braided portion 1004 is braided more densely (i.e., with increased angle 1082 and decreased angle 1078), the resistance to flow through the diamond-shaped opening 1011 increases. The flow through a diamond-shaped opening 1011 can be characterized by the hydraulic diameter ($D_H$) 1033, a theoretical circular diameter which represents the same flow characteristics as the diamond-shaped opening 1011. Hydraulic diameter ($D_H$) is typically used to represent flow through various non-circular lumens or openings, like the diamond-shape opening 1011. This is because non-circular openings may have low flow zones, like the low flow zone 1088 in the diamond-shaped opening 1011. The formula for hydraulic diameter ($D_H$) is:

$$D_H = (4 \times A_O)/P_O$$

Where $A_O$ is the area of the diamond-shaped opening, and
$P_O$ is the perimeter of the diamond-shaped opening.

Braid density (BD) may be used to compare one portion of the braided tubular member to another portion of the braided tubular member. Braid density (BD) may also be used to compare a portion adjacent the longitudinal axis $Z_L$ of the braided tubular member with the most expanded section within the same portion of the braided tubular member. Braid density (BD) may be used to compare one portion of a mesh device constructed from the braided tubular member to another portion of the mesh device constructed from the braided tubular member, for example, the most expanded section of a first portion with the most expanded portion of a second portion. As mentioned, the most expanded section of a portion intended to disrupt flow (for example, at the neck of an aneurysm), is relevant in predicting the effectiveness in disrupting flow in a worst-case, high flow location. Braid density may also be represented as the average (i.e., mean, median) of several different portions of a braided tubular member of a mesh device made from the braided tubular member. Braid density may also be represented as the average of measurements of the same portion of several braided tubular members or mesh devices constructed from braided tubular members.

Thrombus Removal

Figure 62:
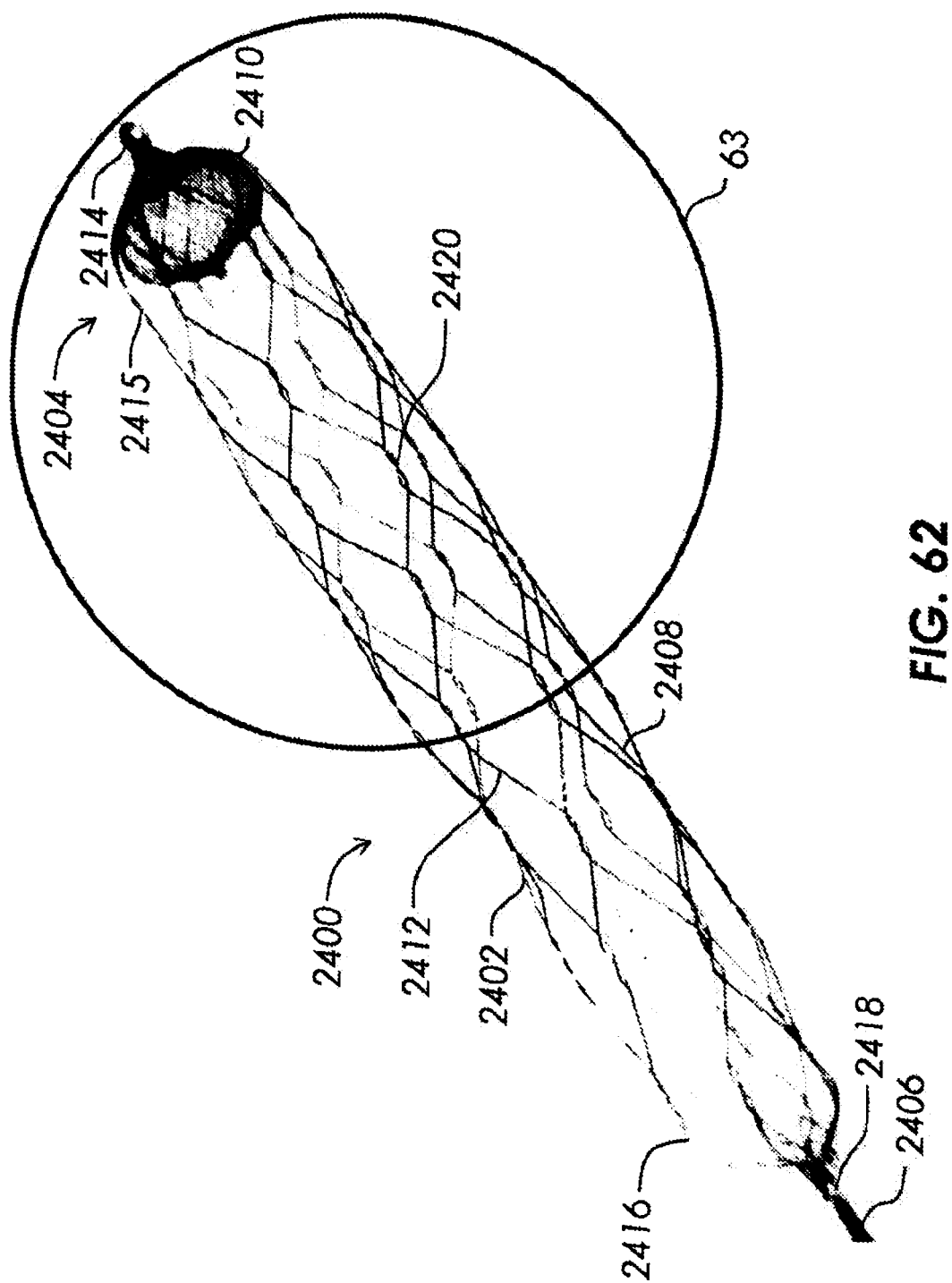
FIG. 62 is a perspective view of an embodiment of a self-expanding device for removal of thrombus from a patient's vasculature.
Figure 63:
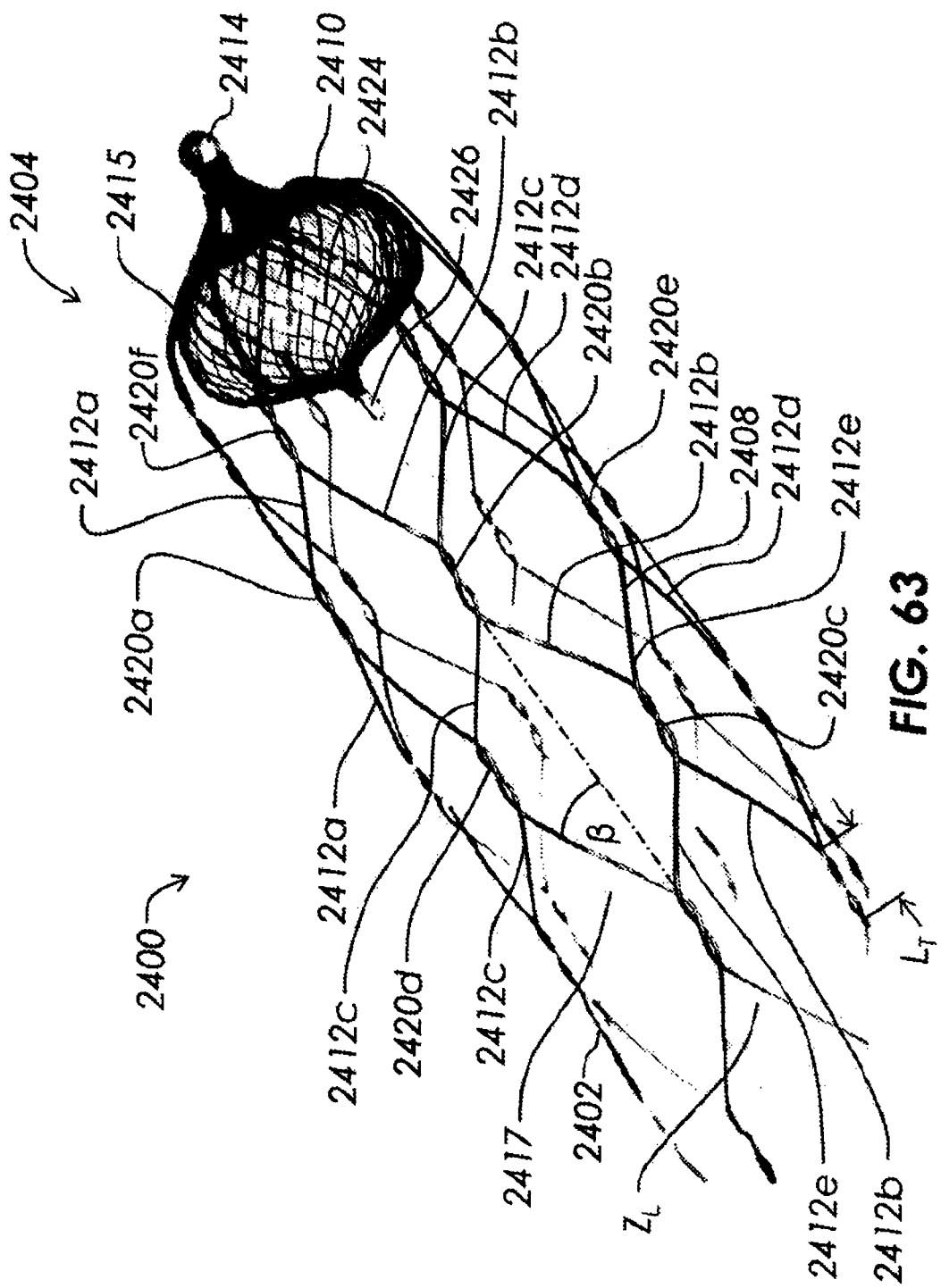
FIG. 63 is a detail view of the self-expanding device of FIG. 62 taken within circle 63.

FIGS. 62 and 63 illustrate a thrombus removal device 2400 having a self-expanding structure 2402 at its distal end 2404. Patients exhibiting ischemic stroke often have thrombi blocking blood flow to portions of the brain. Removal of these thrombi can allow recovery of symptoms, and can even be life-saving. The self-expanding structure 2402 is secured to an elongate shaft 2406 and has a radially constrained configuration for delivery through a microcatheter or sheath, and an expanded configuration (as shown in FIGS. 62 and 63). The self-expanding structure 2402 includes a cylindrical engagement structure 2408 and a trapping structure 2410. The cylindrical engagement structure 2408 is configured to engage thrombus within its boundaries, and the trapping structure 2410 is located at the distal end of the cylindrical engagement structure 2410 and is configured to maintain the captured thrombus within the cylindrical engagement structure 2408 as the thrombus removal device 2400 is removed from the patient.

The cylindrical engagement structure 2408 has a distal end 2415 and a proximal end 2416, and is formed from several wires 2412, in some embodiments, about 10 to about 18 wires, or about 12 wires. In some embodiments, the cylindrical engagement structure 2408 is formed from nitinol wire. In other embodiments the cylindrical engagement structure 2408 is formed from Cobalt-Chromium alloys or stainless steel. In some embodiments, the transverse dimension or diameter of the wire is between about 0.0008" and 0.0035", or about 0.001" to about 0.003", or about 0.002". In some embodiments, the wires 2412 may be formed into the cylindrical engagement structure 2408 by hand or by use of and automated or partially-automated braiding apparatus and process, such as the braiding apparatus and process described in the commonly assigned U.S. Pat. No. 8,261, 648, "Braiding Mechanism and Methods of Use" by Marchand et al., which is herein incorporated by reference in its entirety for all purposes. The wires 2412 are secured at the distal end 2415 of the cylindrical engagement structure 2408 by a distal hub 2414 and are secured at the proximal end 2416 by a proximal band 2418. Turning to FIG. 63, the cylindrical engagement structure 2408 includes wires 2412*a-p* which are wound to each other with a series of twists 2420*a*-N, where N=the total number of twists 2420. In FIG. 63, the twists 2420 are shown as one complete turn, or 360°, but other parameters may be used to make cylindrical engagement structures 2408 of varying embodiments (e.g., two complete turns, one and one-half turn). By varying the number of turns, the length $L_T$ of each twist 2420 may be varied. The length $L_T$ may range from about 0.25 mm to about 3 mm, or about 0.35 mm to about 1 mm, or about 0.5 mm. Following the particular wire 2412*b* from a location near the distal end 2404 and moving proximally, wire 2412*b* is wound with wire 2412*a* at twist 2420*f*. Wire 2412*b* is then wound with wire 2412*c* at twist 2420*b*. Wire 2412*b* is then wound with wire 2412*e* at twist 2420*c*. Because of the full (360°) turn, wire 2412*b* continues following a general spiral pattern as it is wound with the other wires 2412. Other wires, like 2412*a* and 2412*e* follow a general spiral pattern, but in the opposite direction of the general spiral pattern of wire 2412*b*. In certain other embodiments, the twists may be varied in terms of the total number of turns, for example, half turn increments, which allow a variety of other structures to be formed. In some embodiments, braid angle β may be varied along the length of the longitudinal axis $Z_L$. Braid angle β is one-half of the angle between two twisted wires (e.g., 2412*b* and 2412*c*) as they extend from a twist (e.g., 2420*b*).

Because the wires 2412 are held together at the twists 2420, the cylindrical engagement structure 2408 is durable and maintains its expanded shape as it engages with thrombus, meets the blood vessel wall, and is pulled through the blood vessel. The trapping structure 2410 may comprise a braided mesh structure comprising filaments 2424 that are secured at their ends by the distal hub 2414 and a proximal hub 2426. The braided mesh structure 2422 has a radially constrained configuration for delivery through a microcatheter. In some embodiments, the trapping structure 2410 may be located entirely within the cylindrical engagement structure 2408. In some embodiments, the transverse dimension or diameter of the filaments 2424 is between about 0.0005" and 0.002" or about 0.00075" to about 0.0015", or about 0.001". Both the cylindrical engagement structure 2408 and the trapping structure 2410 may be heat formed to maintain their shape. In some embodiments, this may be done at a temperature of around 500° C. In some embodiments, the cylindrical engagement structure 2408 and the trapping structure may each be heat formed separately from one another. In some embodiments, the cylindrical engagement structure 2408 and the trapping structure 2410 may be heat formed together.

The braided mesh structure 2422 of the trapping structure 2410 has an expanded configuration (as seen in FIGS. 62 and 63) having a braid density BD sufficiently high enough to maintain thrombus within the cylindrical engagement structure 2408 as the thrombus removal device 2400 is pulled proximally through a blood vessel or through another catheter (guiding catheter, delivery sheath, etc.). The conformity of the cylindrical engagement structure 2408 to the vessel wall combined with the inability for thrombus to pass through the trapping structure 2410 combine to create a compartment 2417 to trap thrombus and shuttle it proximally. In some cases, the thrombus removal device 2400 is pulled into a microcatheter after being used to remove thrombus from a blood vessel. In some cases, the thrombus removal device 2400 is pulled only into a larger catheter or sheath after being used to remove thrombus from a blood vessel. In some cases, the thrombus removal device 2400 is pulled along with a microcatheter into a larger catheter or sheath after being used to remove thrombus from a blood vessel. Another characteristic of the trapping structure 2410 is that it may be made in some embodiments with a braid density BD such that it is capable of trapping thrombus, while simultaneously allowing normal blood to flow through, for example, to perfuse distal vasculature and end tissue.

FIGS. 64-67 illustrate the thrombus removal device 2400 in use to remove a thrombus 2430 from a blood vessel 2428. A catheter 2432 is delivered so that its distal end 2419 is distal to the thrombus 2430 as in FIG. 64, or adjacent the distal end 2421 of the thrombus 2430, and the thrombus removal device 2400 is pushed out of the catheter 2432 such that the trapping structure 2410 expands and is located distal the thrombus and cylindrical engagement structure 2408 expands around and encompasses the thrombus 2430 (FIG. 65). The thrombus removal device 2400 is pulled proximally into the catheter 2432, trapping the thrombus 2430 (FIG. 66) and the thrombus removal device 2400 is removed (FIG. 67).

Although the foregoing invention has, for the purposes of clarity and understanding, been described in some detail by way of illustration and example, it will be obvious that certain changes and modifications may be practiced which will still fall within the scope of the appended claims.

What is claimed:

1. A device for treatment of an aneurysm within a patient's vasculature, comprising:
  a distal self-expanding resilient permeable shell having a proximal end, a distal end, and a longitudinal axis, the distal permeable shell comprising a first plurality of elongate resilient filaments having a braided structure with a plurality of openings formed between the braided filaments, wherein the first plurality of filaments are gathered at least at the proximal end thereof, wherein the distal permeable shell has a radially constrained elongated state configured for delivery within a microcatheter and an expanded state with an axially shortened configuration relative to the radially constrained state, wherein the expanded state of the distal permeable shell has a convex shape at the distal end of the distal permeable shell;
  a proximal self-expanding resilient permeable shell having a proximal end, a distal end, and a longitudinal axis, the proximal permeable shell comprising a second plurality of elongate resilient filaments having a braided structure with a plurality of openings formed between the braided filaments, wherein the second plurality of filaments are gathered at least at the proximal end thereof, wherein the proximal permeable shell has a radially constrained elongated state configured for delivery within the microcatheter and an expanded state with an axially shortened configuration relative to the radially constrained state, wherein the expanded state of the proximal permeable shell has an outer surface with a generally convex shape at the proximal end of the proximal permeable shell; and an elongate support member having a proximal end and a distal end, the elongate support member positioned between the distal and proximal permeable shells, wherein the expanded states of the distal and proximal permeable shells define a toroidal cavity through which the elongate support member extends, and wherein at least a portion of a proximal-most surface of the expanded state of the distal permeable shell is in contact with at least a portion of a distal-most surface of the expanded state of the proximal permeable shell.

2. The device of claim 1, wherein an average size of the plurality of openings in the distal permeable shell is larger than an average size of the plurality of openings in the proximal permeable shell.

3. The device of claim 2, wherein the average size of the plurality of openings in the distal permeable shell is selected from the group consisting of about 300 µm to about 900 µm, about 300 µm to about 700 µm, and 300 µm to about 500 µm.

4. The device of claim 2, wherein the average size of the plurality of openings in the proximal permeable shell is selected from the group consisting of about 50 µm to about 200 µm, about 100 µm to about 200 µm, and 50 µm to about 150 µm.

5. The device of claim 1, wherein the braided structure of the distal permeable shell has a first braid density and the braided structure of the proximal permeable shell has a second braid density, wherein the first braid density is greater than the second braid density.

6. The device of claim 5, wherein the first braid density is between about 0.10 and 0.20.

7. The device of claim 5, wherein the second braid density is between about 0.15 and 0.40.

8. The device of claim 1, wherein the elongate support member is rigid.

9. The device of claim 1, wherein the elongate support member is a hypo tube.

10. The device of claim 1, wherein the elongate support member is a coil.

11. The device of claim 10, wherein the coil is an extension spring.

12. The device of claim 1, wherein the first plurality of filaments of the distal permeable shell are gathered at the distal end of the distal permeable shell.

13. The device of claim 1, wherein each of the first plurality of filaments of the distal permeable shell has a first end and a second end, wherein the first and second ends of the first plurality of filaments of the distal permeable shell are gathered at the proximal end of the distal permeable shell.

14. The device of claim 1, wherein the expanded shape of the distal permeable shell contacts the expanded shape of the proximal permeable shell.

15. The device of claim 1, wherein the expanded shape of the distal permeable shell and the expanded shape of the proximal permeable shell form a substantially globular shape.

16. The device of claim 1, wherein the second plurality of filaments are gathered at the proximal end of the proximal permeable shell by a hub.

17. The device of claim 16, wherein the hub is recessed below an expanded periphery of the proximal end of the proximal permeable shell.

18. The device of claim 1, wherein the elongate support member has a length of between about 2 mm and about 10 mm.

19. A device for treatment of an aneurysm within a patient's vasculature, comprising:

a distal self-expanding resilient permeable shell having a proximal end, a distal end, and a longitudinal axis, the distal permeable shell comprising a first plurality of elongate resilient filaments having a braided structure with a plurality of openings formed between the braided filaments, wherein the first plurality of filaments are gathered at least at the proximal end thereof, wherein the distal permeable shell has a radially constrained elongated state configured for delivery within a microcatheter and an expanded state with an axially shortened configuration relative to the radially constrained state, wherein the expanded state of the distal permeable shell has a convex shape at the distal end of the distal permeable shell;

a proximal self-expanding resilient permeable shell having a proximal end, a distal end, and a longitudinal axis, the proximal permeable shell comprising a second plurality of elongate resilient filaments having a braided structure with a plurality of openings formed between the braided filaments, wherein the second plurality of filaments are gathered at least at the proximal end thereof, wherein the proximal permeable shell has a radially constrained elongated state configured for delivery within the microcatheter and an expanded state with an axially shortened configuration relative to the radially constrained state, wherein the expanded state of the proximal permeable shell has an outer surface with a generally convex shape at the proximal end of the proximal permeable shell; and a rigid support means to maintain a longitudinal axis of the expanded state of the distal permeable shell at a fixed angle to a longitudinal axis of the expanded state of the proximal permeable shell, wherein the expanded states of the distal and proximal permeable shells define a toroidal cavity through which the rigid support means extends, and wherein at least a portion of a proximal-most surface of the expanded state of the distal permeable shell is in contact with at least a portion of a distal-most surface of the expanded state of the proximal permeable shell.

20. The device of claim 19, wherein the rigid support means comprises a hypotube.

* * * * *